United States Patent
Liu et al.

(10) Patent No.: US 12,249,145 B2
(45) Date of Patent: Mar. 11, 2025

(54) PROMPT METHOD AND ELECTRONIC DEVICE FOR FITNESS TRAINING

(71) Applicant: HUAWEI TECHNOLOGIES CO., LTD., Shenzhen (CN)

(72) Inventors: Hang Liu, Shenzhen (CN); Jiabing Yan, Shenzhen (CN); Xindi Yu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 401 days.

(21) Appl. No.: 17/636,580

(22) PCT Filed: Jul. 16, 2020

(86) PCT No.: PCT/CN2020/102257
§ 371 (c)(1),
(2) Date: Feb. 18, 2022

(87) PCT Pub. No.: WO2021/036562
PCT Pub. Date: Mar. 4, 2021

(65) Prior Publication Data
US 2022/0277845 A1    Sep. 1, 2022

(30) Foreign Application Priority Data
Aug. 30, 2019 (CN) .......................... 201910817621.1

(51) Int. Cl.
*G06V 20/40* (2022.01)
*G06V 20/64* (2022.01)
(Continued)

(52) U.S. Cl.
CPC .............. *G06V 20/42* (2022.01); *G06V 20/64* (2022.01); *G06V 40/10* (2022.01); *G06V 40/23* (2022.01); *G16H 20/30* (2018.01); *G16H 40/67* (2018.01)

(58) Field of Classification Search
CPC ........ G06V 20/42; G06V 20/64; G06V 40/10; G06V 40/23; G16H 20/30; G16H 40/67; G06F 18/22
(Continued)

(56) References Cited

U.S. PATENT DOCUMENTS

| | | | |
|---|---|---|---|
| 8,444,532 B1 | 5/2013 | Barcena | |
| 2011/0077127 A1* | 3/2011 | Ishii | A63B 21/0058 482/8 |

(Continued)

FOREIGN PATENT DOCUMENTS

| | | |
|---|---|---|
| CN | 103282907 A | 9/2013 |
| CN | 104750778 A | 7/2015 |

(Continued)

OTHER PUBLICATIONS

Itu-T H.264(Jun. 2019), Series H: Audiovisual and Multimedia Systems, Infrastructure of audiovisual services—Coding of moving video, Advanced video coding for generic audiovisual services, total 836 pages.

*Primary Examiner* — Joy Chng
(74) *Attorney, Agent, or Firm* — Rimon PC

(57) ABSTRACT

This application provides a prompt method for fitness training and an electronic device, and relates to the field of artificial intelligence. The method includes: obtaining required training space, where the required training space is used to complete one or more training actions; determining, based on a training scenario in which a user is located and the required training space, a training location recommended to the user; and recording a training action of the user based on the training location recommended to the user. A suitable training location is recommended to the user based on the training scenario in which the user is located and the required training space. Therefore, the user can also nor- (Continued)

mally perform training in a scenario in which exercise space is limited, for example, when there is an obstruction or a site is insufficient.

17 Claims, 35 Drawing Sheets

(51) Int. Cl.
    *G06V 40/10*        (2022.01)
    *G06V 40/20*        (2022.01)
    *G16H 20/30*        (2018.01)
    *G16H 40/67*        (2018.01)

(58) Field of Classification Search
    USPC ......................................................... 705/2–3
    See application file for complete search history.

(56) References Cited

U.S. PATENT DOCUMENTS

2016/0086500 A1* 3/2016 Kaleal, III ............... A61B 5/43
                                                                                                                                                            434/257

2017/0100637 A1* 4/2017 Princen ................... G16H 20/30
2019/0143191 A1* 5/2019 Ran ....................... A63B 71/0054
                                                                                                                               482/1

FOREIGN PATENT DOCUMENTS

| | | | | |
|---|---|---|---|---|
| CN | 105115490 A | 12/2015 | | |
| CN | 105204625 A | 12/2015 | | |
| CN | 105841687 A | 8/2016 | | |
| CN | 106228127 A | 12/2016 | | |
| CN | 106776776 A | 5/2017 | | |
| CN | 107045623 A | 8/2017 | | |
| CN | 107239750 A | 10/2017 | | |
| CN | 107256330 A | 10/2017 | | |
| CN | 108153421 A | 6/2018 | | |
| CN | 108446026 A | 8/2018 | | |
| CN | 108960002 A | 12/2018 | | |
| CN | 109813317 A | 5/2019 | | |
| CN | 109815930 A | 5/2019 | | |
| CN | 110038274 A | 7/2019 | | |
| EP | 2455927 A1 * | 5/2012 | ......... | G06K 9/00798 |
| WO | WO-2013022890 A1 * | 2/2013 | ........... | A61B 5/0002 |

* cited by examiner

PROMPT METHOD AND ELECTRONIC DEVICE FOR FITNESS TRAINING

CROSS-REFERENCE TO RELATED APPLICATIONS

This application is a national stage of International Application No. PCT/CN2020/102257, filed on Jul. 16, 2020, which claims priority to Chinese Patent Application No. 201910817621.1, filed on Aug. 30, 2019. Both of the aforementioned applications are hereby incorporated by reference in their entireties.

TECHNICAL FIELD

This application relates to the field of electronic technologies, and in particular, to a prompt method and an electronic device for fitness training.

BACKGROUND

In an intelligent fitness solution based on image processing, a training action of a user can be evaluated in a training process, so that the user can get professional guidance without leaving home. However, when training is performed in a scenario in which exercise space is limited, for example, a living room scenario or a dormitory scenario, the following problems exist: an exercise space is insufficient, an obstruction affects action recognition accuracy, or an accident may occur in a training process. Consequently, the user cannot normally perform training.

SUMMARY

This application provides a prompt method for fitness training and an electronic device, so that a user can also normally perform training in a scenario in which exercise space is limited.

According to a first aspect, a prompt method for fitness training is provided, applied to an electronic device, where the method includes: obtaining required training space, where the required training space is used to complete one or more training actions; determining, based on a training scenario in which a user is located and the required training space, a training location is recommended to the user; and recording a training action of the user based on the training location recommended to the user.

In this embodiment of this application, a suitable training location is recommended to the user based on the training scenario in which the user is located and the required training space. Therefore, the user can also normally perform training in a scenario in which exercise space is limited, for example, when there is an obstruction or the site is insufficient.

With reference to the first aspect, in a possible implementation, the obtaining required training space includes: determining the required training space based on an activity space of a coach in a target course video; determining the required training space based on a body shape parameter of the user; determining the required training space based on an activity space of a coach in a target course video and a body shape parameter of the user; or determining the required training space based on a training space parameter defined by the user.

Optionally, the determining the required training space based on the activity space of a coach in a target course video includes: obtaining the target course video; processing the target course video to obtain an activity track of the coach; and determining the activity space of the coach based on the activity track of the coach.

The required training space is determined based on the activity space of the coach in the target course video, and a suitable training location is recommended to the user based on the training scenario and the required training space. The user does not need to select, based on space required by a course, a location for performing training, and the training location is recommended to the user based on the activity space of the coach. The recommended training location is more accurate, and is more suitable for the user to perform training corresponding to the target course video.

Optionally, the body shape parameter of the user includes a height, a weight, a length of an upper arm, a length of a forearm, a length of a thigh, a length of a crus, an eye height, a shoulder height, an elbow height, a functional hand height, a sitting height, a body depth, a weight, a volume, a surface area, and the like.

When the required training space is determined based on the body shape parameter of the user, a training location suitable for the user may be recommended to the user. The recommended training location is more personalized. This improves adaptation between the recommended training location and the training action of the user.

When the required training space is determined based on the activity space of the coach in the target course video and the body shape parameter of the user, both a requirement of space required by the training action and a body shape of the user can be considered, so that a training location suitable for the user can be recommended to the user.

With reference to the first aspect, in a possible implementation, the determining, based on a training scenario in which a user is located and the required training space, a training location recommended to the user includes: starting a camera of the electronic device, and scanning the training scenario; and in a scanning process, calculating a location that is in the training scenario and that meets the required training space, and determining the location as the training location recommended to the user.

With reference to the first aspect, in a possible implementation, the camera is any one of an RGB camera, a depth camera, a wide-angle camera or a camera mounted on a rotatable mechanical structure.

Depth information may be obtained by using the depth camera, so that the training location recommended to the user is more suitable for the user to perform training. A larger field of view can be obtained by using the wide-angle camera or the camera mounted on the rotatable mechanical structure, so that a selection range of the training location recommended to the user can be expanded, and a suitable training location can be found more easily.

With reference to the first aspect, in a possible implementation, the method further includes: determining a current location of the user in the training scenario; and outputting prompt information based on the current location of the user in the training scenario and the training location recommended to the user, to prompt the user to move to the training location recommended to the user.

The user is guided by using the prompt information, so that the user can quickly reach the recommended training location, and the user does not need to determine the location. This improves user experience, and ensures that the user can also normally perform training in a scenario in which exercise space is limited.

With reference to the first aspect, in a possible implementation, the prompt information includes at least one of a picture prompt, a voice prompt, and a notification prompt.

With reference to the first aspect, in a possible implementation, before the recording a training action of the user based on the training location recommended to the user, the method includes: determining that the user moves to the training location recommended to the user; and outputting confirmation information, where the confirmation information is used to prompt the user to start training.

Before the user starts training, the user is prompted to perform a confirmation. This improves user experience.

With reference to the first aspect, in a possible implementation, the method further includes: obtaining a plurality of frames of images of the user, where each frame of an image in the plurality of frames of images includes at least one recognized point; and performing an affine transformation on any two frames of images in the plurality of frames of images based on the at least one recognized point.

The electronic device may obtain a plurality of frames of images of the user, perform subject recognition on the user based on the plurality of frames of images, and perform an affine transformation on a recognized point, to ensure that action matching is not affected by an angle, and ensure that a change of the angle of the user relative to a picture does not affect accuracy of the training action evaluation.

According to a second aspect, an electronic device is provided, including one or more processors, one or more memories, a plurality of application programs, and one or more programs, where the one or more programs are stored in the memory, and when the one or more programs are executed by the processor, the electronic device is enabled to perform the following steps: obtaining required training space, where the required training space is used to complete one or more training actions; determining, based on a training scenario in which a user is located and the required training space, a training location recommended to the user; and recording a training action of the user based on the training location recommended to the user.

In this embodiment of this application, a suitable training location is recommended to the user based on the training scenario in which the user is located and the required training space. Therefore, the user can also normally perform training in a scenario in which exercise space is limited, for example, when there is an obstruction or the site is insufficient.

With reference to the second aspect, in a possible implementation, when the one or more programs are executed by the processor, the electronic device is enabled to perform the following steps: determining the required training space based on an activity space of a coach in a target course video; determining the required training space based on a body shape parameter of the user; determining the required training space based on an activity space of a coach in a target course video and a body shape parameter of the user; or determining the required training space based on a training space parameter defined by the user.

With reference to the second aspect, in a possible implementation, when the one or more programs are executed by the processor, the electronic device is enabled to perform the following steps: starting a camera of the electronic device, and scanning the training scenario; and in a scanning process, calculating a location that is in the training scenario and that meets the required training space, and determining the location as the training location recommended to the user.

With reference to the second aspect, in a possible implementation, the camera is any one of an RGB camera, a depth camera, a wide-angle camera, or a camera mounted on a rotatable mechanical structure.

With reference to the second aspect, in a possible implementation, when the one or more programs are executed by the processor, the electronic device is enabled to perform the following steps: determining a current location of the user in the training scenario; and outputting prompt information based on the current location of the user in the training scenario and the training location recommended to the user, to prompt the user to move to the training location recommended to the user.

With reference to the second aspect, in a possible implementation, the prompt information includes at least one of a picture prompt, a voice prompt, and a notification prompt.

With reference to the second aspect, in a possible implementation, when the one or more programs are executed by the processor, the electronic device is enabled to perform the following steps: determining that the user moves to the training location recommended to the user; and outputting confirmation information, where the confirmation information is used to prompt the user to start training.

With reference to the second aspect, in a possible implementation, when the one or more programs are executed by the processor, the electronic device is enabled to perform the following steps: obtaining a plurality of frames of images of the user, where each frame of an image in the plurality of frames of images includes at least one recognized point; and performing an affine transformation on any two frames of images in the plurality of frames of images based on the at least one recognized point.

According to a third aspect, a prompt method for fitness training is provided, applied to an electronic device, where the method includes: obtaining required training space, where the required training space is used to complete one or more training actions; determining, based on a training scenario in which a user is located and the required training space, a training location recommended to the user; and displaying a first interface, where the first interface includes a first window, the first window is used to display a framing interface of a camera of the electronic device, the first window includes prompt information, and the prompt information is used to prompt the user to move to the training location recommended to the user.

For example, the first interface may be a training interface 501 in FIG. 5(a), FIG. 5(c), and FIG. 5(e), and the first window may be a viewfinder frame 503 in FIG. 5(a), FIG. 5(c), and FIG. 5(e).

With reference to the third aspect, in a possible implementation, the first interface further includes a second window, and the second window is used to display a photography interface of the camera of the electronic device.

For example, the second window may be a camera field of view 504 in FIG. 5(a), FIG. 5(c), and FIG. 5(e).

With reference to the third aspect, in a possible implementation, the prompt information includes a recommended region that is displayed on the ground and that corresponds to the training location recommended to the user.

For example, the recommended region on the ground may be a recommended region 505 in FIG. 5(a), FIG. 5(c), and FIG. 5(e).

With reference to the third aspect, in a possible implementation, the method further includes: obtaining a current location of the user in the training scenario; determining, based on the current location of the user in the training scenario and the training location recommended to the user, whether the user is at the training location recommended to the user; and when the user is not at the training location recommended to the user, displaying a first pop-up box, where the first pop-up box is used to remind the user that the user has not reached the training location recommended to the user, or prompt the user with a movement direction and/or a movement distance; or when the user is, after a preset time expires, still not at the training location recommended to the user, displaying a second pop-up box, where the second pop-up box is used to remind the user that the user has not reach, after the preset time expires, the training location recommended to the user, or prompt the user with a movement direction and/or a movement distance; or when the user is at the training location recommended to the user, displaying a third pop-up box, where the third pop-up box is used to remind the user that the user has reached the training location recommended to the user.

For example, the first pop-up box may be a prompt box 506 in FIG. 5(*a*) and FIG. 6(*a*), the second pop-up box may be a prompt box 506 in FIG. 5(*c*) and FIG. 6(*b*), and the third pop-up box may be a prompt box 506 in FIG. 5(*e*) and FIG. 6(*c*).

With reference to the third aspect, in a possible implementation, when the user is at the training location recommended to the user, the method further includes: displaying a second interface, where the second interface includes confirmation information, and the confirmation information is used to prompt the user to start training.

For example, the second interface may be a training interface 501 in FIG. 8(*a*) to FIG. 8(*e*), and the confirmation information is an action recognition icon 509, a gesture recognition icon 510, an instruction recognition icon 511, a countdown timing icon 512, and a confirmation window 513 in FIG. 8(*a*) to FIG. 8(*e*).

According to a fourth aspect, an electronic device is provided, including one or more processors, one or more memories, a plurality of application programs, and one or more programs, where the one or more programs are stored in the memory, and when the one or more programs are executed by the processor, the electronic device is enabled to perform the following steps: obtaining required training space, where the required training space is used to complete one or more training actions; determining, based on a training scenario in which a user is located and the required training space, a training location recommended to the user; and displaying a first interface, where the first interface includes a first window, the first window is used to display a framing interface of a camera of the electronic device, the first window including prompt information, and the prompt information is used to prompt the user to move to the training location recommended to the user.

With reference to the fourth aspect, in a possible implementation, the first interface further includes a second window, and the second window is used to display a photography interface of the camera of the electronic device.

With reference to the fourth aspect, in a possible implementation, the prompt information includes a recommended region that is on the ground and that corresponds to the training location recommended to the user.

With reference to the fourth aspect, in a possible implementation, when the one or more programs are executed by the processor, the electronic device is enabled to perform the following steps: obtaining a current location of the user in the training scenario; determining, based on the current location of the user in the training scenario and the training location recommended to the user, whether the user is at the training location recommended to the user; and when the user is not at the training location recommended to the user, displaying a first pop-up box, where the first pop-up box is used to remind the user that the user has not reached the training location recommended to the user, or prompt the user with a movement direction and/or a movement distance; or when the user is, after a preset time expires, still not at the training location recommended to the user, displaying a second pop-up box, where the second pop-up box is used to remind the user that the user has not reached, after the preset time expires, the training location recommended to the user, or prompt the user with a movement direction and/or a movement distance; or when the user is at the training location recommended to the user, displaying a third pop-up box, where the third pop-up box is used to remind the user that the user has reached the training location recommended to the user.

With reference to the fourth aspect, in a possible implementation, when the user is at the training location recommended to the user, and when the one or more programs are executed by the processor, the electronic device is enabled to perform the following step: displaying a second interface, where the second interface includes confirmation information, and the confirmation information is used to prompt the user to start training.

According to a fifth aspect, a prompt method for fitness training is provided, applied to an electronic device, where the method includes: obtaining required training space, where the required training space is used to complete one or more training actions; determining, based on the training space, a training course and/or a training action that is recommended to a user; and displaying a third interface, where the third interface includes a third window, and the third window is used to display the training course and/or the training action that is recommended to the user.

For example, the third interface may be a recommendation interface 311 shown in FIG. 11(*a*), and the third window may be recommended content 313 in FIG. 11(*a*).

With reference to the fifth aspect, in a possible implementation, the method further includes: displaying a fourth interface before the third interface is displayed, where the fourth interface includes a fourth window used to enter the third window; detecting a first operation of the user in the fourth window, where the first operation is used to select a first option from a plurality of options; displaying a setting parameter of the first option in response to the first operation; detecting a second operation of the user in the fourth window, where the second operation is used to input the setting parameter of the first option; and displaying the third interface in response to the second operation.

For example, the fourth interface may be a recommendation interface 311 shown in FIG. 11(*b*), and the fourth window may be a user-defined window 314 in FIG. 11(*b*).

According to a sixth aspect, an electronic device is provided, including one or more processors, one or more memories, a plurality of application programs, and one or more programs, where the one or more programs are stored in the memory, and when the one or more programs are executed by the processor, the electronic device is enabled to perform the following steps: obtaining required training space, where the required training space is used to complete one or more training actions; determining, based on the training space, a training course and/or a training action that recommended to a user; and displaying a third interface, where the third interface includes a third window, and the third window is used to display the training course and/or the training action that is recommended to the user.

With reference to the sixth aspect, in a possible implementation, when the one or more programs are executed by the processor, the electronic device is enabled to perform the following steps: displaying a fourth interface before the third interface is displayed, where the fourth interface includes a fourth window used to enter the third window; detecting a first operation of the user in the fourth window, where the first operation is used to select a first option from a plurality of options; displaying a setting parameter of the first option in response to the first operation; detecting a second operation of the user in the fourth window, where the second operation is used to input the setting parameter of the first option; and displaying the third interface in response to the second operation.

According to a seventh aspect, this application provides an apparatus. The apparatus is included in an electronic device, and the apparatus has a function of implementing behavior of the electronic device in the foregoing aspects and the possible implementations of the foregoing aspects. The function may be implemented by hardware, or may be implemented by hardware executing corresponding software. The hardware or the software includes one or more modules or units corresponding to the foregoing function, for example, a display module or unit, a detection module or unit, or a processing module or unit.

According to an eighth aspect, this application provides an electronic device, including a touchscreen, where the touchscreen includes a touch-sensitive surface and a display; a camera; one or more processors; a memory; a plurality of applications; and one or more computer programs. The one or more computer programs are stored in the memory. The one or more computer programs include instructions. When the instructions are executed by the electronic device, the electronic device is enabled to perform the prompt method in any possible implementation of any one of the foregoing aspects.

According to a ninth aspect, this application provides an electronic device, including one or more processors and one or more memories. The one or more memories are coupled to the one or more processors. The one or more memories are configured to store computer program code, and the computer program code includes computer instructions. When the one or more processors execute the computer instructions, the electronic device is enabled to perform the prompt method in any possible implementation of any one of the foregoing aspects.

According to a tenth aspect, this application provides a computer storage medium, including computer instructions, where when the computer instructions are run on an electronic device, the electronic device is enabled to perform the prompt method in any possible implementation of any one of the foregoing aspects.

According to an eleventh aspect, this application provides a computer program product, where when the computer program product runs on an electronic device, the electronic device is enabled to perform the prompt method in any possible implementation of any one of the foregoing aspects.

DESCRIPTION OF EMBODIMENTS

Figure 1:
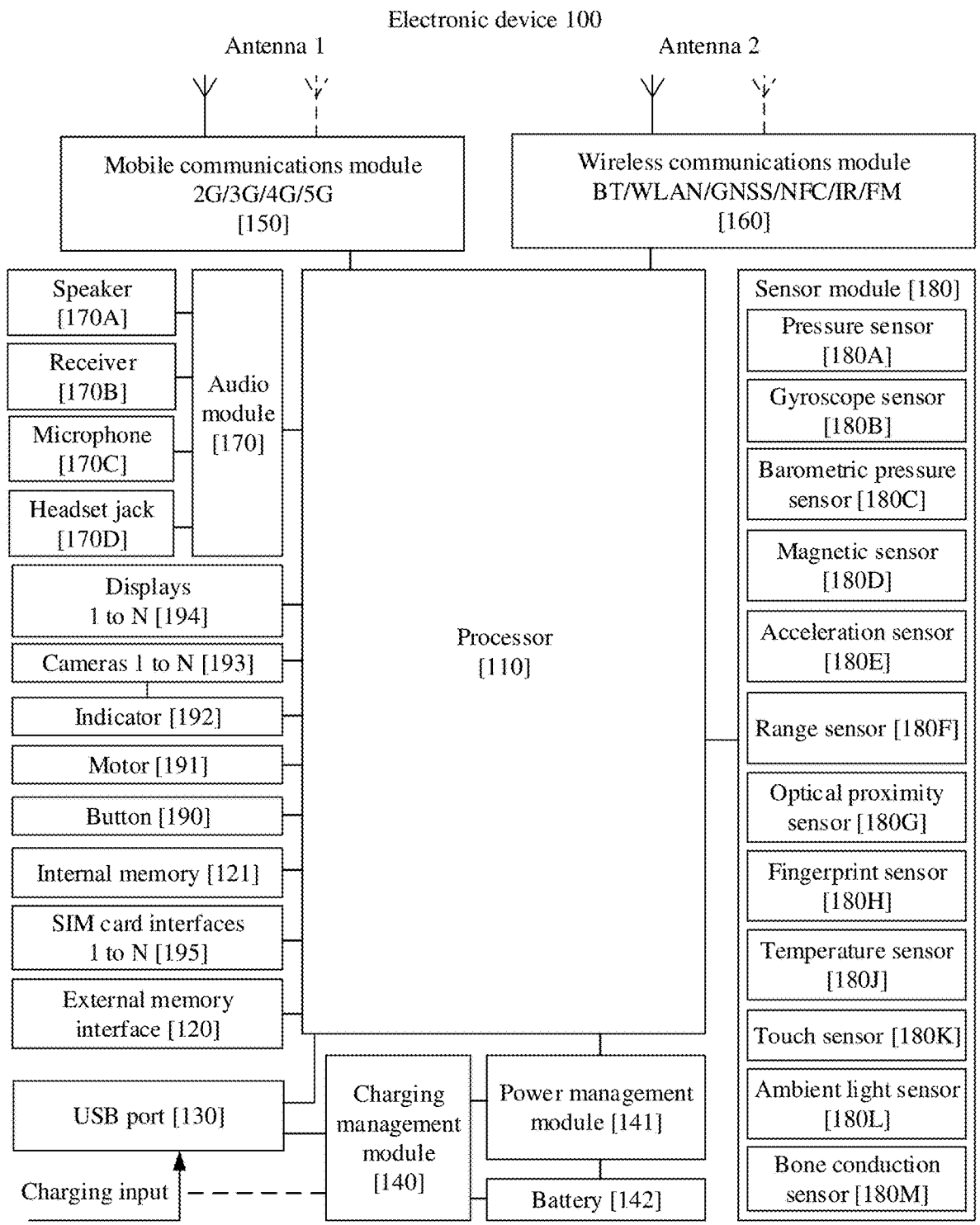
FIG. 1 is a schematic diagram of a hardware structure of an electronic device according to an embodiment of this application.

The following describes the technical solutions in this application with reference to the accompanying drawings.

It should be noted that, in descriptions of the embodiments of this application, "l" means "or" unless otherwise specified. For example, A/B may represent A or B. In this specification, "and/or" describes only an association relationship for describing associated objects and represents that three relationships may exist. For example, A and/or B may represent the following three cases: Only A exists, both A and B exist, and only B exists. In addition, in the descriptions of the embodiments of this application, "a plurality of" means two or more.

The following terms "first" and "second" are merely intended for a purpose of description, and shall not be understood as an indication or implication of relative importance or implicit indication of a quantity of indicated technical features. Therefore, a feature limited by "first" or "second" may explicitly or implicitly include one or more features. In the descriptions of the embodiments, unless otherwise specified, "a plurality of" means two or more.

As described in the background, in an intelligent fitness solution based on image processing, a training action of a user can be evaluated in a training process, so that the user can get professional guidance without leaving home. However, in the current intelligent fitness solution based on image processing, a location of the user in a training scenario cannot be provided for the user, or a location recommended to the user to stand conflicts with an object in a training scenario. In particular, in a scenario in which exercise space is limited, for example, a living room scenario or a dormitory scenario, the following problems exist: exercise space is insufficient, an obstruction affects action recognition accuracy, or an accident may occur in a training process. Consequently, the user possibly cannot normally perform training. Therefore, a prompt method for fitness training is required. In this way, a suitable training location may be provided for the user in the training scenario, so that the user can also normally perform training in a scenario in which exercise space is limited, and in particular, the user can normally take fitness exercise based on image processing.

The embodiments of this application provide a prompt method for fitness training, and the method may be applied to an electronic device. When a user expects to perform training in a scenario in which exercise space is limited, a suitable training location can be intelligently recommended to the user based on a training scenario in which the user is located and required training space, and the user does not need to select the training location, to ensure that training is normally performed.

The prompt method for fitness training provided in the embodiments of this application may be applied to an electronic device such as a mobile phone, a tablet computer, a wearable device, a vehicle-mounted device, an augmented reality (AR)/virtual reality (VR) device, a notebook computer, an ultra-mobile personal computer (UMPC), a netbook, or a personal digital assistant (PDA). A specific type of the electronic device is not limited in the embodiments of this application.

For example, FIG. 1 is a schematic diagram of a structure of an electronic device 100. The electronic device 100 may include a processor 110, an external memory interface 120, an internal memory 121, a universal serial bus (USB) port 130, a charging management module 140, a power management module 141, a battery 142, an antenna 1, an antenna 2, a mobile communications module 150, a wireless communications module 160, an audio module 170, a speaker 170A, a receiver 170B, a microphone 170C, a headset jack 170D, a sensor module 180, a button 190, a motor 191, an indicator 192, a camera 193, a display 194, a subscriber identification module (SIM) card interface 195, and the like. The sensor module 180 may include a pressure sensor 180A, a gyroscope sensor 180B, a barometric pressure sensor 180C, a magnetic sensor 180D, an acceleration sensor 180E, a range sensor 180F, an optical proximity sensor 180G, a fingerprint sensor 180H, a temperature sensor 180J, a touch sensor 180K, an ambient light sensor 180L, a bone conduction sensor 180M, and the like.

It may be understood that the structure shown in the embodiments of this application does not constitute a specific limitation on the electronic device 100. In some other embodiments of this application, the electronic device 100 may include more or fewer components than those shown in the figure, or some components may be combined, or some components may be split, or there may be a different component arrangement. The components shown in the figure may be implemented by hardware, software, or a combination of software and hardware.

The processor 110 may include one or more processing units. For example, the processor 110 may include an application processor (AP), a modem processor, a graphics processing unit (GPU), an image signal processor (ISP), a controller, a memory, a video codec, a digital signal processor (DSP), a baseband processor, and/or a neural-network processing unit (NPU). Different processing units may be independent components, or may be integrated into one or more processors.

The controller may be a nerve center and a command center of the electronic device 100. The controller may generate an operation control signal based on an instruction operation code and a time sequence signal, to control instruction reading and instruction execution.

A memory may be further disposed in the processor 110, and is configured to store instructions and data. In some embodiments, the memory in the processor 110 is a cache. The memory may store instructions or data just used or cyclically used by the processor 110. If the processor 110 needs to use the instructions or the data again, the processor 110 may directly invoke the instructions or the data from the memory. This avoids repeated access, reduces waiting time of the processor 110, and improves system efficiency.

In some embodiments, the processor 110 may include one or more interfaces. The interface may include an inter-integrated circuit (I2C) interface, an inter-integrated circuit sound (I2S) interface, a pulse code modulation (PCM) interface, a universal asynchronous receiver/transmitter (UART) interface, a mobile industry processor interface (MIPI), a general-purpose input/output (GPIO) interface, a subscriber identification module (SIM) interface, a universal serial bus (USB) port.

The I2C interface is a two-way synchronization serial bus, and includes a serial data line (SDA) and a serial clock line (SCL). In some embodiments, the processor 110 may include a plurality of groups of I2C buses. The processor 110 may be coupled to the touch sensor 180K, a charger, a flash, the camera 193, and the like through different I2C bus interfaces. For example, the processor 110 may be coupled to the touch sensor 180K through the I2C interface, so that the processor 110 communicates with the touch sensor 180K through the I2C bus interface, to implement a touch function of the electronic device 100.

The I2S interface may be configured to perform audio communication. In some embodiments, the processor 110 may include a plurality of groups of I2S buses. The processor 110 may be coupled to the audio module 170 through the I2S bus, to implement communication between the processor 110 and the audio module 170. In some embodiments, the audio module 170 may transmit an audio signal to the wireless communications module 160 through the I2S interface, to implement a function of answering a call through a Bluetooth headset.

The PCM interface may also be configured to perform audio communication, and sample, quantize, and code an analog signal. In some embodiments, the audio module 170 may be coupled to the wireless communications module 160 through a PCM bus interface. In some embodiments, the audio module 170 may also transmit an audio signal to the wireless communications module 160 through the PCM interface, to implement a function of answering a call through a Bluetooth headset. Both the I2S interface and the PCM interface may be configured to perform audio communication.

The UART interface is a universal serial data bus, and is configured to perform asynchronous communication. The bus may be a two-way communications bus. The bus converts to-be-transmitted data between serial communication and parallel communication. In some embodiments, the UART interface is usually configured to connect the processor 110 and the wireless communications module 160. For example, the processor 110 communicates with a Bluetooth module in the wireless communications module 160 through the UART interface, to implement a Bluetooth function. In some embodiments, the audio module 170 may transmit an audio signal to the wireless communications module 160 through the UART interface, to implement a function of playing music through a Bluetooth headset.

The MIPI interface may be configured to connect the processor 110 and a peripheral component such as the display 194 or the camera 193. The MIPI interface includes a camera serial interface (CSI), a display serial interface (DSI), or the like. In some embodiments, the processor 110 communicates with the camera 193 via the CSI interface, to implement a photography function of the electronic device 100. The processor 110 communicates with the display 194 through the DSI interface, to implement a display function of the electronic device 100.

The GPIO interface may be configured by software. The GPIO interface may be configured as a control signal or a data signal. In some embodiments, the GPIO interface may be configured to connect the processor 110 to the camera 193, the display 194, the wireless communications module 160, the audio module 170, the sensor module 180, or the like. The GPIO interface may alternatively be configured as the I2C interface, the I2S interface, the UART interface, the MIPI interface, or the like.

The USB port 130 is a port that conforms to a USB standard specification, and may be specifically a mini USB port, a micro USB port, a USB Type-C port, or the like. The USB port 130 may be configured to connect to a charger to charge the electronic device 100, or may be configured to transmit data between the electronic device 100 and a peripheral device, or may be configured to connect to a headset to play audio through the headset. Alternatively, the port may be configured to connect to another electronic device, for example, an AR device.

It may be understood that an interface connection relationship between the modules illustrated in this embodiment of this application is merely an example for description, and does not constitute a limitation on the structure of the electronic device 100. In some other embodiments of this application, the electronic device 100 may alternatively use an interface connection manner different from that in the foregoing embodiment, or a combination of a plurality of interface connection manners.

The charging management module 140 is configured to receive a charging input from the charger. The charger may be a wireless charger or a wired charger. In some embodiments of wired charging, the charging management module 140 may receive a charging input from a wired charger through the USB port 130. In some embodiments of wireless charging, the charging management module 140 may receive a wireless charging input by using a wireless charging coil of the electronic device 100. The charging management module 140 may further supply power to the electronic device by using the power management module 141 while charging the battery 142.

The power management module 141 is configured to connect to the battery 142, the charging management module 140, and the processor 110. The power management module 141 receives an input from the battery 142 and/or the charging management module 140, and supplies power to the processor 110, the internal memory 121, an external memory, the display 194, the camera 193, the wireless communications module 160, and the like. The power management module 141 may be further configured to monitor parameters such as a battery capacity, a battery cycle count, and a battery status of health (electric leakage and impedance). In some other embodiments, the power management module 141 may alternatively be disposed in the processor 110. In some other embodiments, the power management module 141 and the charging management module 140 may alternatively be disposed in a same device.

A wireless communication function of the electronic device 100 may be implemented by using the antenna 1, the antenna 2, the mobile communications module 150, the wireless communications module 160, the modem processor, the baseband processor, and the like.

The antenna 1 and the antenna 2 are configured to transmit and receive electromagnetic wave signals. Each antenna in the electronic device 100 may be configured to cover one or more communication frequency bands. Different antennas may further be multiplexed, to improve antenna utilization. For example, the antenna 1 may be multiplexed as a diversity antenna in a wireless local area network. In some other embodiments, the antenna may be used in combination with a tuning switch.

The mobile communications module 150 may provide a wireless communication solution applied to the electronic device 100 and including 2G, 3G, 4G, 5G, or the like. The mobile communications module 150 may include at least one filter, a switch, a power amplifier, a low noise amplifier (LNA), and the like. The mobile communications module 150 may receive an electromagnetic wave through the antenna 1, perform processing such as filtering and amplification on the received electromagnetic wave, and transmit a processed electromagnetic wave to the modem processor for demodulation. The mobile communications module 150 may further amplify a signal modulated by the modem processor, and convert the signal into an electromagnetic wave through the antenna 1 for transmission. In some embodiments, at least some function modules in the mobile communications module 150 may be disposed in the processor 110. In some embodiments, at least some function modules of the mobile communications module 150 and at least some modules of the processor 110 may be disposed in a same device.

The modem processor may include a modulator and a demodulator. The modulator is configured to modulate a to-be-sent low-frequency baseband signal into a medium/high-frequency signal. The demodulator is configured to demodulate a received electromagnetic wave signal into a low-frequency baseband signal. Then, the demodulator transmits the low-frequency baseband signal obtained through demodulation to the baseband processor for processing. After being processed by the baseband processor, the low-frequency baseband signal is transmitted to the application processor. The application processor outputs a sound signal by using an audio device (which is not limited to the speaker 170A, the receiver 170B, or the like), or displays an image or a video on the display 194. In some embodiments, the modem processor may be an independent component. In some other embodiments, the modem processor may be independent of the processor 110, and is disposed in a same device as the mobile communications module 150 or another function module.

The wireless communications module 160 may provide a wireless communication solution that is applied to the electronic device 100 and that includes a wireless local area network (WLAN) (for example, a wireless fidelity (Wi-Fi) network), Bluetooth (BT), a global navigation satellite system (GNSS), frequency modulation (FM), a near field communication (NFC) technology, an infrared (IR) technology, or the like. The wireless communications module 160 may be one or more components integrating at least one communications processing module. The wireless communications module 160 receives an electromagnetic wave through the antenna 2, performs frequency modulation and filtering processing on an electromagnetic wave signal, and sends a processed signal to the processor 110. The wireless communications module 160 may further receive a to-be-sent signal from the processor 110, perform frequency modulation and amplification on the signal, and convert a processed signal into an electromagnetic wave through the antenna 2 for transmission.

In some embodiments, the antenna 1 and the mobile communications module 150 in the electronic device 100 are coupled, and the antenna 2 and the wireless communications module 160 in the electronic device 100 are coupled, so that the electronic device 100 can communicate with a network and another device by using a wireless communications technology. The wireless communications technology may include a global system for mobile communications (GSM), general packet radio service (GPRS), code division multiple access (CDMA), wideband code division multiple access (WCDMA), time-division code division multiple access (TD-CDMA), long term evolution (LTE), BT, GNSS, WLAN, NFC, FM, and/or IR technology. The GNSS may include a global positioning system (GPS), a global navigation satellite system (GLONASS), a BeiDou navigation satellite system (BDS), a quasi-zenith satellite system (QZSS), and/or a satellite based augmentation system (SBAS).

The electronic device 100 implements a display function through the GPU, the display 194, the application processor, and the like. The GPU is a microprocessor for image processing, and is connected to the display 194 and the application processor. The GPU is configured to: perform mathematical and geometric calculation, and render an image. The processor 110 may include one or more GPUs that execute program instructions to generate or change display information.

For example, in the prompt method provided in the embodiments of this application, the GPU/NPU/CPU may run a user recognition algorithm such as a skeleton point recognition algorithm, to process an obtained image of a user and extract information about the user.

The display 194 is configured to display an image, a video, and the like. The display 194 includes a display panel. The display panel may be a liquid crystal display (LCD), an organic light-emitting diode (OLED), an active-matrix organic light-emitting diode (AMOLED), a flexible light-emitting diode (FLED), a mini-LED, a micro-LED, a micro-OLED, a quantum dot light-emitting diode (QLED), or the like. In some embodiments, the electronic device 100 may include one or N displays 194, where N is a positive integer greater than 1.

The electronic device 100 may implement a photography function through the ISP, the camera 193, the video codec, the GPU, the display 194, the application processor, and the like.

The ISP is configured to process data fed back by the camera 193. For example, during photography, a shutter is pressed, and light is transmitted to a photosensitive element of the camera through a lens. The photosensitive element of the camera converts an optical signal into an electrical signal, and transmits the electrical signal to the ISP for processing, to convert the electrical signal into a visible image. The ISP may further perform algorithm optimization on noise, brightness, and complexion of the image. The ISP may further optimize parameters such as exposure and a color temperature of a photographing scenario. In some embodiments, the ISP may be disposed in the camera 193.

The camera 193 is configured to capture a static image or a video. An optical image of an object is generated through the lens, and is projected onto a photosensitive element. The photosensitive element may be a charge-coupled device (CCD) or a complementary metal-oxide-semiconductor (CMOS) phototransistor. The photosensitive element converts an optical signal into an electrical signal, and then transmits the electrical signal to the ISP to convert the electrical signal into a digital image signal. The ISP outputs the digital image signal to the DSP for processing. The DSP converts the digital image signal into a standard image signal in an RGB format, a YUV format, or the like. In some embodiments, the electronic device 100 may include one or N cameras 193, where N is a positive integer greater than 1.

For example, in the prompt method provided in the embodiments of this application, the camera may collect images of the user and a training scenario, and display the collected images in a viewfinder frame or a preview interface. The photosensitive element converts a collected optical signal into an electrical signal, and then transmits the electrical signal to the ISP to convert the electrical signal into a digital image signal. The ISP outputs the digital image signal to the DSP for related image processing.

The digital signal processor is configured to process a digital signal, and may further process another digital signal in addition to the digital image signal. For example, when the electronic device 100 selects a frequency, the digital signal processor is configured to perform Fourier transform and the like on frequency energy.

The video codec is configured to compress or decompress a digital video. The electronic device 100 may support one or more video codecs. In this way, the electronic device 100 can play or record videos in a plurality of coding formats, for example, moving picture experts group (MPEG)-1, MPEG-2, MPEG-3, and MPEG-4.

The NPU is a neural-network (NN) computing processor. With reference to a structure of a biological neural network, for example, with reference to a transfer mode between neurons of a human brain, the NPU quickly processes input information, and can further continuously perform self-learning. Applications such as intelligent cognition of the electronic device 100 may be implemented through the NPU, for example, image recognition, facial recognition, speech recognition, and text understanding.

For example, in the prompt method provided in the embodiments of this application, the NPU may perform action matching, gesture recognition, voice recognition, and the like in a training start confirmation process after the user moves to a recommended training location.

The external memory interface 120 may be configured to connect to an external memory card such as a micro SD card, to extend a storage capability of the electronic device 100. The external memory card communicates with the processor 110 through the external memory interface 120, to implement a data storage function. For example, files such as music and a video are stored in the external memory card.

The internal memory 121 may be configured to store computer-executable program code. The executable program code includes instructions. The processor 110 runs the instructions stored in the internal memory 121, to perform various function applications of the electronic device 100 and data processing. The internal memory 121 may include a program storage area and a data storage area. The program storage area may store an operating system, an application required by at least one function (for example, a sound playing function and an image playing function), and the like. The data storage area may store data (for example, audio data and an address book) and the like created when the electronic device 100 is used. In addition, the internal memory 121 may include a high-speed random access memory, and may further include a nonvolatile memory such as at least one magnetic disk storage device, a flash memory device, or a universal flash storage (UFS).

The electronic device 100 may implement audio functions such as music playing and recording by using the audio module 170, the speaker 170A, the receiver 170B, the microphone 170C, the headset jack 170D, the application processor, and the like.

The audio module 170 is configured to convert digital audio information into an analog audio signal for output, and is also configured to convert an analog audio input into a digital audio signal. The audio module 170 may be further configured to encode and decode audio signals. In some embodiments, the audio module 170 may be disposed in the processor 110, or some function modules of the audio module 170 are disposed in the processor 110.

The speaker 170A, also referred to as a "horn", is configured to convert an audio electrical signal into a sound signal. The user of the electronic device 100 may be used to listen to music, play voice or answer a call in a hands-free mode by using the speaker 170A.

For example, in the prompt method provided in the embodiments of this application, the speaker may play voice used to prompt the user to move to the recommended training location.

The receiver 170B, also referred to as an "earpiece", is configured to convert an audio electrical signal into a sound signal. When the user of the electronic device 100 is used to answer a call or listen to a voice message, the receiver 170B may be placed near a human ear to listen to a voice.

The microphone 170C, also referred to as a "mike" or "mic", is configured to convert a sound signal into an electrical signal. When making a call or sending a voice message, the user may make a sound near the microphone 170C through the mouth, to enter a sound signal to the microphone 170C. At least one microphone 170C may be disposed in the electronic device 100. In some other embodiments, two microphones 170C may be disposed in the electronic device 100, to implement a noise reduction function in addition to a function of recording a sound signal. In some other embodiments, three, four, or more microphones 170C may be alternatively disposed in the electronic device 100, to collect a sound signal, implement noise reduction, and identify a sound source, so as to implement a directional recording function and the like.

The headset jack 170D is configured to connect to a wired headset. The headset jack 170D may be the USB port 130, or may be a 3.5 mm open mobile terminal platform (OMTP) standard interface or a cellular telecommunications industry association of the USA (CTIA) standard interface.

The pressure sensor 180A is configured to sense a pressure signal, and can convert the pressure signal into an electrical signal. In some embodiments, the pressure sensor 180A may be disposed on the display 194. There are many types of pressure sensors 180A, such as a resistive pressure sensor, an inductive pressure sensor, and a capacitive pressure sensor. The capacitive pressure sensor may include at least two parallel plates made of conductive materials. When force is applied to the pressure sensor 180A, a capacitance between electrodes changes. The electronic device 100 determines pressure strength based on a change of the capacitance. When a touch operation is performed on the display 194, the electronic device 100 detects intensity of the touch operation by using the pressure sensor 180A. The electronic device 100 may calculate a touch location based on a detection signal of the pressure sensor 180A. In some embodiments, touch operations that are performed at a same touch location but have different touch operation intensity may correspond to different operation instructions. For example, when a touch operation whose touch operation intensity is less than a first pressure threshold is performed on an icon of Messages, an instruction for viewing an SMS message is executed. When a touch operation whose touch operation intensity is greater than or equal to the first pressure threshold is performed on the icon of Messages, an instruction for creating a new SMS message is executed.

The gyroscope sensor 180B may be configured to determine a moving posture of the electronic device 100. In some embodiments, angular velocities of the electronic device 100 around three axes (namely, axes x, y, and z) may be determined by using the gyroscope sensor 180B. The gyroscope sensor 180B may be configured to implement image stabilization during photography. For example, when the shutter is pressed, the gyroscope sensor 180B detects an angle through which the electronic device 100 moves, and calculates, based on the angle, a distance for which a lens module needs to compensate, so that the lens cancels the shake of the electronic device 100 through reverse motion, thereby implementing the image stabilization. The gyroscope sensor 180B may be further used in a navigation scenario and a motion-sensing game scenario.

The barometric pressure sensor 180C is configured to measure barometric pressure. In some embodiments, the electronic device 100 calculates an altitude by using a barometric pressure value measured by the barometric pressure sensor 180C, to assist in positioning and navigation.

The magnetic sensor 180D includes a Hall effect sensor. The electronic device 100 may detect opening and closing of a flip cover by using the magnetic sensor 180D. In some embodiments, when the electronic device 100 is a clamshell phone, the electronic device 100 may detect opening and closing of a clamshell by using the magnetic sensor 180D. Further, a feature such as automatic unlocking upon opening of the flip cover is set based on a detected opening or closing state of the leather case or a detected opening or closing state of the flip cover.

The acceleration sensor 180E may detect magnitude of acceleration of the electronic device 100 in various directions (usually on three axes). When the electronic device 100 is still, magnitude and a direction of gravity may be detected. The acceleration sensor may be further configured to recognize a posture of the electronic device, and is used in an application such as switching between a landscape mode and a portrait mode or a pedometer.

The range sensor 180F is configured to measure a distance. The electronic device 100 may measure a distance in an infrared or a laser manner. In some embodiments, in a photography scenario, the electronic device 100 may measure a distance by using the range sensor 180F, to implement quick focusing.

The optical proximity sensor 180G may include, for example, a light-emitting diode (LED) and an optical detector such as a photodiode. The light-emitting diode may be an infrared light-emitting diode. The electronic device 100 emits infrared light by using the light-emitting diode. The electronic device 100 detects, by using the photodiode, infrared reflected light from a nearby object. When sufficient reflected light is detected, it may be determined that there is an object near the electronic device 100. When detecting insufficient reflected light, the electronic device 100 may determine that there is no object near the electronic device 100. The electronic device 100 may detect, by using the optical proximity sensor 180G, that the user holds the electronic device 100 close to an ear for a call, to automatically perform screen-off to save power. The optical proximity sensor 180G may also be used in a smart cover mode or a pocket mode to automatically perform screen unlocking or locking.

The ambient light sensor 180L is configured to sense ambient light brightness. The electronic device 100 may adaptively adjust brightness of the display 194 based on the sensed ambient light brightness. The ambient light sensor 180L may also be configured to automatically adjust white balance during photography. The ambient light sensor 180L may further cooperate with the optical proximity sensor 180G to detect whether the electronic device 100 is in a pocket, to prevent an accidental touch.

The fingerprint sensor 180H is configured to collect a fingerprint. The electronic device 100 may use a feature of the collected fingerprint to implement fingerprint-based unlocking, application lock access, fingerprint-based photography, fingerprint-based call answering, and the like.

The temperature sensor 180J is configured to detect a temperature. In some embodiments, the electronic device 100 executes a temperature processing policy based on the temperature detected by the temperature sensor 180J. For example, when the temperature reported by the temperature sensor 180J exceeds a threshold, the electronic device 100 degrades performance of a processor near the temperature sensor 180J, to reduce power consumption and implement thermal protection. In some other embodiments, when the temperature is less than another threshold, the electronic device 100 heats up the battery 142, to avoid abnormal shutdown of the electronic device 100 due to a low temperature. In some other embodiments, when the temperature is lower than still another threshold, the electronic device 100 boosts an output voltage of the battery 142 to avoid abnormal shutdown caused by a low temperature.

The touch sensor 180K is also referred to as a "touch panel". The touch sensor 180K may be disposed on the display 194, and the touch sensor 180K and the display 194 form a touchscreen, which is also referred to as a "touch screen". The touch sensor 180K is configured to detect a touch operation performed on or near the touch sensor 180K. The touch sensor may transfer the detected touch operation to the application processor, to determine a type of a touch event. A visual output related to the touch operation may be provided on the display 194. In some other embodiments, the touch sensor 180K may alternatively be disposed on a surface of the electronic device 100 at a position different from that of the display 194.

The bone conduction sensor 180M may obtain a vibration signal. In some embodiments, the bone conduction sensor 180M may obtain a vibration signal of a vibration bone of a human vocal-cord. The bone conduction sensor 180M may also be able to detect a human pulse, and receive a blood pressure signal. In some embodiments, the bone conduction sensor 180M may also be disposed in the headset, to form a bone conduction headset. The audio module 170 may obtain a speech signal through parsing based on the vibration signal that is of the vibration bone of the vocal-cord and that is obtained by the bone conduction sensor 180M, to implement a speech function. The application processor may parse heart rate information based on the blood pressure signal obtained by the bone conduction sensor 180M, to implement a heart rate detection function.

The button 190 includes a power button, a volume button, and the like. The button 190 may be a mechanical button, or may be a touch button. The electronic device 100 may receive a button input, and generate a button signal input related to user settings and function control of the electronic device 100.

The motor 191 may generate a vibration prompt. The motor 191 may be configured to produce an incoming call vibration prompt and a touch vibration feedback. For example, touch operations performed on different applications (for example, photography and audio playing) may correspond to different vibration feedback effects. For touch operations performed in different areas of the display 194, the motor 191 may also correspond to different vibration feedback effects. Different application scenarios (for example, a time reminder, information receiving, an alarm clock, and a game) may also correspond to different vibration feedback effects. A touch vibration feedback effect may be further customized The indicator 192 may be an indicator light, and may be configured to indicate a charging status and a power change, or may be configured to indicate a message, a missed call, a notification, and the like.

The SIM card interface 195 is configured to connect to a SIM card. The SIM card may be inserted into the SIM card interface 195 or removed from the SIM card interface 195, to implement contact with or separation from the electronic device 100. The electronic device 100 may support one or N SIM card interfaces, where N is a positive integer greater than 1. The SIM card interface 195 may support a nano SIM card, a micro SIM card, a SIM card, and the like. A plurality of cards may be simultaneously inserted into a same SIM card interface 195. The plurality of cards may be of a same type or of different types. The SIM card interface 195 is also compatible with different types of SIM cards. The SIM card interface 195 is also compatible with an external memory card. The electronic device 100 interacts with a network by using the SIM card, to implement functions such as calling and data communication. In some embodiments, the electronic device 100 uses an eSIM, namely, an embedded SIM card. The eSIM card may be embedded in the electronic device 100, and cannot be separated from the electronic device 100.

A software system of the electronic device 100 may use a layered architecture, an event-driven architecture, a micro-kernel architecture, a micro service architecture, or a cloud architecture. In an embodiment of this application, an Android system with a layered architecture is used as an example to describe a software structure of the electronic device 100.

Figure 2:
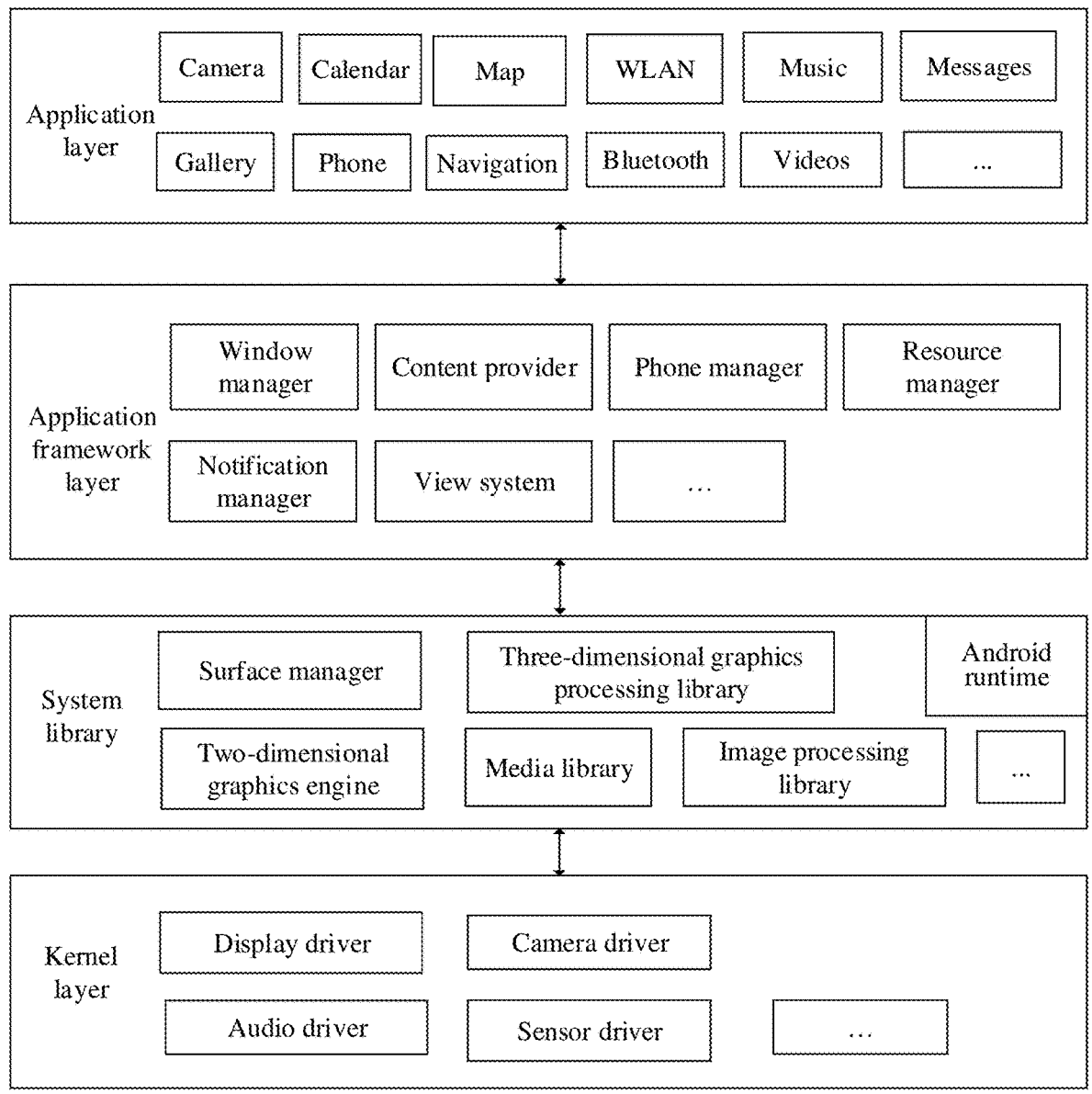
FIG. 2 is a schematic diagram of a software structure of an electronic device according to an embodiment of this application.

FIG. 2 is a block diagram of the software structure of the electronic device 100 according to an embodiment of this application. In a layered architecture, software is divided into several layers, and each layer has a clear role and task. The layers communicate with each other through a software interface. In some embodiments, the Android system is divided into four layers: an application layer, an application framework layer, an Android runtime and system library, and a kernel layer from top to bottom. The application layer may include a series of application packages.

As shown in FIG. 2, the application packages may include applications such as "camera", "gallery", "calendar", "phone", "map", "navigation", "WLAN", "Bluetooth", "music", "videos", and "messages".

The application framework layer provides an application programming interface (API) and a programming framework for an application at the application layer. The application framework layer includes some predefined functions.

For example, in this application, a user identification function or algorithm, an image processing algorithm, and the like may all be included in the application framework layer.

As shown in FIG. 2, the application framework layer may include a window manager, a content provider, a view system, a phone manager, a resource manager, a notification manager, and the like.

The window manager is configured to manage a window program. The window manager may obtain a size of a display, determine whether there is a status bar, perform screen locking, take a screenshot, and the like.

The content provider is configured to store and obtain data, and enable the data to be accessible by an application. The data may include a video, an image, audio, calls that are made and received, a browsing history and a bookmark, an address book, and the like.

For example, in this application, the content provider may obtain, in real time, an image collected in the viewfinder frame or the preview interface, and display a processed image in the viewfinder frame or the preview interface.

The view system includes visual controls, such as a control for displaying a text and a control for displaying an image. The view system may be configured to construct an application. A display interface may include one or more views. For example, a display interface including an SMS message notification icon may include a text display view and an image display view.

For example, in this application, content such as "there is an obstruction in a current environment" that is displayed in a training interface may be displayed by the view system by receiving an indication of the processor, to remind the user whether a current location is suitable to perform training.

The phone manager is configured to provide a communication function of the electronic device 100, for example, management of a call status (including answering, declining, or the like).

The resource manager provides various resources for an application, such as a localized character string, an icon, a picture, a layout file, and a video file.

The notification manager enables an application to display notification information in the status bar, and may be used to transmit a notification-type message. The displayed information may automatically disappear after a short pause without user interaction. For example, the notification manager is configured to notify download completion, give a message notification, and the like. The notification manager may alternatively be a notification that appears in a top status bar of the system in a form of a graph or a scroll bar text, for example, a notification of an application that is run in the background, or may be a notification that appears on the screen in a form of a dialog window. For example, text information is prompted in the status bar, a prompt tone is produced, the electronic device vibrates, or an indicator light blinks.

The Android runtime includes a kernel library and a virtual machine. The Android runtime is responsible for scheduling and management of the Android system.

The kernel library includes two parts: a function that needs to be invoked in Java language and a kernel library of Android.

The application layer and the application framework layer are run on the virtual machine. The virtual machine executes Java files of the application layer and the application framework layer as binary files. The virtual machine is configured to perform functions such as object lifecycle management, stack management, thread management, security and exception management, and garbage collection.

The system library may include a plurality of function modules, for example, a surface manager, a media library, a three-dimensional graphics processing library (for example, an open graphics library for embedded systems (OpenGL ES), and a 2D graphics engine (for example, a Skia database (SGL)).

The surface manager is configured to manage a display subsystem and provide fusion of 2D and 3D layers for a plurality of applications.

The media library supports playback and recording in a plurality of commonly used audio and video formats, static image files, and the like. The media library may support a plurality of audio and video coding formats such as MPEG-4, H.264, MP3, AAC, AMR, JPG, and PNG.

The three-dimensional graphics processing library is configured to implement three-dimensional graphics drawing, image rendering, composition, layer processing, and the like.

The 2D graphics engine is a drawing engine for 2D drawing.

The kernel layer is a layer between hardware and software. The kernel layer includes at least a display driver, a camera driver, an audio driver, and a sensor driver.

For ease of understanding, with reference to the accompanying drawings and an application scenario, the prompt method for fitness training provided in the embodiments of this application is specifically described in the following embodiments of this application by using an electronic device with the structures shown in FIG. 1 and FIG. 2 as an example.

It should be noted that FIG. 1 shows merely an example of the electronic device, and this is not particularly limited in this application. This application may be applied to an intelligent device such as a mobile phone or a tablet computer. This is not limited in this application. In descriptions of the embodiments of this application, a mobile phone is used as an example for description.

To enable a user to normally perform training in a scenario in which exercise space is limited, a suitable training location is recommended to the user based on a training scenario and required training space. Therefore, the user can also normally perform training when the exercise space is limited, for example, when there is an obstruction or the site is insufficient.

For ease of understanding of this application, some human-computer interaction embodiments in this application are first described.

FIG. 3(a) to FIG. 3(d) are schematic diagrams of an example of entering a graphical user interface (GUI) of an application program according to an embodiment of this application. In this application, the mobile phone is used as the electronic device to describe in detail the prompt method provided in this application.

Figure 3A:
FIG. 3(a) to FIG. 3(d) are schematic diagrams of entering a graphical user interface of an application program according to an embodiment of this application.
Figure 3B:
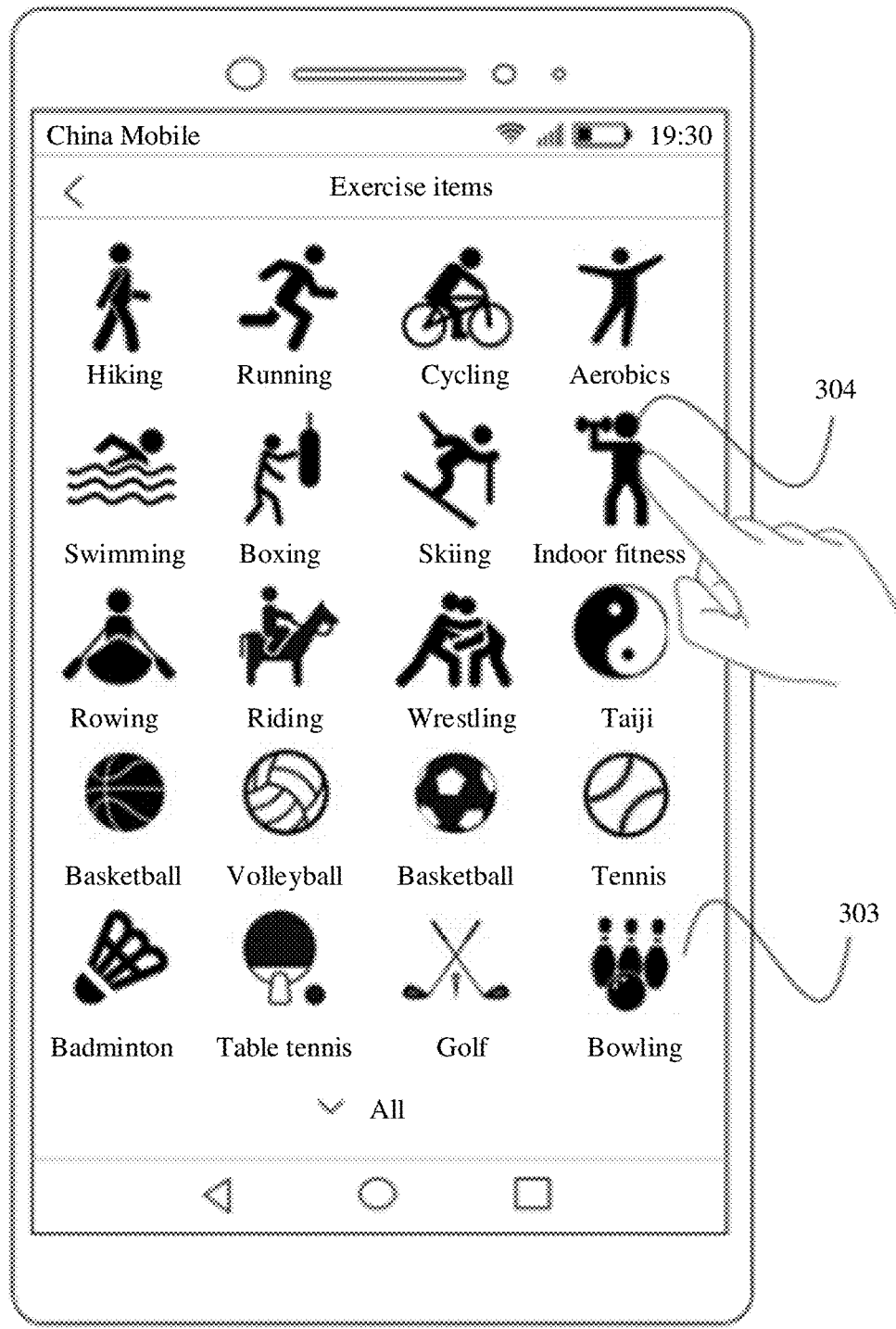
Figure 3C:
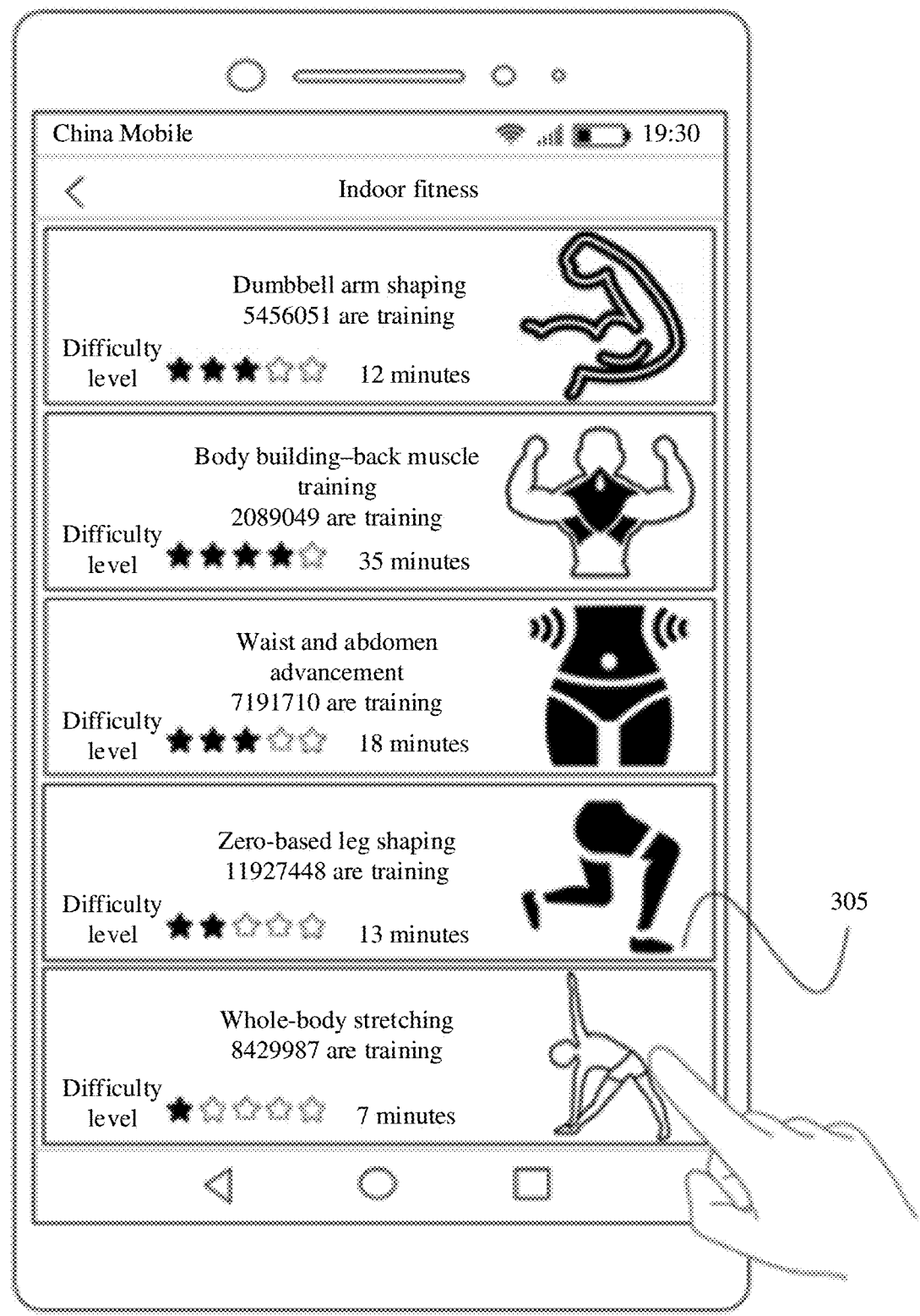
Figure 3D:
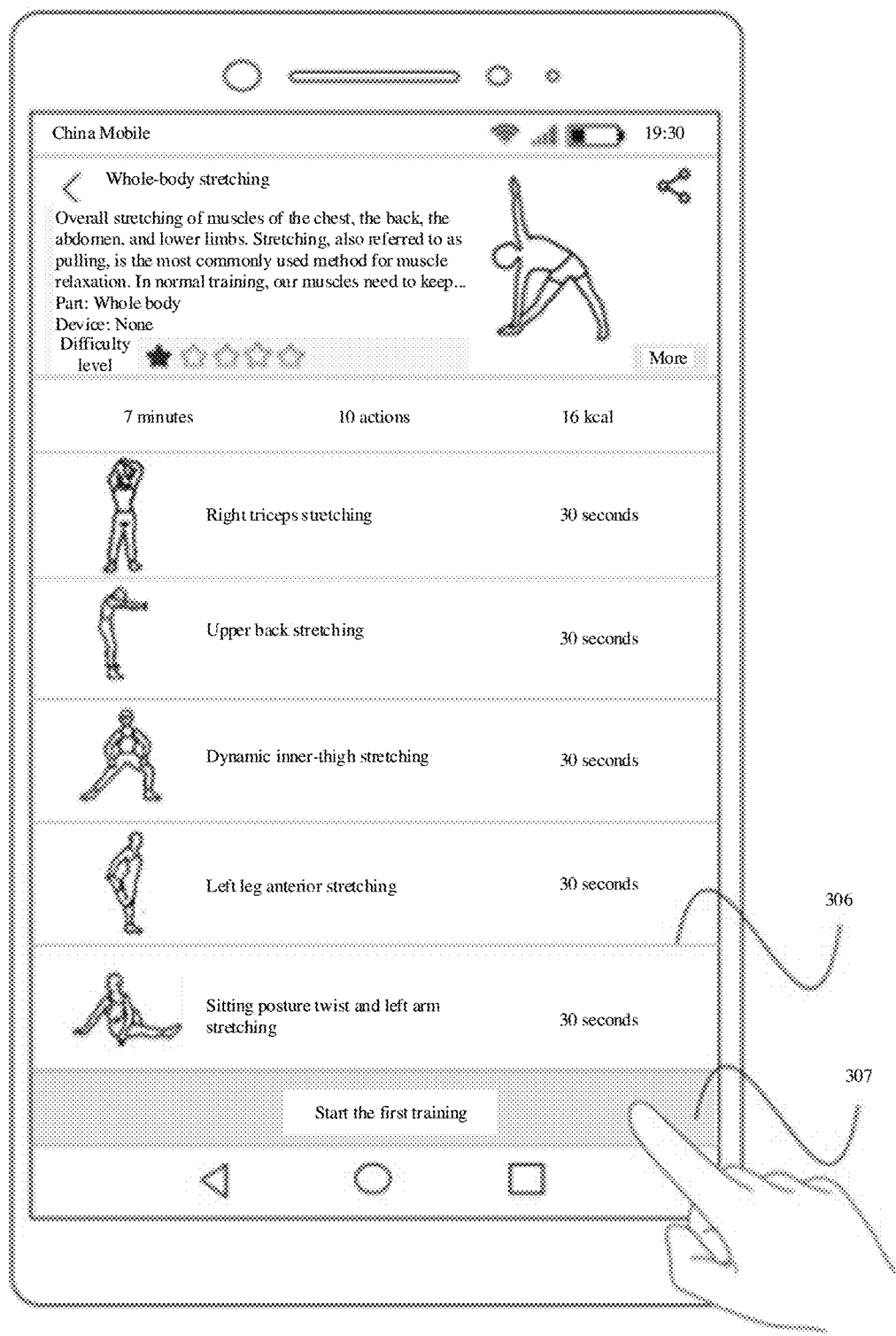

FIG. 3(a) shows current interface content 301 that is possibly displayed by a screen display system of the mobile phone in an unlock mode of the mobile phone. The interface content 301 is a home screen of the mobile phone. A plurality of third-party applications (App) are displayed in the interface content 301, for example, Alipay, Task card store, Weibo, Gallery, WeChat, Settings, Camera, and Fitness. It should be understood that the interface content 301 may further include more other applications. This is not limited to the applications displayed.

In some embodiments, the home screen 301 of the mobile phone imposes no limitation. The interface content displayed on the mobile phone may be interface content displayed after the mobile phone responds to an input operation of the user, and the operation of the user may include an operation that the user taps icons of some application programs in the home screen displayed on the mobile phone, or an operation that the user taps an icon in the interface content of an application program displayed on the mobile phone. For example, after the user taps an application program such as WeChat, Alipay, Task card store, Weibo, Gallery, Settings, and Fitness that are displayed on the home screen 301 of the mobile phone, a display interface corresponding to each application program is displayed.

For example, after detecting an operation that the user taps an icon 302 of the Fitness application on the home screen 301, the mobile phone may start the Fitness application, for example, may display an interface shown in FIG. 3(*b*). The interface may be referred to as an exercise item selection interface 303. The exercise item selection interface 303 may include icons of a plurality of exercise items such as hiking, running, cycling, aerobics, swimming, boxing, skiing, indoor fitness, and rowing. It should be understood that the exercise item selection interface 303 may include icons of more, fewer, or other exercise items. This is not limited to those applications mentioned.

Further, after the user taps the icons that are of the exercise items and that are displayed in the exercise item selection interface 303, a graphic user interface corresponding to each exercise item is displayed. For example, after detecting that the user taps an icon 304 of Indoor fitness in the exercise item selection interface 303, the mobile phone may enter a display interface corresponding to Indoor fitness, for example, it may display an interface shown in FIG. 3(*c*). The interface may be referred to as a training plan selection interface 305. The training plan selection interface 305 may include a plurality of training plans, for example, "Dumbbell arm shaping", "Body building—back muscle training", "Waist and abdomen advancement", "Zero-based leg shaping", and "Whole-body stretching". The plurality of training plans displayed in the training plan selection interface 305 may be training for parts such as an arm, a back, a waist, an abdomen, a leg, a shoulder, a chest, a neck, and a whole body. It should be understood that the training plan selection interface 305 may include more, fewer, or other training plans. This is not limited to those training plans mentioned. Optionally, the user may use a finger to swipe on a touchscreen of the mobile phone. In response to the swipe operation of the user, the mobile phone may load more training plans and display the training plans in the training plan selection interface 305.

Further, after the user selects one of the training plans displayed in the training plan selection interface 305, a graphic user interface corresponding to the selected training plan is displayed. For example, after detecting that the user taps the training plan "whole-body stretching" in the training plan selection interface 305, the mobile phone may enter a corresponding display interface, for example, may display an interface shown in FIG. 3(*d*). The interface may be referred to as a training start interface 306. The training start interface 306 may include descriptions of the training plan, for example, a training part, whether a device is required, a difficulty level, duration, to-be-consumed energy, and a training action. It should be understood that the training start interface 306 may include more, less, or other display content. The training start interface 306 may further include an icon 307, used to start a training process. After detecting that the user taps the icon 307, the mobile phone may display or play, on the touchscreen, a target course video corresponding to the training plan selected by the user. It should be understood that in some embodiments, icon 307 could also be a button 307.

In recent years, the number of fitness enthusiasts has gradually increased. For people who have no time to go to a gym, intelligent fitness based on image processing may enable the user to enjoy professional guidance without leaving home. Specifically, in a training process of the user, the mobile phone may recognize a training action of the user, and then evaluate the training action of the user according to an image algorithm, for example, evaluate completion quality of the user based on a key indicator of the training action, and point out an incorrect action and an improvement manner, to provide guidance for the user, so that the user can exercise scientifically.

Figure 4A:
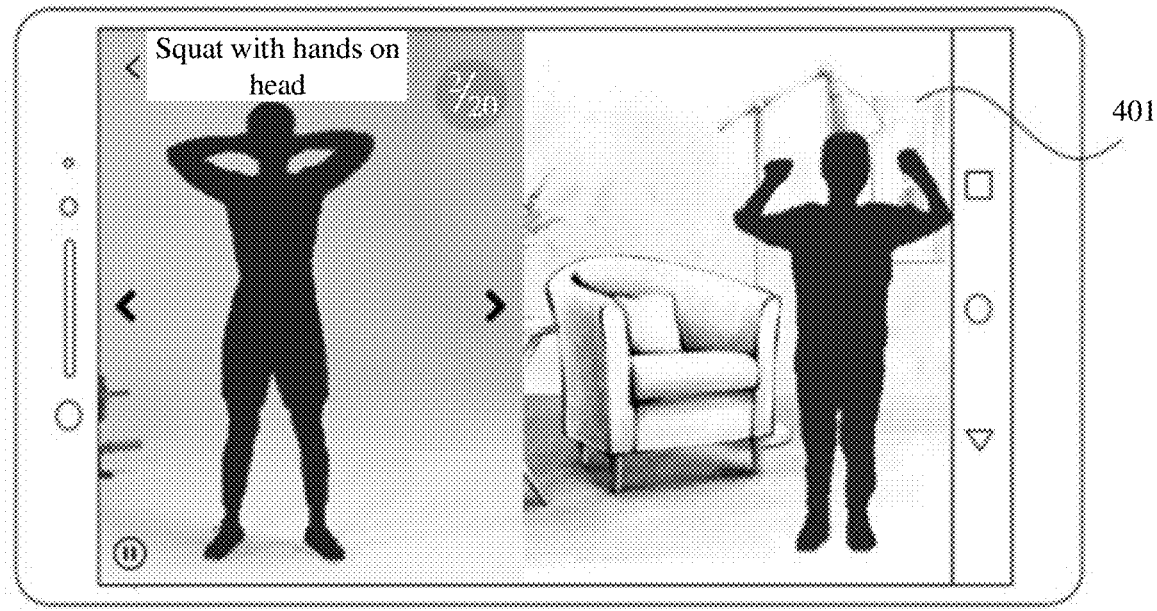
FIG. 4(a) and FIG. 4(b) are schematic diagrams of a graphical user interface in an existing fitness solution based on image processing.
Figure 4B:
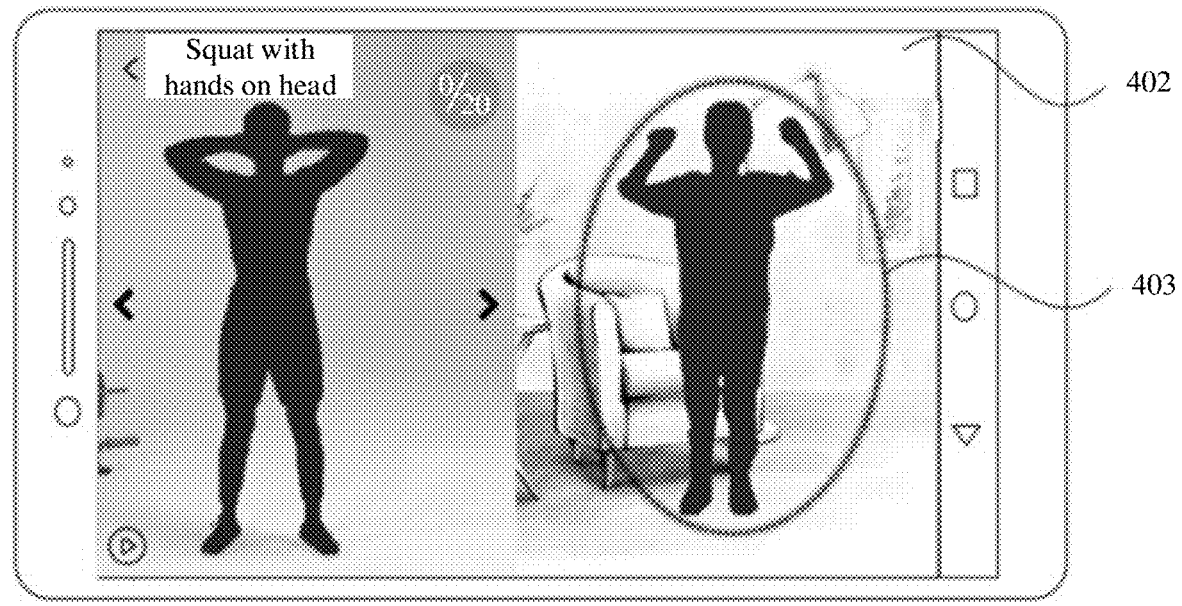

FIG. 4(*a*) shows interface content in a fitness solution based on image processing. An interface 401 shown in FIG. 4(*a*) includes a target course video and a viewfinder frame. The target course video may be a recorded coach video. The user locally downloads the target course video in advance, and performs a play, pause, or close operation on the target course video when the mobile phone detects an instruction or a signal or responds to an operation of the user. The viewfinder frame is used to obtain a view or recorded preview image, and display the preview image in real time, for example, preview images that are of a training scenario and the user and that are shown in FIG. 4(*a*). In the fitness solution based on image processing shown in FIG. 4(*a*), when detecting that the user appears in the viewfinder frame, the mobile phone performs a play operation on the target course video (that is, the user starts training), and may further play sound in the target course video by using a speaker, to notify the user of their training progress. When the user performs training in a scenario in which exercise space is limited, for example, a living room scenario or a dormitory scenario, due to a size of the space and an obstruction that may appear, the user cannot perform training well. For example, the obstruction affects accuracy of recognizing an action according to an algorithm, and further affects accuracy of guidance provided for the user. Alternatively, if an action in a large range exists in the training process, an accident may occur or the user needs to temporarily interrupt training. FIG. 4(*b*) shows interface content in another fitness solution based on image processing. An interface 402 shown in FIG. 4(*b*) includes the target course video and the viewfinder frame. In the fitness solution based on image processing shown in FIG. 4(*b*), the mobile phone may prompt the user with a location to stand in a preview image displayed in the viewfinder frame. For example, the mobile phone displays a recommended-location box 403 in the preview image. Only when detecting that the user is in the recommended-location box 403, the mobile phone performs a play operation on the target course video (that is, the user starts training). When the user is not in the recommended-location box 403, training cannot be started. Similarly, when the user performs training in a scenario in which exercise space is limited, for example, a living room scenario or a dormitory scenario, due to a size of the space and an obstruction that may appear, the user cannot stand at a recommended location because an article such as a sofa, a desk lamp, or a tea table may appear in the recommended-location box 403, or an accident may occur in the training process because space recommended by the mobile phone is insufficient. Consequently, the user cannot normally perform training.

Therefore, this application provides a prompt method for fitness training, so that in a scenario in which exercise space is limited, a suitable training location can be recommended to the user based on a training scenario and required training space. Therefore, the user can normally perform training when the exercise space is limited, for example, when there is an obstruction or the site is insufficient.

Figure 5A:
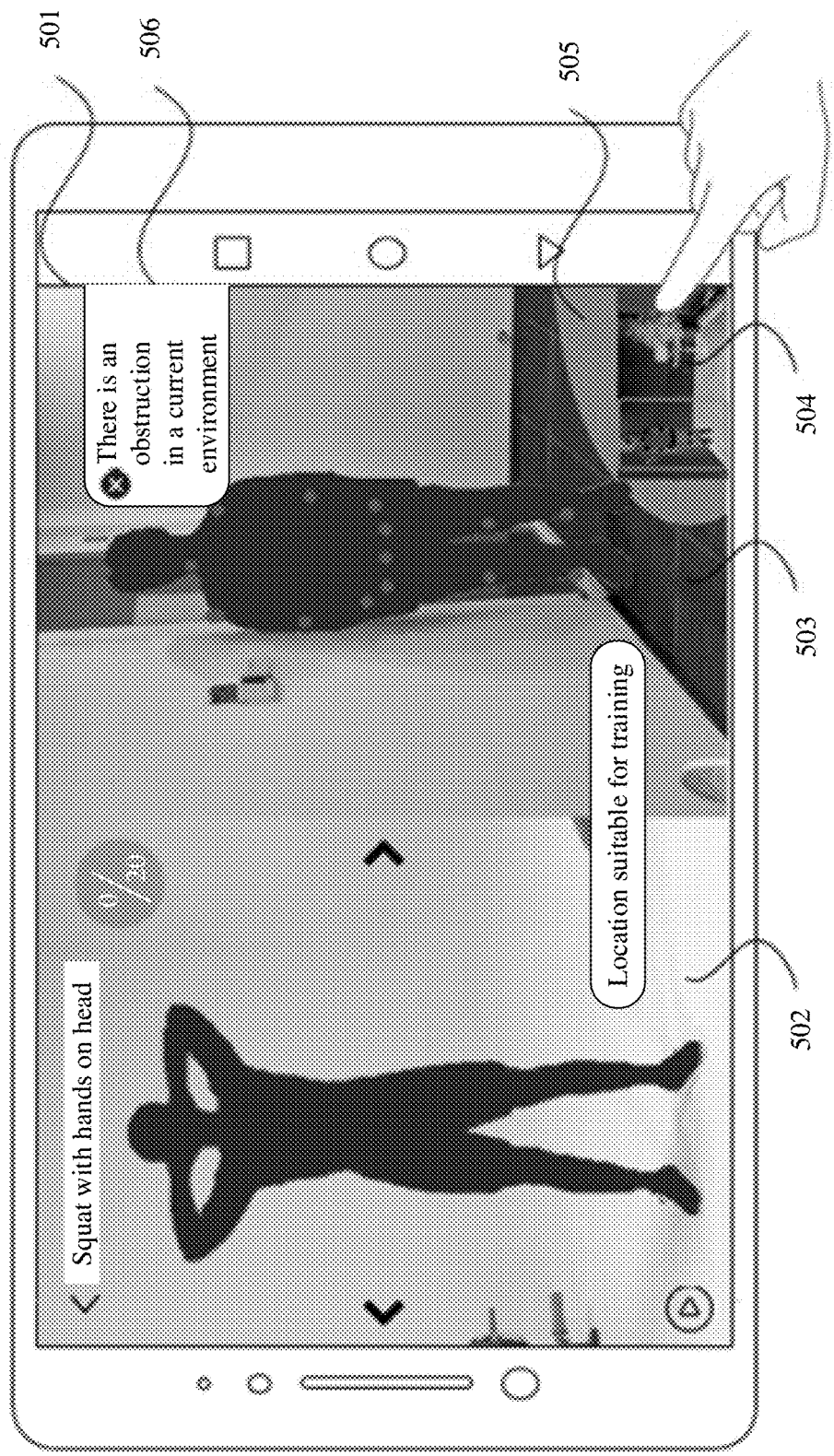
FIG. 5(a) to FIG. 5(f) are schematic diagrams of a graphical user interface in a prompt method according to an embodiment of this application.

FIG. 5(a) to FIG. 5(f) are schematic diagrams of a graphical user interface in a prompt method according to an embodiment of this application. As described above, after detecting that the user taps the icon 307, the mobile phone may enter a corresponding display interface, for example, may display an interface shown in FIG. 5(a). The interface may be referred to as a training interface 501. The training interface 501 may include a target course video interface content 502, a viewfinder frame 503, and a camera field of view 504. A target course video is displayed in the target course video interface content 502. The target course video may be a recorded coach video, and is locally downloaded or buffered by the user in advance (for example, downloaded or buffered to an external memory card or an internal memory of the mobile phone). For example, after detecting that the user taps the icon 307, the mobile phone automatically performs a downloading operation on the target course video. The viewfinder frame 503 is used to obtain a view or recorded preview image, may display the preview image in real time, and therefore may also be referred to as a preview interface. A framing range of the viewfinder frame 503 is displayed in the preview interface. As shown in FIG. 5(a), preview images of a training scenario and the user are displayed in the viewfinder frame 503. Due to a display range of the touchscreen, the framing range displayed in the viewfinder frame 503 may be less than the camera field of view 504. The camera field of view 504 is used to display, in real time, a picture obtained by the camera and a location of the user in the acquired picture. Processed interface content may be displayed in the camera field of view 504. The mobile phone may obtain a video frame of a current picture acquired by the camera, process the video frame of the current picture according to the image algorithm, and then display the processed video frame in the camera field of view 504. For example, only an approximate shape instead of specific details of the user, a wall, a floor, a plant, or the like may be displayed in the camera field of view 504 in FIG. 5(a).

Figure 5B:
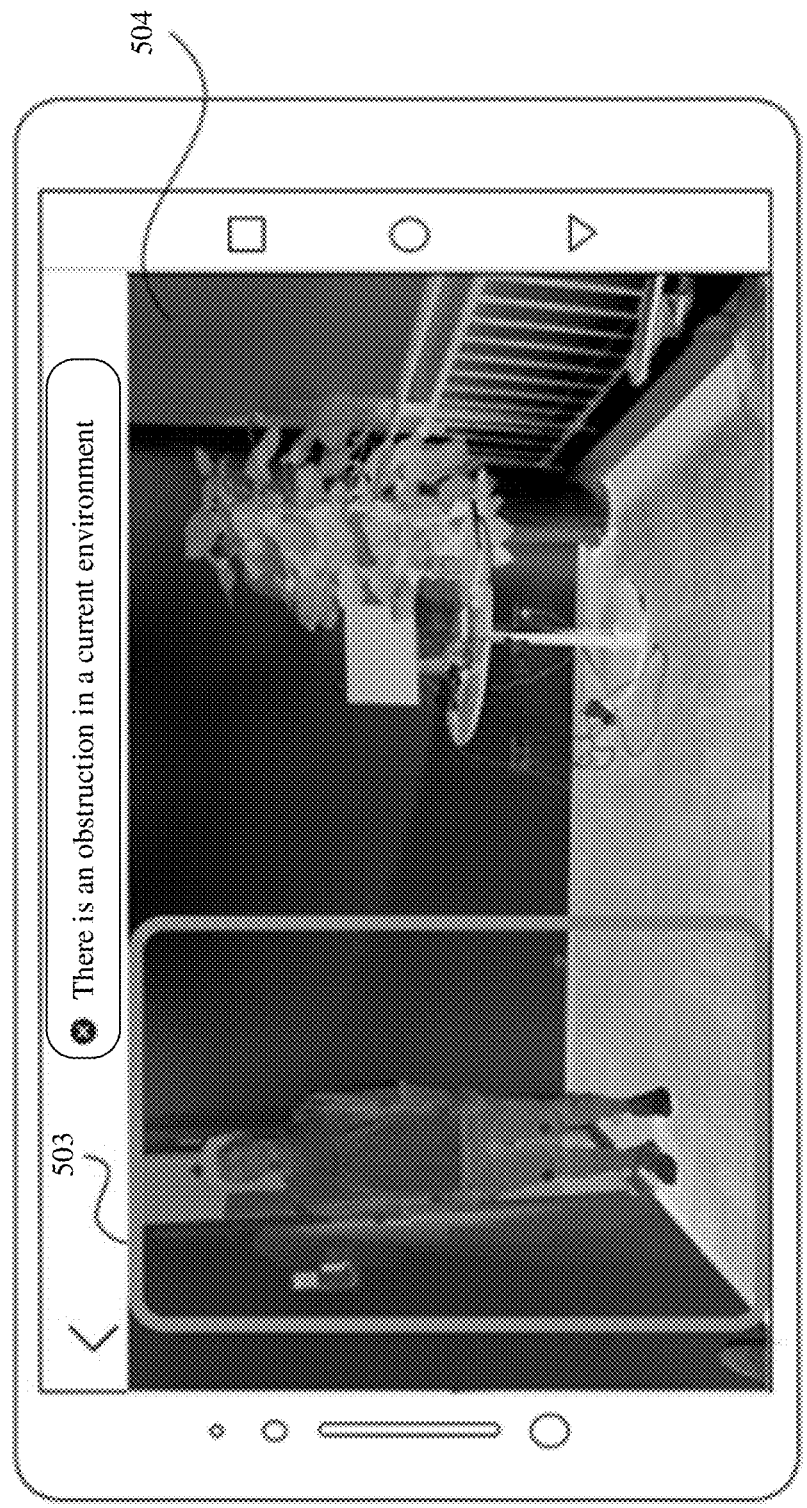

In a possible implementation, after detecting that the user taps the camera field of view 504, the mobile phone may enter a full-screen display interface of the camera field of view 504, for example, may display an interface shown in FIG. 5(b). All of the touchscreen is used to display the camera field of view 504. The user may determine, by using the full-screen display interface of the camera field of view 504, the picture acquired by the camera and the location of the user in the picture acquired by the camera. Optionally, the interface content displayed in the camera field of view 504 may include a viewfinder frame 503, used to display a framing range (or understood as a display range that is of the picture acquired by the camera and that is on the touchscreen), a location and a size of the framing range in the picture acquired by the camera, a ratio of the framing range to the picture acquired by the camera, and the like.

It should be understood that locations that are on the touchscreen and that are of the target course video interface content 502, the viewfinder frame 503, and the camera field of view 504 shown in FIG. 5(a) and ratios of the target course video interface content 502, the viewfinder frame 503, and the camera field of view 504 to an area of the touchscreen are merely an example. Locations, shapes, areas, and display forms of the target course video interface content 502, the viewfinder frame 503, and the camera field of view 504 may be designed based on an actual requirement. This is not limited in this embodiment of this application. It should be further understood that, in some embodiments, the training interface 501 may include only the viewfinder frame 503 (that is, all of the touchscreen is used to display a preview image in real time), or include the viewfinder frame 503 and the camera field of view 504, and does not include the target course video interface content 502. This is not limited in this embodiment of this application. For ease of understanding and description, an example in which the training interface 501 includes the target course video interface content 502, the viewfinder frame 503, and the camera field of view 504 is used for description in this embodiment of this application.

The camera in this embodiment of this application may be a depth camera (which may also be referred to as a three-dimensional (3D) camera), or may be a conventional camera (which may also be referred to as a two-dimensional (2D) camera or an RGB camera). The depth camera is a camera that may be used to measure a distance (a depth) from an object to the camera, for example, a structured-light (structured light includes infrared speckle structured light, infrared stripe structured light, visible stripe structured light) depth camera based on active projection, a passive binocular camera (such as an RGB binocular camera), and a camera based on a depth measurement principle using reflection time (such as a time of flight (TOF) camera)). The depth camera may be used to collect depth information of an environment, and then perform object recognition, environment modeling, and the like. Compared with the conventional 2D camera, because one dimension of depth information is added, a real world can be better described. It should be understood that, after detecting that the user taps the icon 307, the mobile phone automatically starts the camera application, and displays the preview image in the viewfinder frame 503.

After the target course video is downloaded or buffered, the mobile phone may process the target course video according to the image algorithm, and calculate maximum activity space required for exercise. The maximum activity space is used as one of the inputs used by the mobile phone to recommend a suitable training location to the user. For example, the mobile phone may analyze and process an activity track of a coach in the target course video according to the image algorithm, and calculate maximum activity space corresponding to each training action performed by the coach, to determine maximum activity space required for completing the target course video selected by the user. Alternatively, the mobile phone may analyze and process an activity track of a coach in the target course video according to the image algorithm, to directly obtain maximum activity space required for completing the target course video selected by the user. It should be understood that a type (namely, calculated maximum activity space required by each training action or calculated maximum activity space required by a set of training actions) of the maximum activity space that is required for exercise and that is determined by the mobile phone is related to the image algorithm used by the mobile phone. The image algorithm used by the mobile phone to process the target course video is not specifically limited in this embodiment of this application. It should be further understood that the maximum activity space required for exercise may be understood as that the user may complete a training action in the activity space. The maximum activity space required for exercise may be a cylinder (depending on a diameter and a height), an elliptical cylinder (depending on an elliptical cross section and a height), a cube (depending on an edge length), a cuboid (depending on a length, a width, and a height), another regular or irregular three-dimensional shape, or the like; or may be a circle, an ellipse, a square, a rectangle, another regular or irregular planar shape, or the like. When the maximum activity space required for exercise is in a planar shape, the maximum activity space may be understood as an activity range required when the user takes exercise on the ground. The maximum activity space that is required for exercise and that is calculated by the mobile phone may be activity space of the coach in the target course video, or may be a multiple of the activity space of the coach in the target course video. This is not limited in this embodiment of this application.

After entering the training interface 501, the mobile phone automatically starts the camera application. The mobile phone may obtain a current frame of image, process the current frame of image according to the image algorithm, and recognize a coordinate of a location of the user in a current picture and/or calculate a location that meets a recommended activity space and that is in a current scenario. The recommended activity space may be the maximum activity space that is required for exercise and that is obtained by the mobile phone after processing the target course video, or may be a value obtained after the maximum activity space required for exercise is adjusted based on a body shape parameter of the user such as a height, a waist circumference, and a volume. Optionally, the mobile phone may process the current frame of image according to an image algorithm, to recognize the location of the user in the current picture, and process the current image according to another image algorithm, to obtain the location that meets the recommended activity space and that is in the current scenario. Optionally, the mobile phone may process the current frame of image according to a same image algorithm, and may extract information about the user while scanning the current scenario, to recognize the location of the user in the current picture.

After calculating the location that meets the recommended activity space and that is in the current training scenario, namely, a training location recommended by the mobile phone, the mobile phone may guide the user to move to the training location recommended by the mobile phone. The foregoing process of processing both the target course video and the current frame of image is completed inside the mobile phone. After the training location recommended by the mobile phone is obtained, the recommended training location or a prompt for guiding the user to move to the recommended training location is displayed in a display interface.

In a possible implementation, the preview interface (the viewfinder frame 503) may include a recommended region, and the recommended region is the training location recommended by the mobile phone. The recommended region may be a three-dimensional region with depth information, for example, a recommended region 505 shown in FIG. 5(*a*), FIG. 5(*c*), and FIG. 5(*e*). The recommended region 505 may be displayed on the ground in the preview image. For example, as shown in FIG. 5(*e*), the user may move based on a location of the recommended region 505 until the user stands in a range of the recommended region 505.

In another possible implementation, the preview interface (namely, the viewfinder frame 503) may further include a prompt box. The prompt box may be used to remind the user whether there is an obstruction in a current environment or whether the user is already at the recommended training location, or may be used to prompt the user with a movement direction and/or a movement distance. For example, when a location of the user does not meet the activity space required for performing training or the user is not at the recommended training location, the prompt box may be used to display text content such as "there is an obstruction in the current environment", "space is insufficient", "a condition is not met", or "not in the recommended region", to remind the user that the user cannot start training at the current location. When the user is at the recommended training location, the prompt box may be used to display text content such as "a condition is met", "already in the recommended region", or "start training", or the prompt box may be hidden or disappear, to remind the user that the user may start training at the current location. For another example, when the user is not at the recommended training location, the prompt box may be used to display text content such as "move a little to the left", "move one step to the left", or "move 20 cm to the right", to prompt the user with the movement direction and/or the movement distance. When the user reaches the recommended training location, the prompt box may be used to display text content such as "already in the recommended region", "stay still", or "OK", or the prompt box may be hidden or disappear, to remind the user that the user is already at the recommended training location and may start training. For another example, when a location of the user does not meet the activity space required for performing training or the user is not at the recommended training location, the prompt box may be used to display a graphic "×" to remind the user that the user cannot start training at a current location. When the user is at the recommended training location, the prompt box may be used to display a graphic "√" to remind the user that the user may start training at the current location. Optionally, when the user does not reach the recommended training location for a long time, for example, after a preset time (for example, 5 seconds) expires, the prompt box may be used to display a graphic "!" to remind the user that the user has not reached the recommended training location before the preset time expired. It should be understood that the prompt box may be used to display a text, a graphic, or a combination of a text and a graphic. This is not limited in this embodiment of this application. It should be noted that in this embodiment of this application, when the user is not located in the recommended region or is not totally located in the recommended region, the mobile phone may consider that the user is not at the recommended training location. When the user is totally located in the recommended region, the mobile phone may consider that the user is at the recommended training location.

For example, as shown in FIG. 5(*a*), the viewfinder frame 503 includes a prompt box 506. The mobile phone may obtain a current video frame and then process the current video frame, to calculate a location of the user in the current environment. As shown in FIG. 5(*b*), because the user stands near a wall at a current moment, the space in which the user is located is insufficient to perform training or the user is not in the recommended region 505. In this case, the prompt box 506 may be used to display "there is an obstruction in the current environment" and the graphic "×" to remind the user that the current location is not suitable to perform training or the user is not in the recommended region 505. As shown in FIG. 5(c) and FIG. 5(d), after a preset time expires after the camera is started, the mobile phone obtains a video frame existing after the preset time expires and processes the video frame, to calculate a location that is of the user in the environment and that exists after the preset time expires. If the space in which the user is located is still insufficient to perform training or the user does not reach the recommended region 505, the prompt box may be used to display "there is an obstruction in the current environment" and the graphic "!" to remind the user that the location that is of the user and that exists after the preset time expires is not suitable to perform training or the user is not in the recommended region 505. When the user moves to the training location recommended by the mobile phone, for example, as shown in FIG. 5(e) and FIG. 5(f), when the user totally stands in the recommended region 505, the prompt box may be used to display "there is no obstruction in the current environment" and the graphic "√" to remind the user that training may be performed at a current location or the user is already in the recommended region 505. Optionally, when the user moves to the training location recommended by the mobile phone, the prompt box may disappear or be hidden after displaying "there is an obstruction in the current environment" and the graphic "√" for a short time.

Figure 5C:
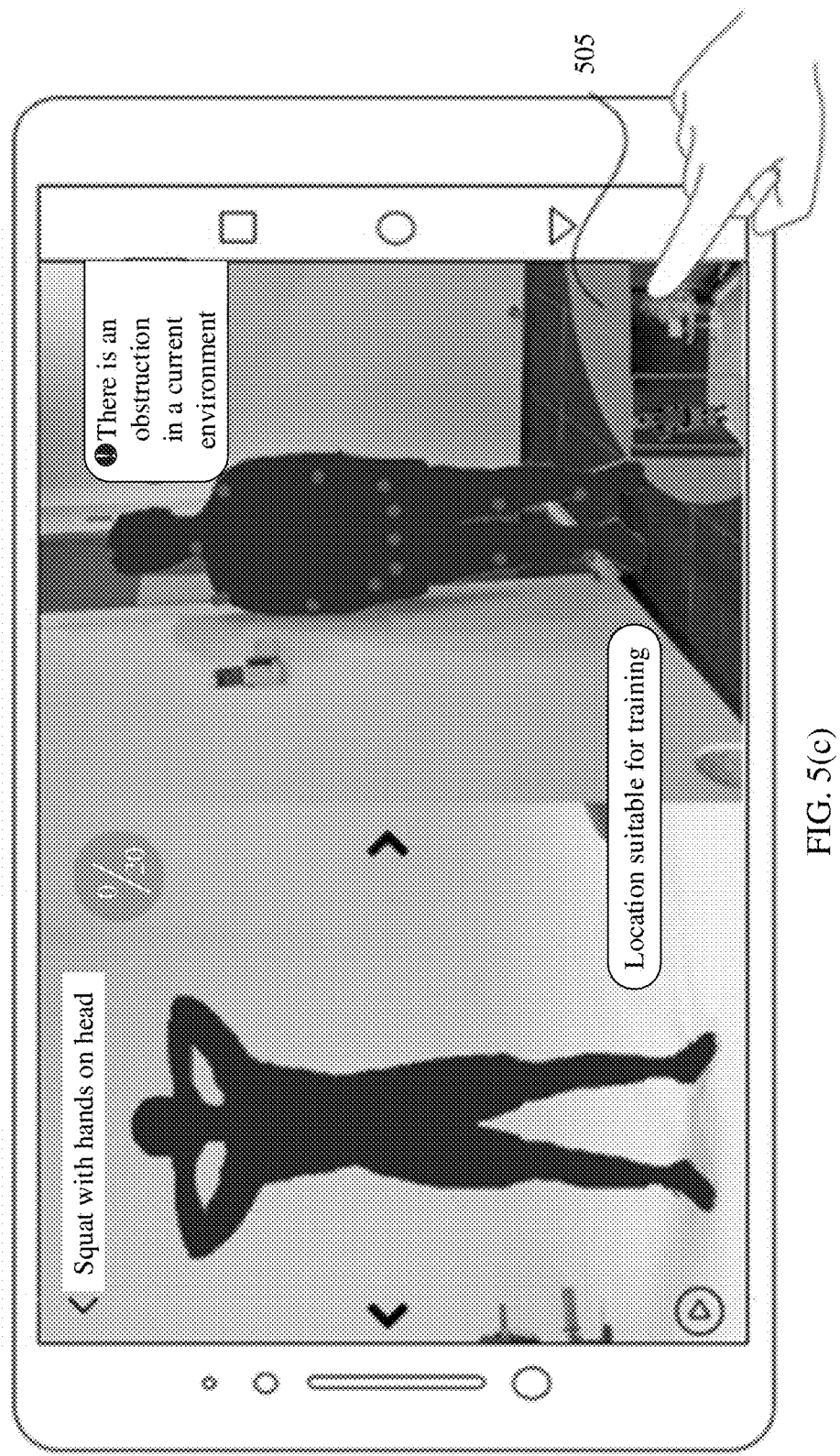
Figure 5D:
Figure 5E:
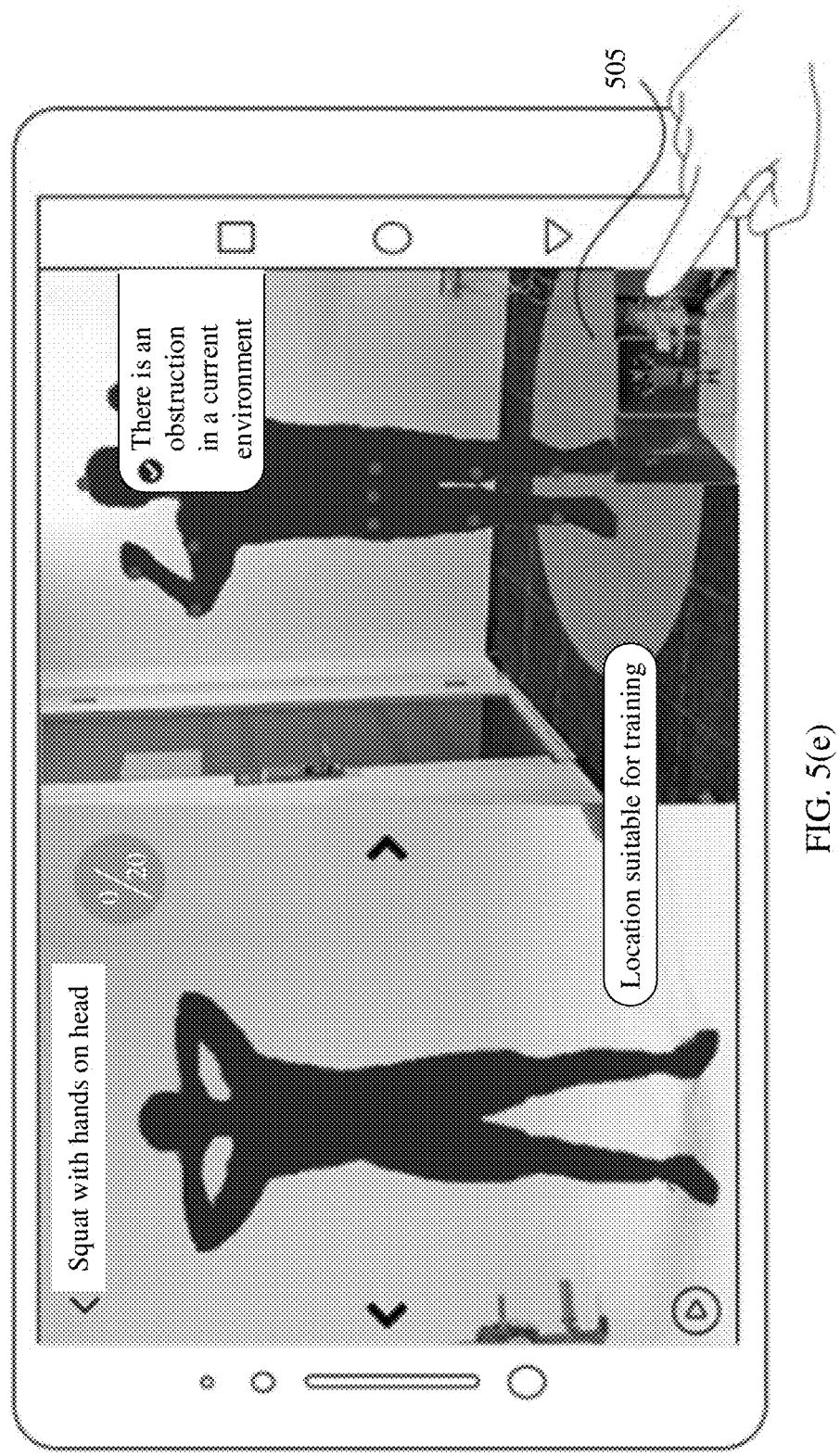
Figure 5F:
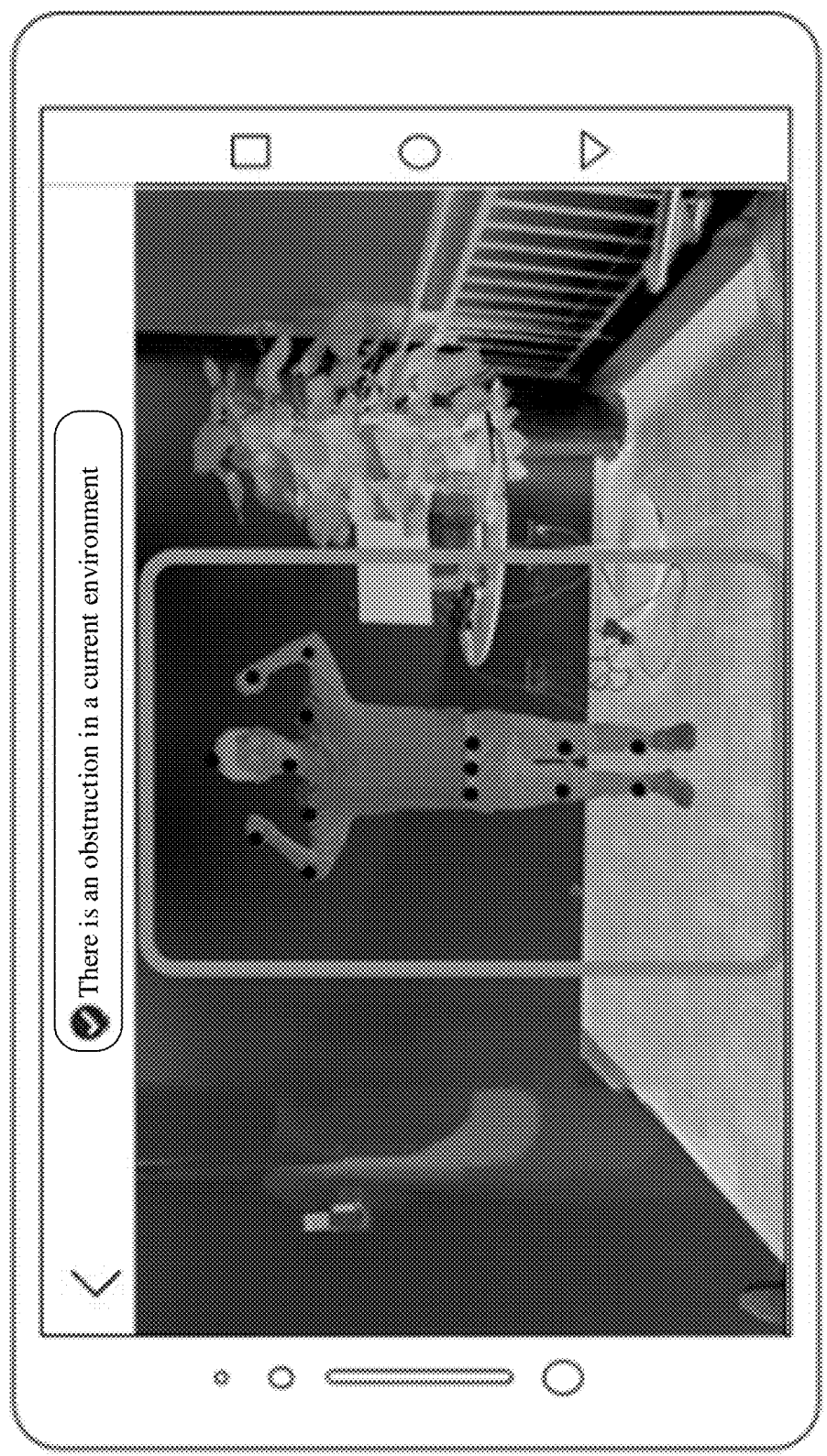

Optionally, the prompt box 506 may be in a form of a pop-up box. For example, as shown in FIG. 5(a), FIG. 5(c), and FIG. 5(e), the prompt box 506 may pop up from an edge of the touchscreen or may be retracted. The prompt box 506 may be floating. For example, as shown in FIG. 5(b), FIG. 5(d), and FIG. 5(f), the prompt box 506 may directly appear or be hidden at a preset location, for example, a middle location above the display interface or the center of the display interface.

Figure 6A:
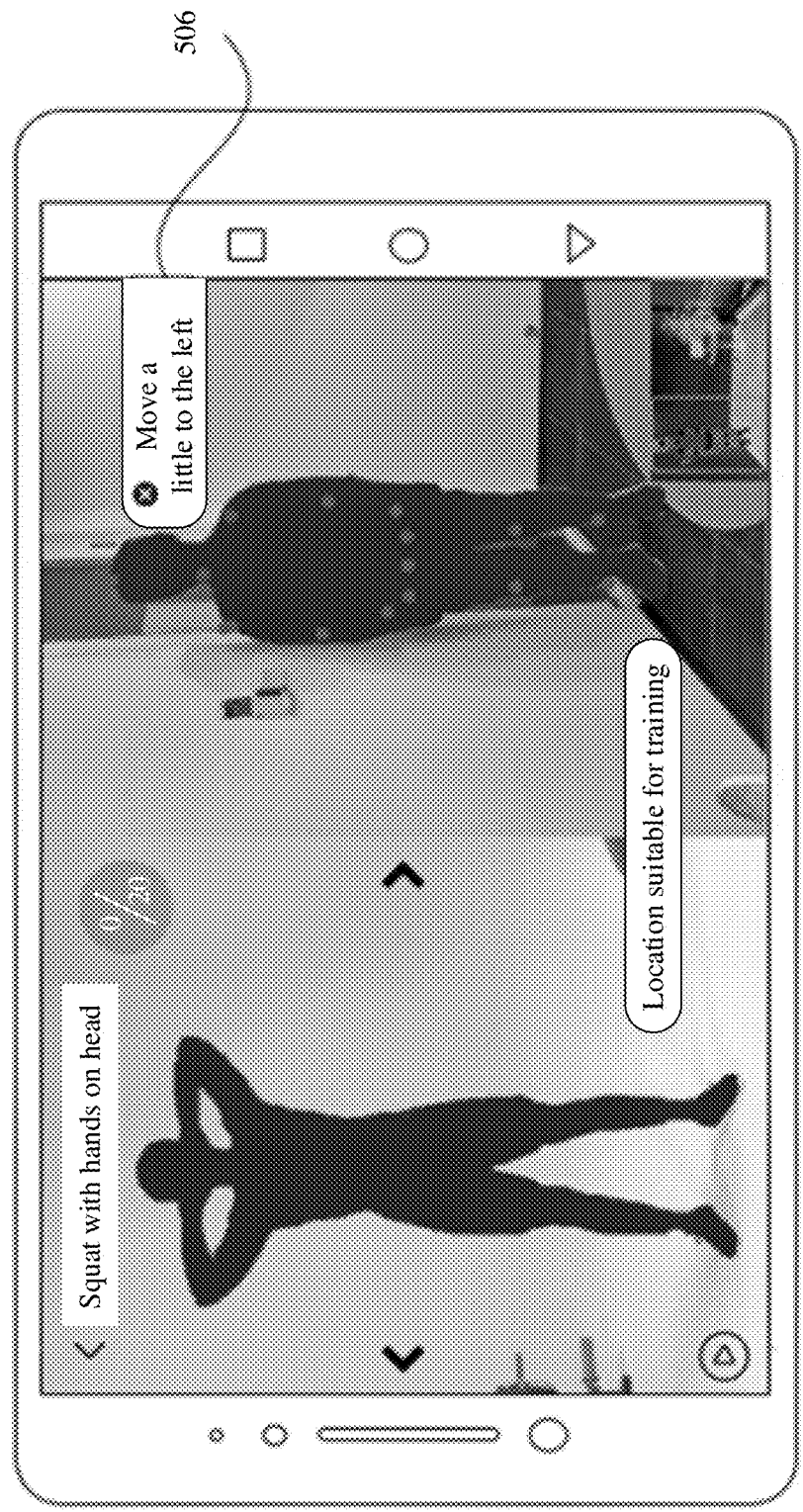
FIG. 6(a) to FIG. 6(c) are schematic diagrams of a graphical user interface in another prompt method according to an embodiment of this application.
Figure 6B:
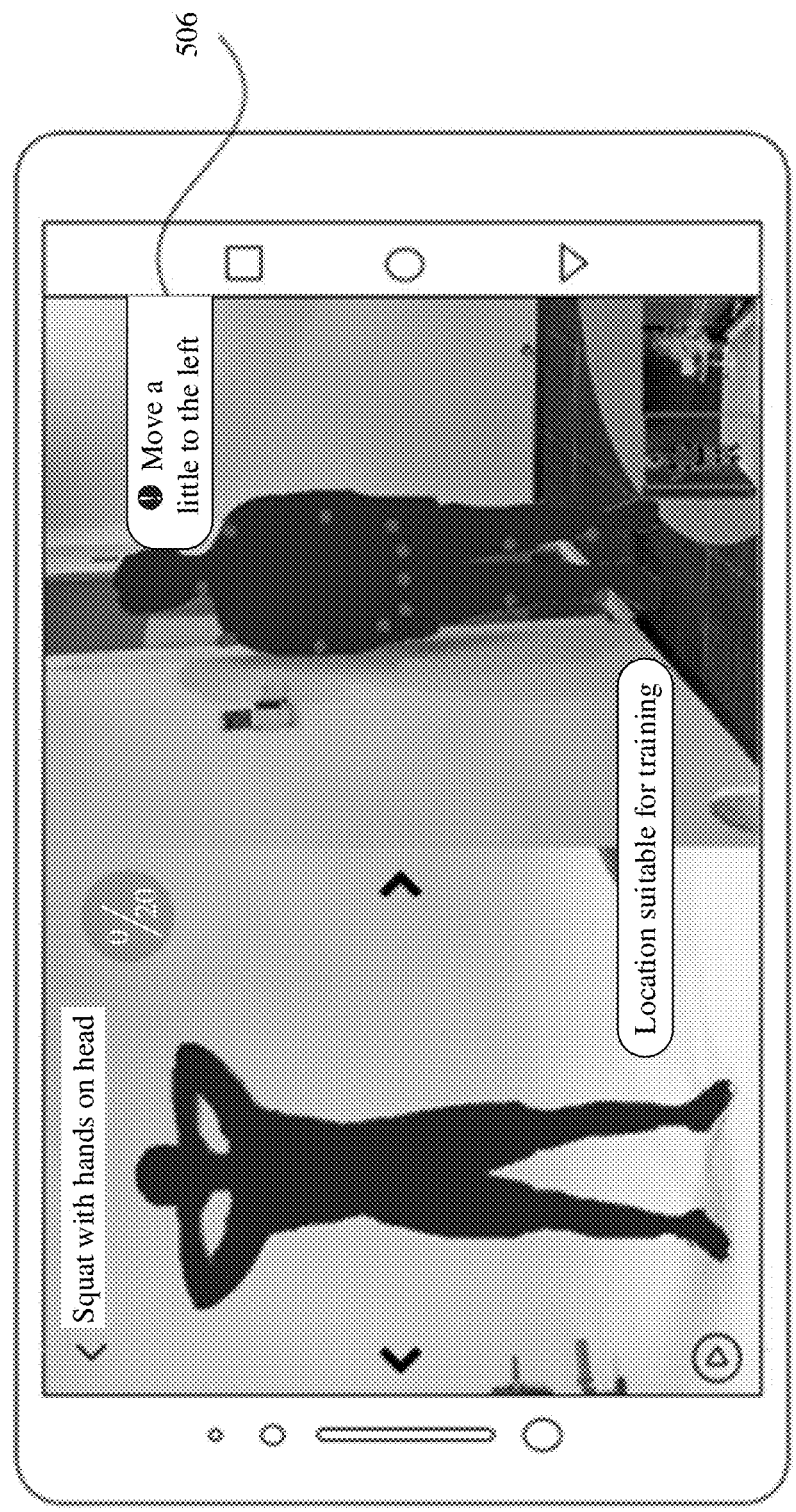
Figure 6C:
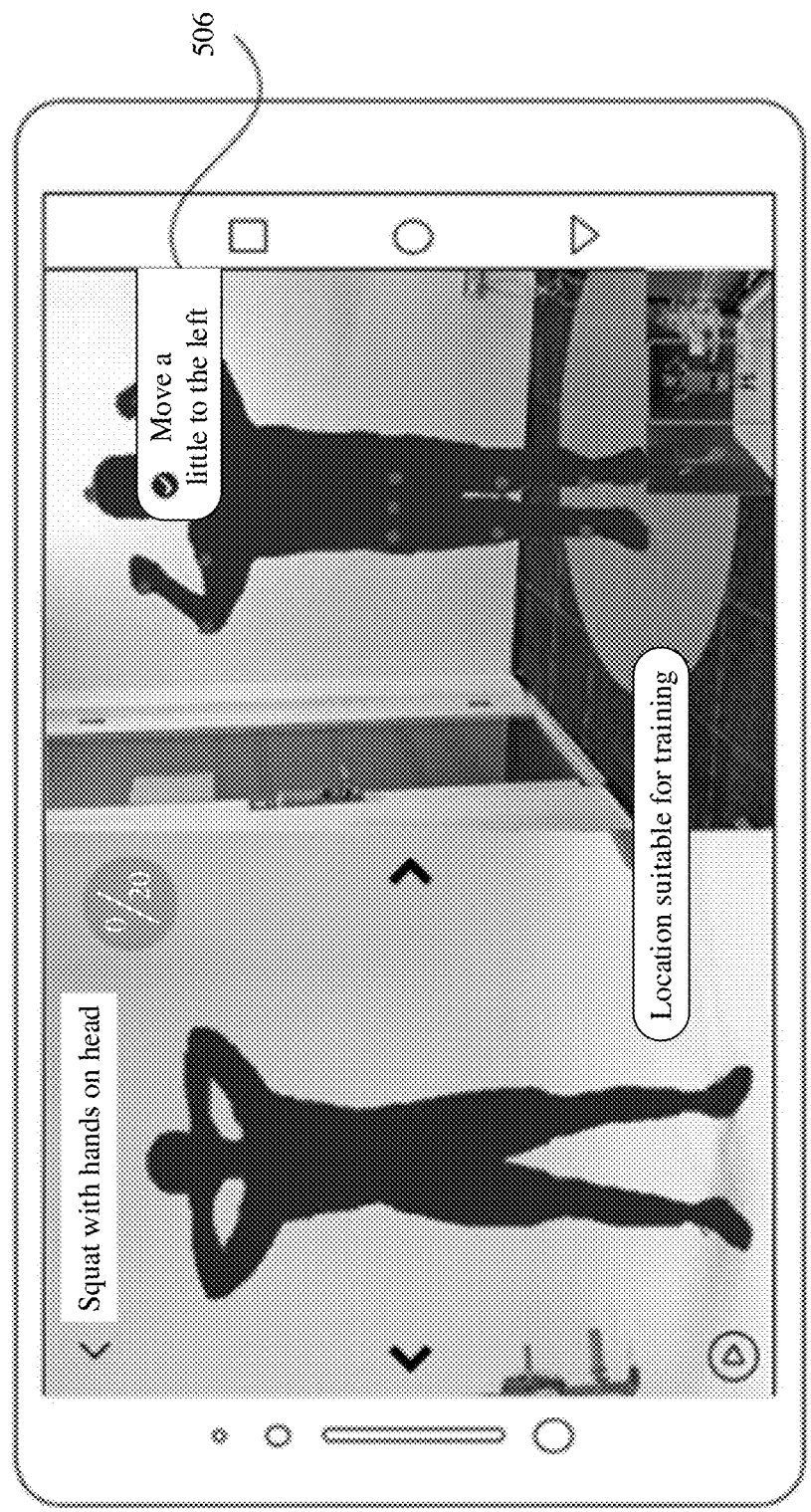
Figure 7A:
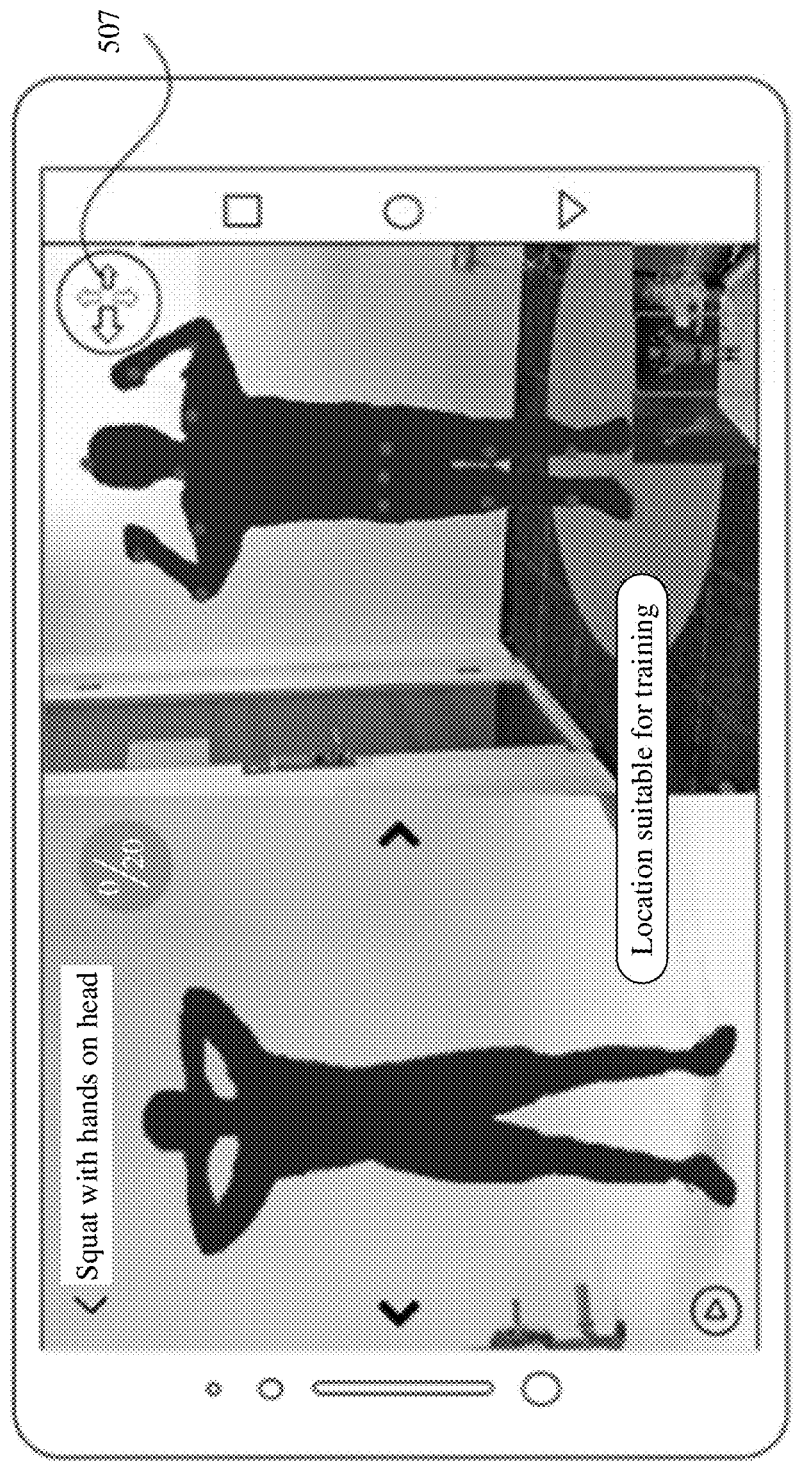
FIG. 7(a) and FIG. 7(b) are schematic diagrams of a graphical user interface in still another prompt method according to an embodiment of this application.
Figure 7B:
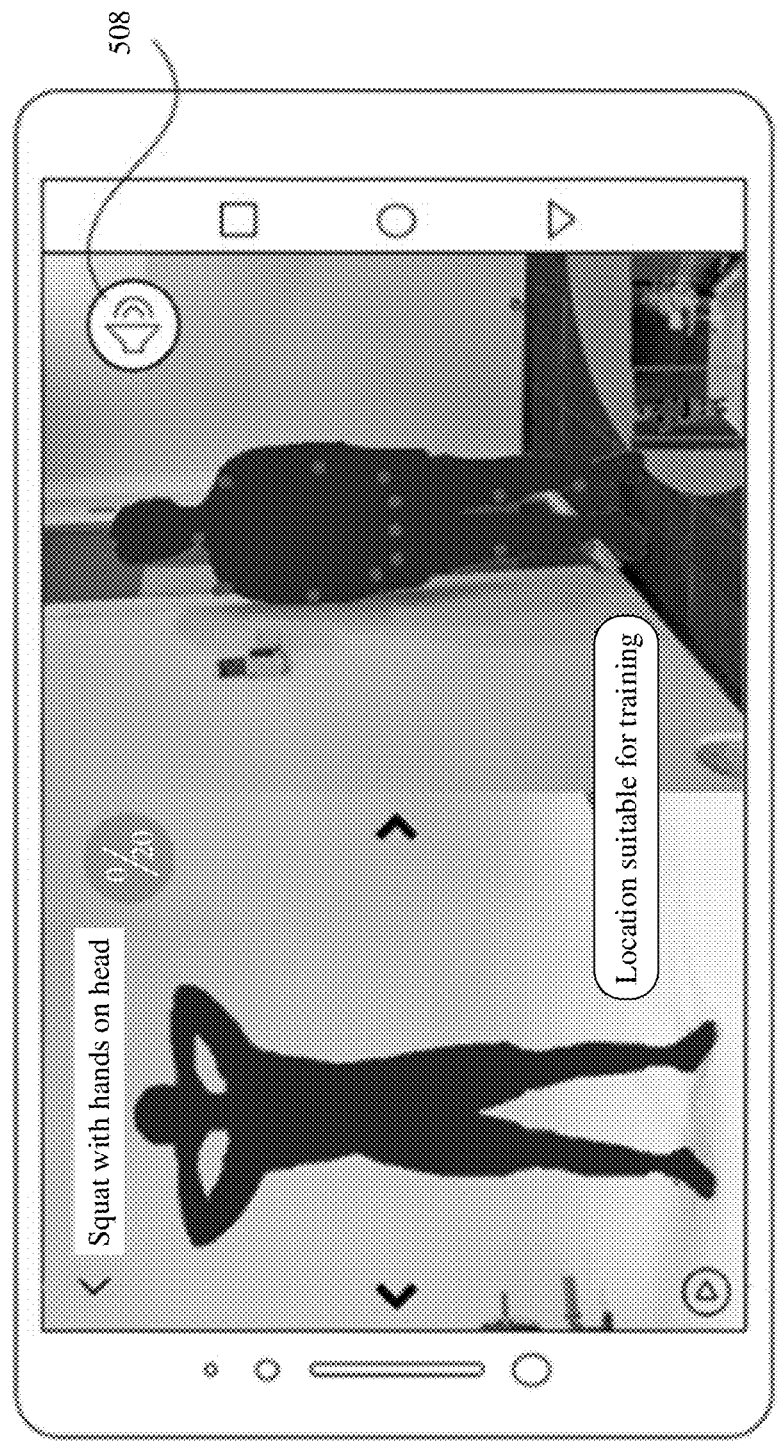

For example, as shown in FIG. 6(a), after obtaining the location of the user in the current environment, the mobile phone may determine a direction and/or a distance in which the user needs to move, based on the current location (for example, a current coordinate of a location of the user) of the user and the training location (for example, a coordinate of a location of the center of the recommended region) recommended by the mobile phone. As shown in FIG. 6(a), the prompt box 506 is used to display "move a little to the left" and the graphic "×". After the preset time expires, the mobile phone obtains the location of the user in the environment, and determines again, based on the location of the user and the training location recommended by the mobile phone, the direction and/or the distance in which the user needs to move. If the user is still not at the recommended training location, as shown in FIG. 6(b), the prompt box 506 may be used to display "move a little to the left" and the graphic "!". If the user moves to the training location recommended by the mobile phone, the mobile phone determines, based on the location of the user and the training location recommended by the mobile phone, that the user does not need to move (for example, when a difference between the coordinate of a location of the user and the coordinate of a location of the center of the recommended region is less than a threshold, the mobile phone may determine that the user does not need to move). As shown in FIG. 6(c), the prompt box 506 may be used to display "move a little to the left" and the graphic "√". It should be understood that the movement direction with which the mobile phone prompts the user may be based on the user. For example, "move a little to the left" displayed in the prompt box 506 is used to prompt the user to move to the left of the user. It should be further understood that the movement direction with which the mobile phone prompts the user may be determined based on the location of the user in the current environment and the training location recommended by the mobile phone. The movement direction is not limited to movement to the left and the right, and may be movement to the front, the back, the left front, the right back, or the like. A manner in which the mobile phone prompts the user with the movement direction and/or the movement distance is not limited to a text prompt, or may be a graphic prompt and/or a voice prompt. For example, as shown in FIG. 7(a), the mobile phone may display a graphic prompt such as a direction icon 507 to prompt the user with the direction and/or the distance in which the user needs to move. Alternatively, as shown in FIG. 7(b), a speaker icon 508 may be displayed in an interface of the mobile phone, to indicate that the mobile phone prompts, by using the speaker, the user with the direction and/or the distance in which the user needs to move.

In a process in which the mobile phone guides the user to move to the recommended training location, the mobile phone may perform region of interest (ROI) adaptive adjustment for the camera, that is, a picture in which the user is located in the center of the framing range is always displayed in the viewfinder frame.

Optionally, a wide-angle camera that can obtain a larger field of view may be used as the camera, so that the camera can be fixed. In a movement process of the user, the camera may perform ROI adaptive adjustment, so that the user is always in the center of the framing range. In some other embodiments, a rotatable camera may be used as the camera, that is, a lens of the camera may be rotated by a mechanical structure to obtain a larger field of view. In this way, in a movement process of the user, the camera may also rotate as the user moves, so that the user is always in the framing range or always in the center of the framing range. For example, the camera may rotate as the user moves, so that the user is always in the center of the framing range. Alternatively, the camera may rotate when the user reaches an edge of the viewfinder frame, so that the user is always in the framing range. Alternatively, in a movement process of the user, the camera performs ROI adaptive adjustment to keep the user in the center of the framing range, and the camera rotates when the user moves to an edge of the viewfinder frame, to continue to keep the user in the center of the framing range. The wide-angle camera, the rotatable camera, or the like that can obtain a larger field of view can be used to expand a selection range of the training location recommended to the user, to ensure that training is normally performed. For example, when the rotatable camera is used, and a width of a training scenario in which the user is located is insufficient to include a whole body of the user into a display range or there are a large quantity of obstructions, the camera may rotate by using a rotatable mechanical mechanism, to expand a recommendation range for locations to stand, and ensure that training is normally performed.

Before the user moves to the recommended region, the target course video is not played. After the mobile phone detects that the user is at the training location recommended by the mobile phone, for example, the recommended region 505, the training interface 501 further includes interface content for training start confirmation. The mobile phone may prompt the user, in a form of action recognition, gesture recognition, voice recognition, countdown timing, Bluetooth confirmation, and the like, to confirm to start training.

Figure 8A:
FIG. 8(a) to FIG. 8(e) are schematic diagrams of a graphical user interface in a prompt method according to an embodiment of this application.

In a possible implementation, the mobile phone may display a specified action and a prompt text in the display interface, to prompt the user to complete the specified action to start training. As shown in FIG. 8(a), the training interface 501 further includes an action recognition icon 509 used to prompt the user to complete the specified action to start training After detecting that the user completes the specified action, for example, raises both hands, the mobile phone may perform a play operation on the target course video. The mobile phone may recognize the specified action according to an action matching algorithm. However, it should be understood that the mobile phone may detect, according to another algorithm, whether the user completes the specified action. This is not limited in this embodiment of this application.

Figure 8B:
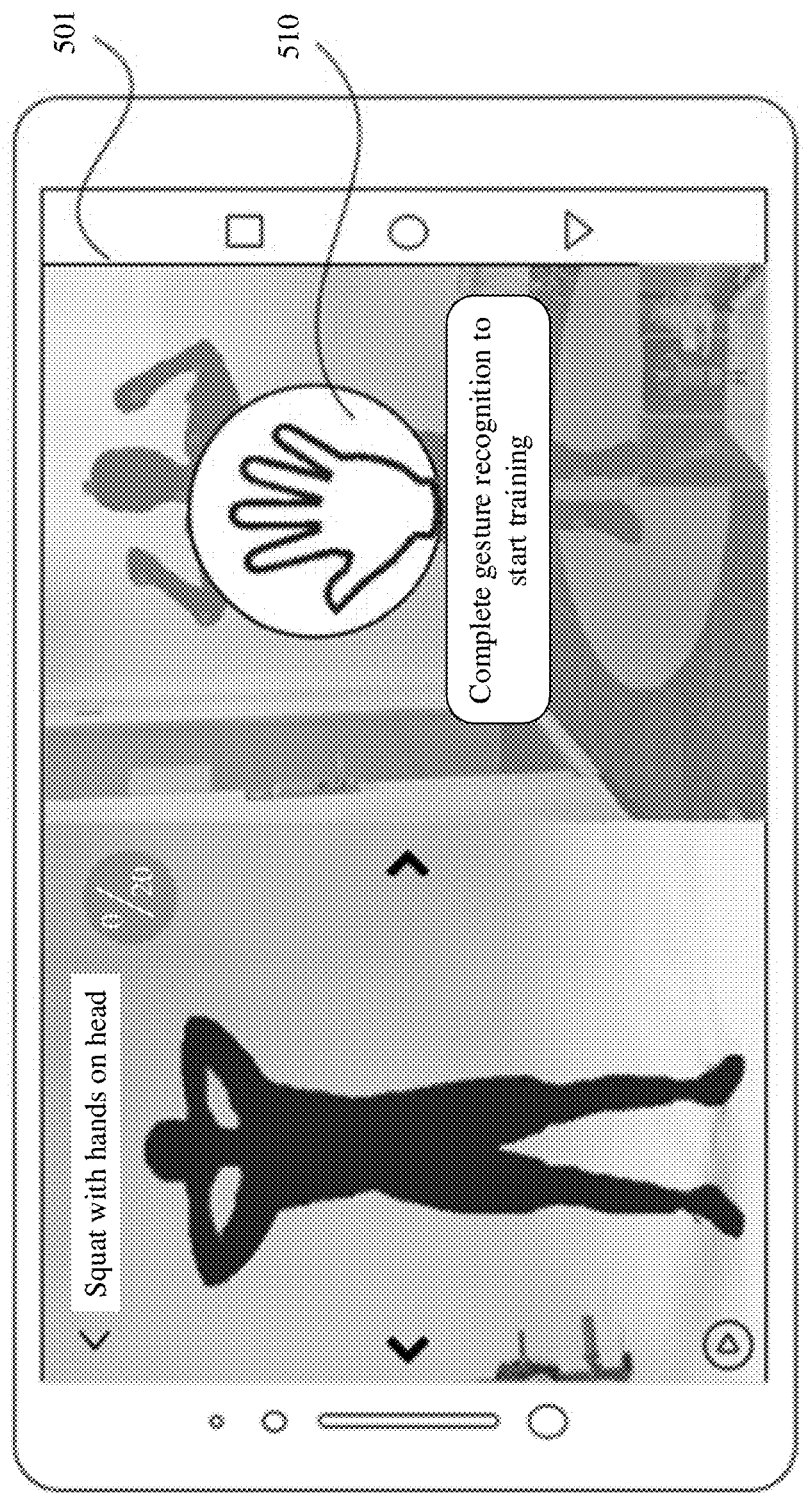

In a possible implementation, the mobile phone may display a gesture and a prompt text in the display interface, to prompt the user to complete gesture recognition to start training. As shown in FIG. 8(b), the training interface 501 further includes a gesture recognition icon 510 used to prompt the user to complete gesture recognition to start training After detecting that the user completes a specified gesture, for example, spreads five fingers, the mobile phone may perform a play operation on the target course video. The mobile phone may recognize the specified gesture according to a gesture matching algorithm. However, it should be understood that the mobile phone may detect, according to another algorithm, whether the user completes the specified gesture. This is not limited in this embodiment of this application.

Figure 8C:
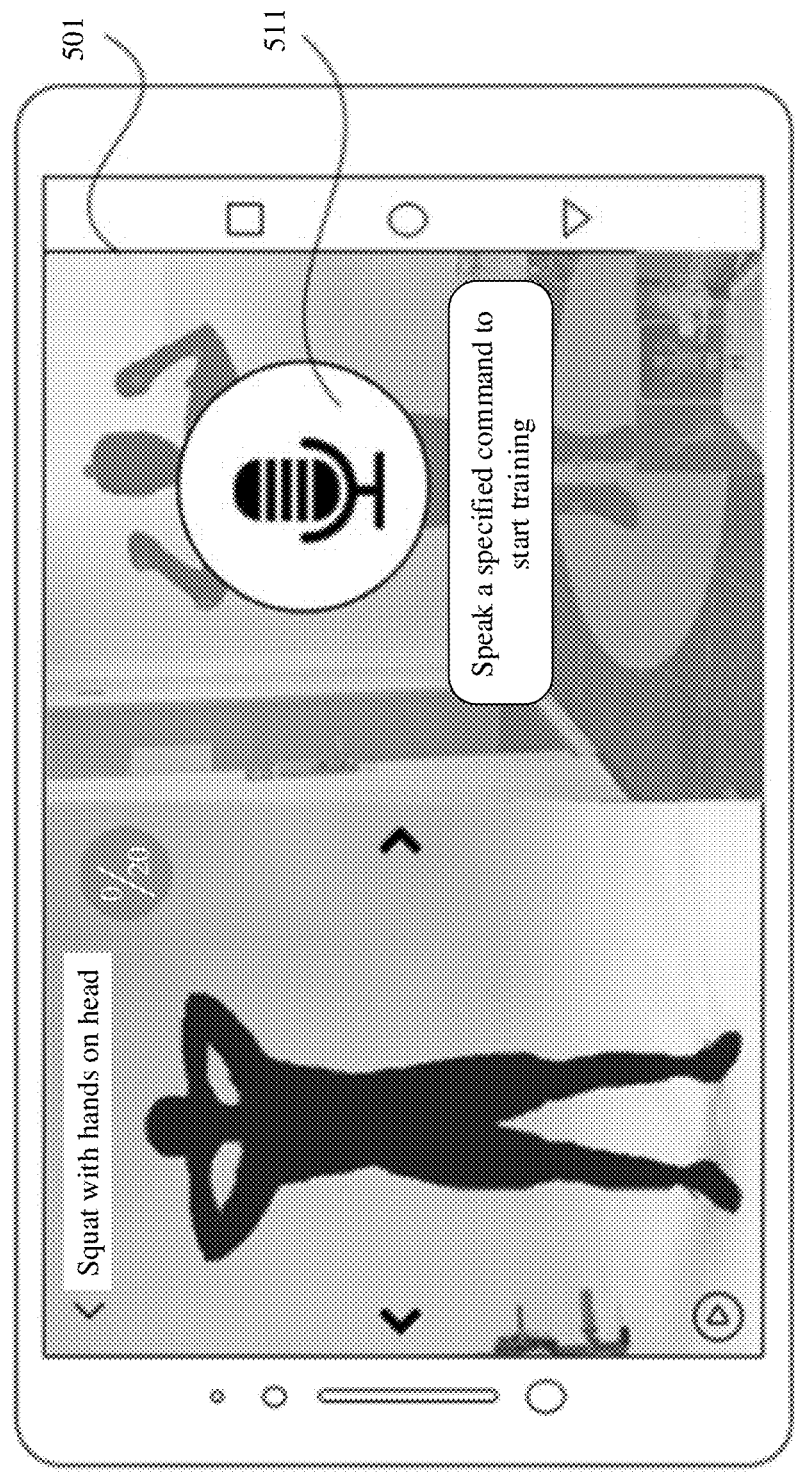

In another possible implementation, the mobile phone may display an instruction recognition icon in the display interface, to prompt the user to speak a specified command to start training. As shown in FIG. 8(c), the training interface 501 further includes an instruction recognition icon 511 used to prompt the user to speak the specified command to start training. After a microphone of the mobile phone detects the voice of the user and recognizes a correct instruction, for example, a "start" instruction, the mobile phone may perform a play operation on the target course video. The mobile phone may recognize the specified command according to a voice recognition algorithm. However, it should be understood that the mobile phone may detect, according to another algorithm, whether the user speaks a correct command This is not limited in this embodiment of this application. It should be further understood that an instruction used for instruction recognition may be by default at delivery of the mobile phone or may be defined by the user. This is not specifically limited in this embodiment of this application.

Figure 8D:
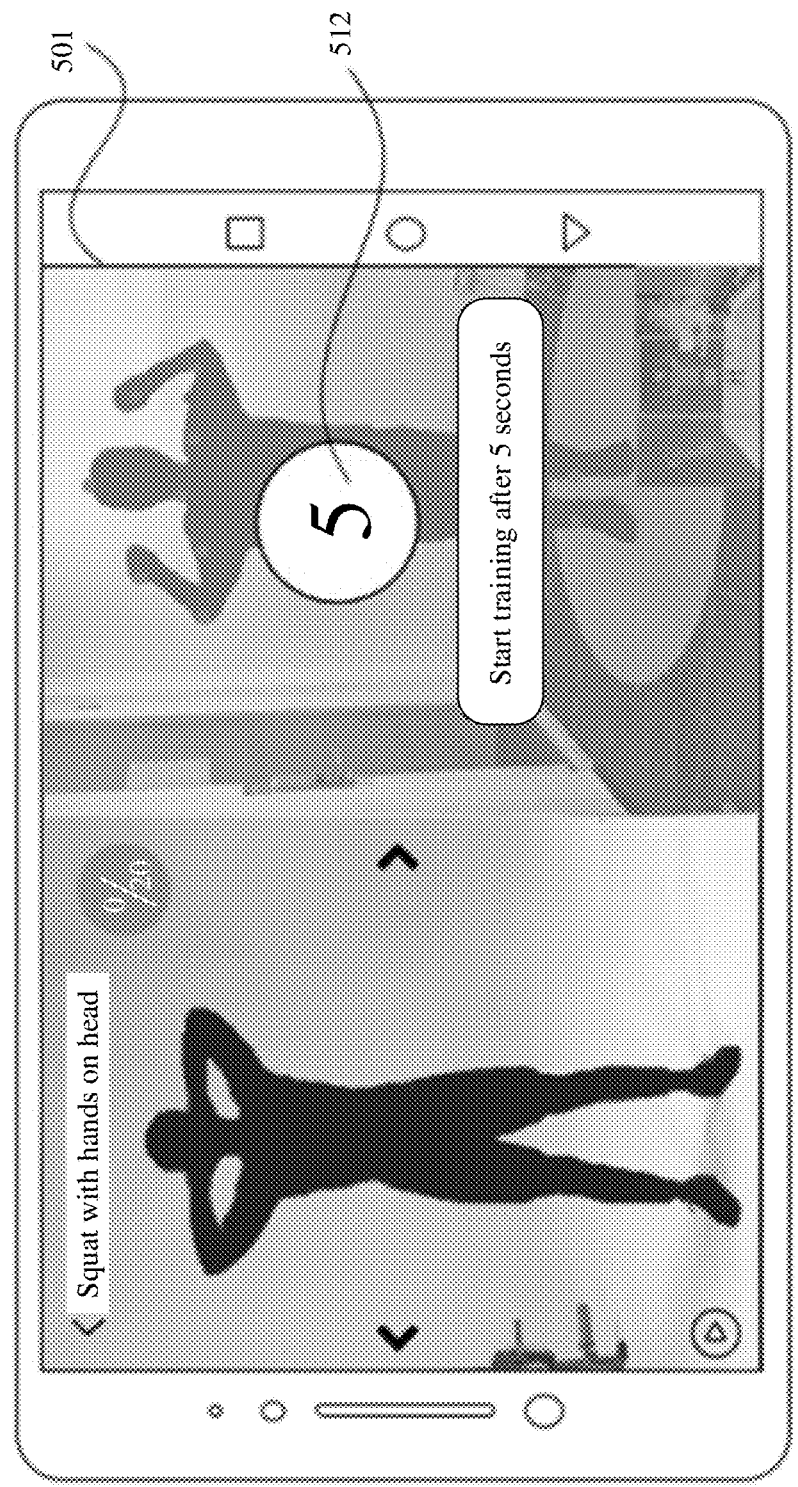

In another possible implementation, the mobile phone may display a countdown timing icon in the display interface, to prompt the user to start training after countdown timing ends. As shown in FIG. 8(d), the training interface 501 further includes a countdown timing icon 512 used to prompt the user to start training after 5 seconds. After countdown timing ends, for example, after the countdown timing icon is displayed as "0", the mobile phone may perform a play operation on the target course video.

Figure 8E:
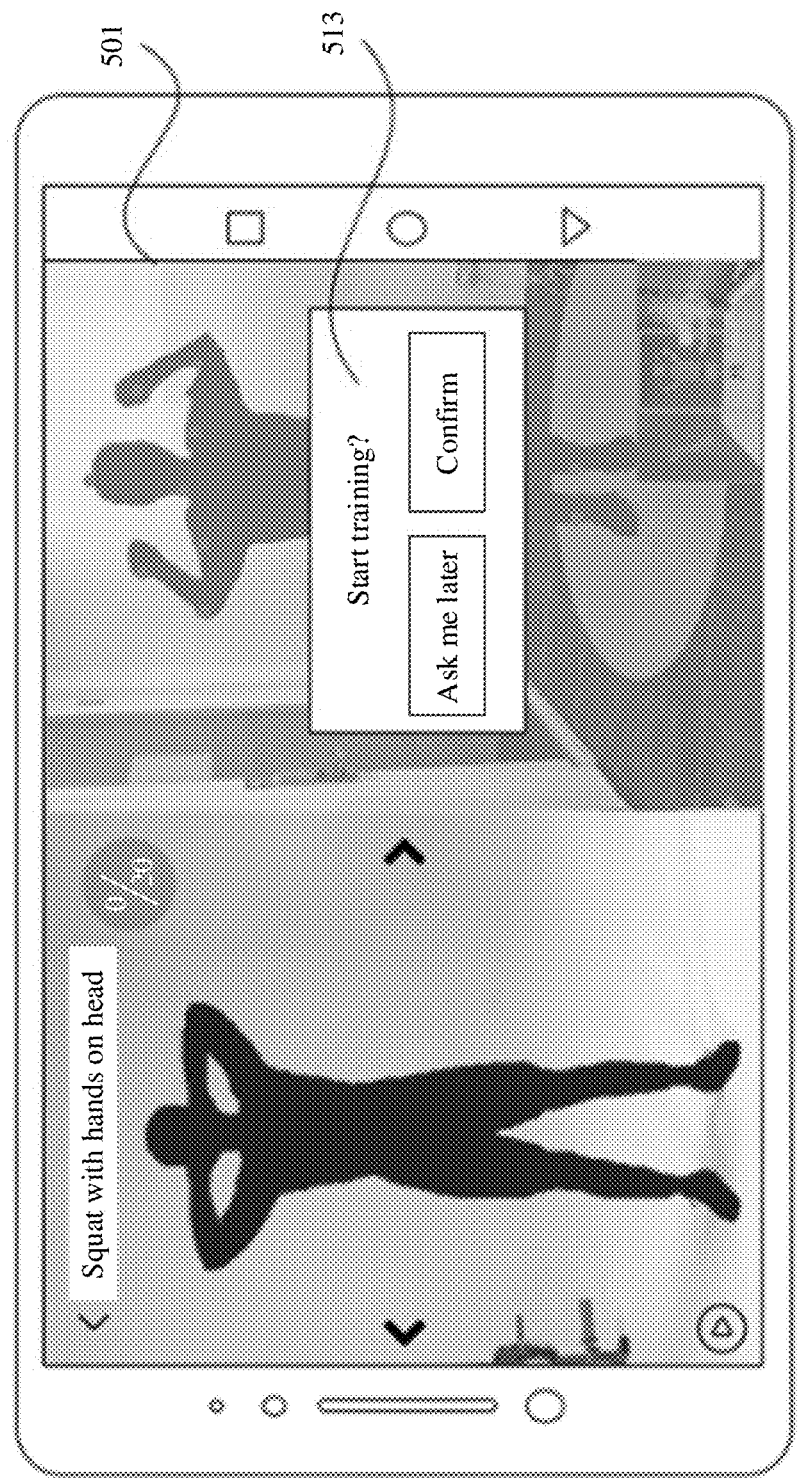

In still another possible implementation, the mobile phone may display a confirmation window in the display interface, to prompt the user to confirm whether to start training. As shown in FIG. 8(e), the training interface 501 further includes a confirmation window 513 used to prompt the user whether to start training. After detecting that a tapping operation is performed on a "confirm" option, the mobile phone may perform a play operation on the target course video. It should be understood that the user may perform the tapping operation by tapping the "confirm" option in the confirmation window 513, or may perform the tapping operation on the "confirm" option in the confirmation window 513 by using a button on a Bluetooth headset. This is not limited in this embodiment of this application.

After the mobile phone detects a signal indicating that the user confirms to start training, the mobile phone may lock the framing range of the camera, to keep the user in the center of the viewfinder frame, and ensure that a picture range displayed on the touchscreen no longer changes in an exercise process.

Figure 9A:
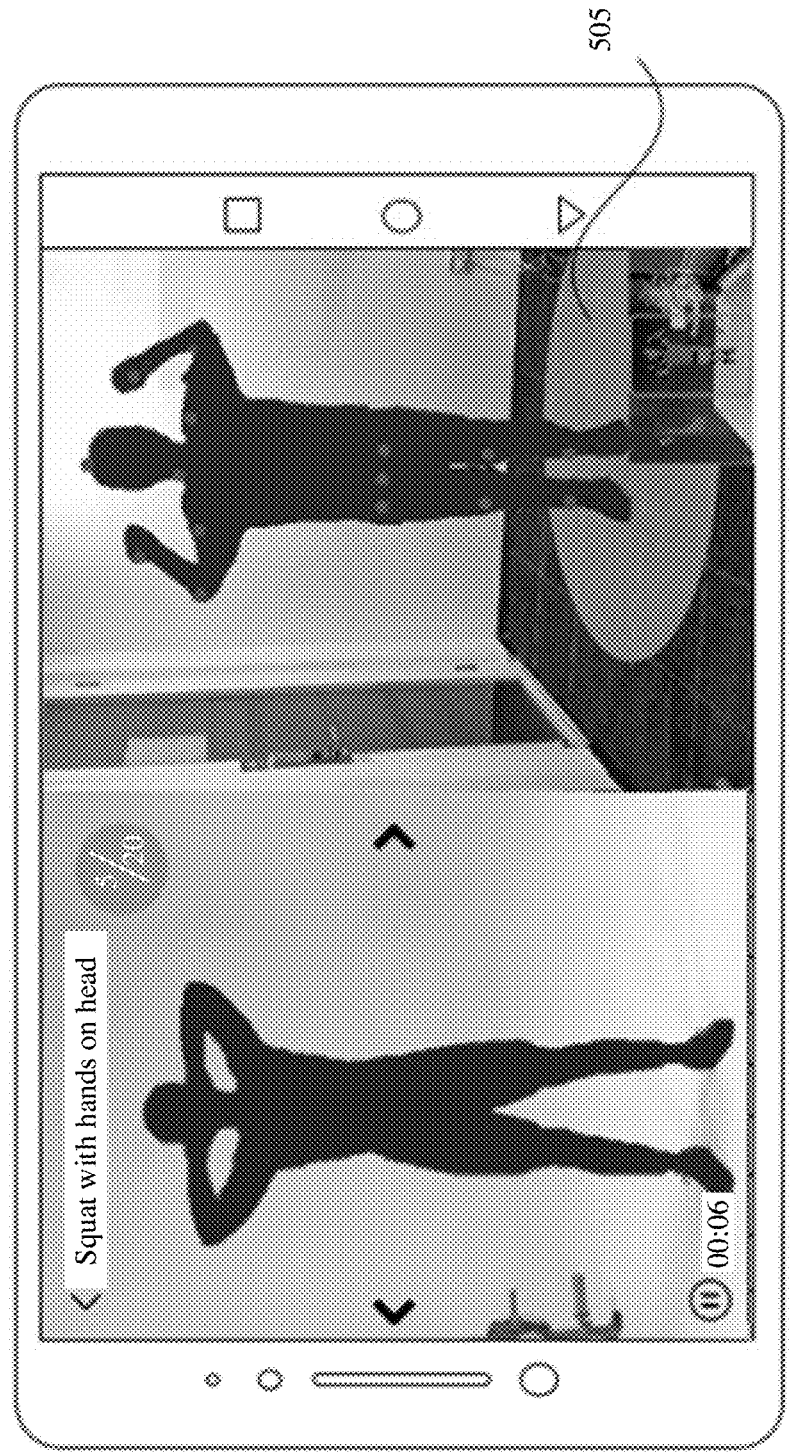
FIG. 9(a) to FIG. 9(c) are schematic diagrams of a graphical user interface in a prompt method according to an embodiment of this application.

After the target course video is played, the user may perform training by following the coach in the target course video or based on guidance of the target course video. One target course video may include a plurality of training actions. Optionally, the training location recommended by the mobile phone to the user may be compatible with all training actions. As shown in FIG. 9(a), the recommended region 505 may be calculated by the mobile phone based on a training action that requires maximum activity space and that is in a plurality of training actions. Because the recommended region 505 may enable the user to complete all training actions, the location of the recommended region 505 may remain unchanged in the entire training process.

Figure 9B:

Optionally, the training location recommended by the mobile phone to the user may be for a corresponding training action. For example, as shown in FIG. 5(a) to FIG. 5(f), the recommended region 505 may be calculated by the mobile phone based on maximum activity space required by the first training action in the target course video. Before each training action is completed, the mobile phone may recommend a training location to the user for the training action. As shown in FIG. 9(b), the recommended region 505 may be calculated by the mobile phone for activity space required by a current training action "bow-step stretching". After a previous training action is completed, the mobile phone may perform a pause operation on the target course video, determine a location that is of the recommended region 505 used to complete "bow-step stretching" and that is in a current scenario, guide the user to the recommended region 505, and then perform a play operation on the target course video, to guide the user to complete "bow-step stretching". It should be understood that, for each training action, for interface content used when the mobile phone guides the user to a corresponding recommended region and interface content used to prompt the user to confirm to start training, refer to the foregoing descriptions. Details are not described herein again. The mobile phone may recommend a suitable training location to the user for each training action, so that the user can also normally perform training in a complex training scenario. For example, in a scenario in which exercise space is extremely limited, for a training action that cannot be completed, such as a training action that requires large activity space, the mobile phone may not recommend a training location to the user to skip the training action, and provide, for the user, an action suitable for training in the scenario, so that the user can normally take fitness exercise. This improves user experience.

Figure 9C:
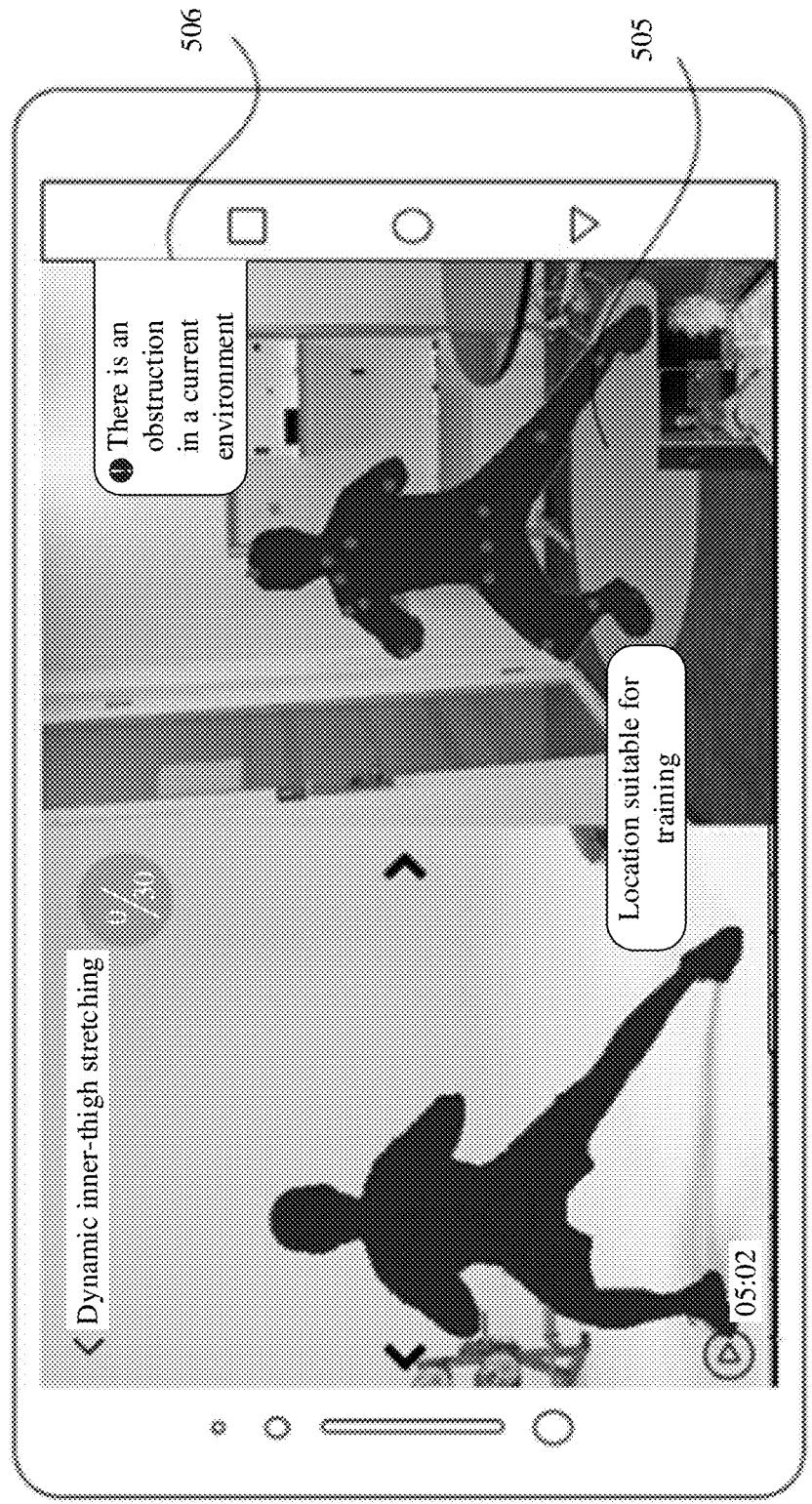
Figure 10A:
FIG. 10(a) to FIG. 10(d) are schematic diagrams of entering a graphical user interface of an application program according to an embodiment of this application.
Figure 10B:
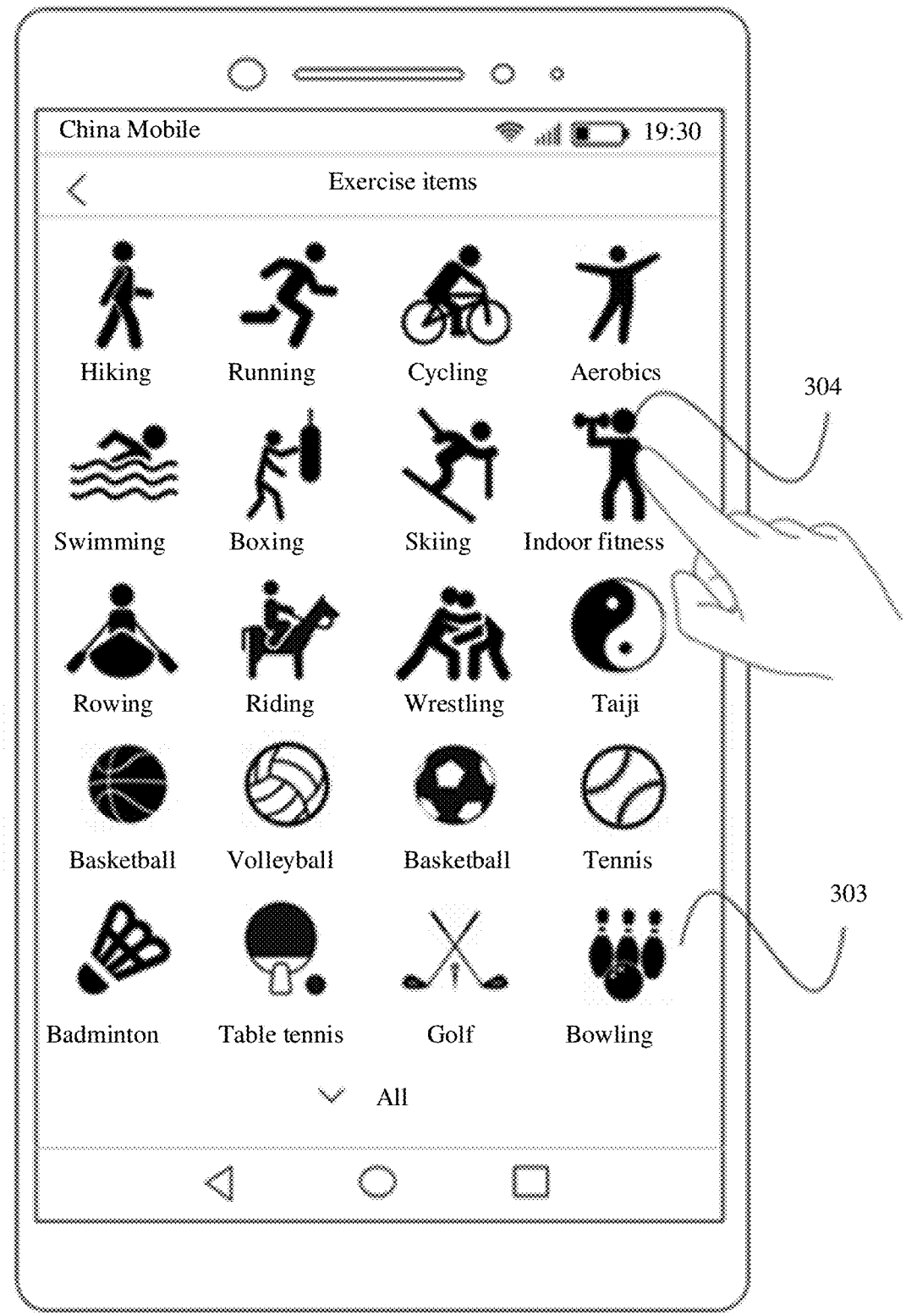
Figure 10C:
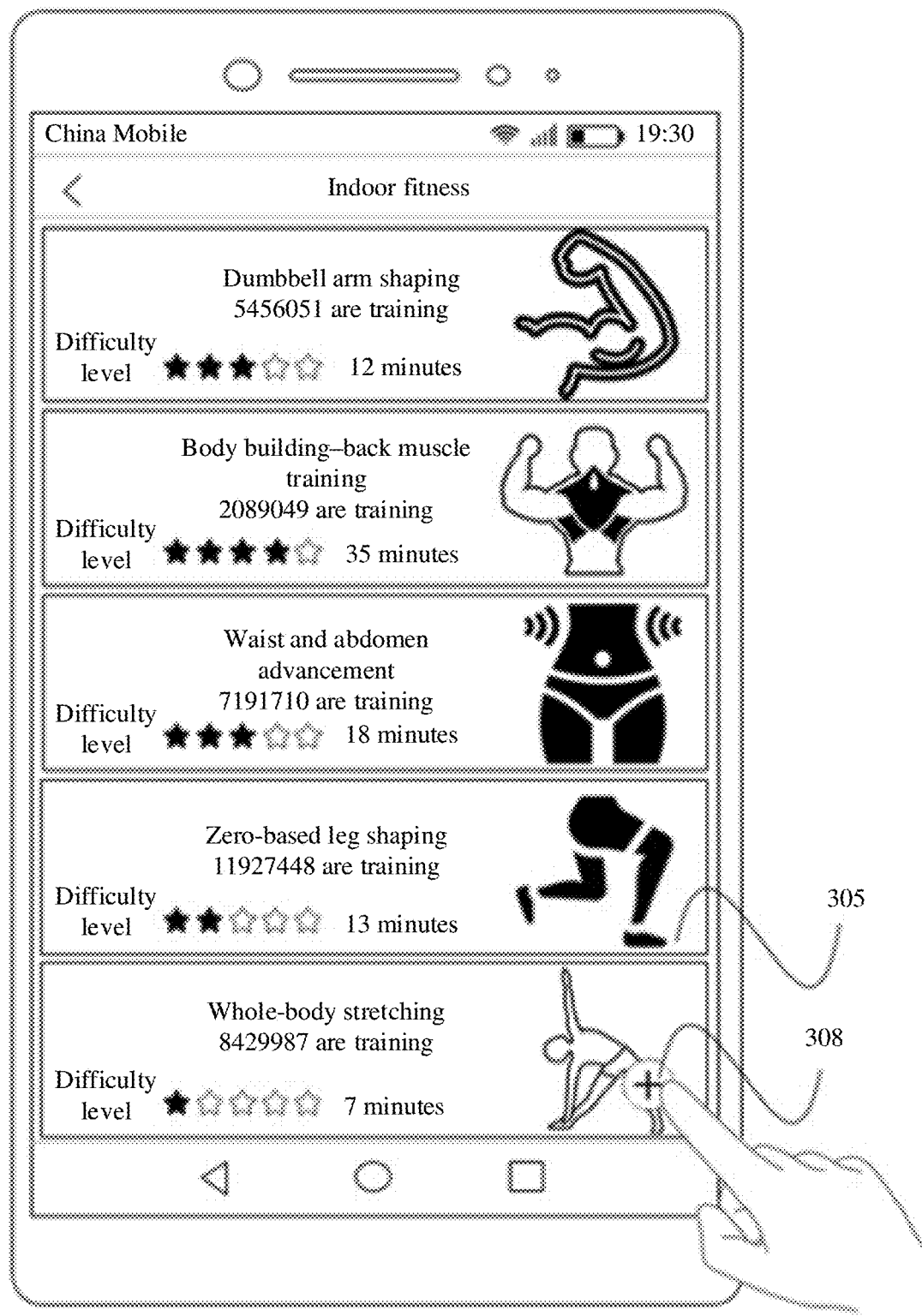
Figure 10D:
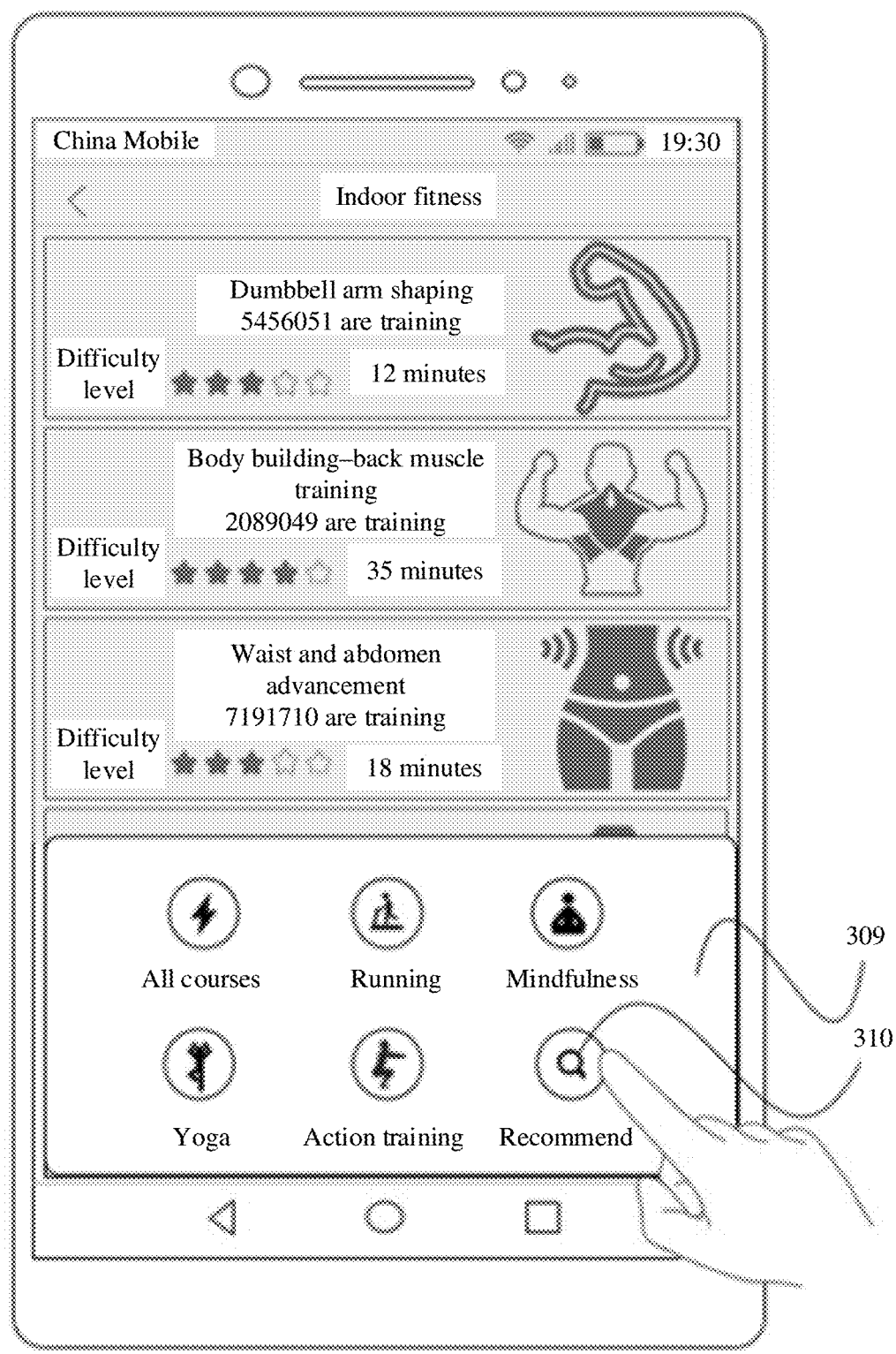

Optionally, if the mobile phone detects that the user still does not reach, after a waiting time expires, the location recommended by the mobile phone, for example, because a range of the recommended region is just equal to the activity space required by a training action, the user is extremely prone to exceed the recommended region or the user does not expect to complete a current training action and intentionally does not move in response to a prompt of the mobile phone, the mobile phone may skip the training action to perform a next training action. As shown in FIG. 9(c), the recommended region 505 may be calculated by the mobile phone for activity space required by a current training action "dynamic inner-thigh stretching". After a previous training action is completed, the mobile phone performs a pause operation on the target course video, and determines a location that is of the recommended region 505 used to complete "dynamic inner-thigh stretching" and that is in a current scenario. In a process of guiding the user to the recommended region 505, the prompt box 506 is always used to remind the user that the user is not in the recommended region. After the waiting time expires, the mobile phone may perform a fast-forward or skip operation on the target course video, to skip the current training action "dynamic inner-thigh stretching" to perform a next training action.

The training location recommended by the mobile phone to the user may be two-dimensional. For example, provided that the user is located in the recommended region displayed on the ground, the mobile phone may determine that the user has reached the recommended training location. The training location recommended by the mobile phone to the user may be three-dimensional, for example, a cylinder. The user needs to be in the recommended region displayed on the ground, and a body of the user further needs to be in the cylinder. In this case, the mobile phone may determine that the user has reached the recommended training location. Optionally, the three-dimensional training location recommended by the mobile phone to the user may be a cylinder, an elliptical cylinder, a cube, or the like. This is not limited in this embodiment of this application.

In the foregoing implementation, the mobile phone may intelligently recommend the training location to the user based on the training scenario and the required training space, and the user does not need to select, based on space required by a course, a location for performing training, to avoid a case in which training cannot be performed due to insufficient space. Further, the mobile phone may further guide the user to the recommended training location in one or more prompt forms, and the user does not need to determine the training location. This improves user experience, and ensures that the user can also normally perform training in a scenario in which exercise space is limited.

Optionally, in some embodiments, the mobile phone may recommend a combination of a target course video and a training action to the user based on a training scenario, and recommend a suitable training location to the user, so that the user performs training based on the recommended combination of the target course video or the training action. The following is described in detail with reference to FIG. 10(*a*) to FIG. 11(*b*).

FIG. 10(*a*) to FIG. 11(*b*) show schematic diagrams of entering a graphical user interface of an application program. FIG. 10(*a*) and FIG. 10(*b*) are the same as FIG. 3(*a*) and FIG. 3(*b*). For specific descriptions, refer to the foregoing descriptions. Only the differences between the interface content are described below. As shown in FIG. 10(*c*), the training plan selection interface 305 may further include a training plan addition control icon 308 (namely, a "+" control). After the user taps the training plan addition control icon 308, a training plan addition window may pop up, for example, a training plan addition window 309 shown in FIG. 10(*d*) may be displayed. The training plan addition window 309 may include a recommendation icon 310. After detecting that the user taps the recommendation icon 310 in the training plan addition window 309, the mobile phone may enter a corresponding display interface, for example, may display a recommendation interface 311 shown in FIG. 11(*a*). The recommendation interface 311 may include a viewfinder frame 312 and recommended content 313. The recommended content 313 may include a training course and/or a training action that are/is recommended by the mobile phone to the user. The recommended training course and/or the recommended training action in the recommended content 313 are/is determined by the mobile phone based on the training scenario. For example, the mobile phone obtains a video frame of a current environment and processes the current video frame, to calculate one or more recommended locations that meet a minimum activity space (or preset activity space). The mobile phone may further obtain in advance the maximum activity space required by all training courses and/or all training actions, and determine, based on the one or more recommended locations that meet the minimum activity space and the maximum activity space required by all the training courses and/or all the training actions, a training course and/or training action that can be used to perform corresponding training at the one or more recommended locations that meet the minimum activity space. The training course and/or the training action are/is a recommended training course and/or a recommended training action that are/is displayed by the mobile phone in the recommended content 313. Therefore, when detecting an operation that the user taps a training course or a training action in the recommended content 313, the mobile phone may enter a corresponding display interface in response to the tapping operation of the user, for example, may display the training interface 501 shown in FIG. 5(*a*). In the training interface 501, the mobile phone may prompt, in a manner such as a prompt box, a direction icon, voice, or a recommended region displayed on the ground, the user with a recommended training location corresponding to the training course or the training action selected by the user, and guide the user to the recommended training location. A manner in which the mobile phone guides the user to move to the recommended training location is similar to the foregoing descriptions. For details, refer to the foregoing descriptions. Details are not described herein again. It should be understood that display interfaces in which the training plan addition control icon 308 and the training plan addition window 309 are located are merely an example. The training plan addition control icon 308 and the training plan addition window 309 may be displayed in any display interface after the fitness application is entered and before the training interface 501 is displayed on the touchscreen. This is not limited in this embodiment of this application. It should be understood that in some embodiments icon 308 could also be a button 308.

In this embodiment of this application, the mobile phone may determine, based on a training scenario, a training location that can meet a training condition, and may recommend, to the user based on obtained a maximum activity space required by a training course and/or a training action, a target training course or a training action that is suitable to perform training in the training scenario. The user does not need to select the target training course based on the scenario. This avoids a case in which the target training course selected by the user cannot be used to perform training in the current scenario.

In a possible implementation, a size of the required training space may be defined by the user. After detecting that the user taps the recommendation icon 310 in the training plan addition window 309, the mobile phone may enter a corresponding display interface, for example, may display a recommendation interface 311 shown in FIG. 11(*b*). The recommendation interface 311 may include a user-defined window 314, and the user may set the size of the required training space in the user-defined window 314.

Figure 11A:
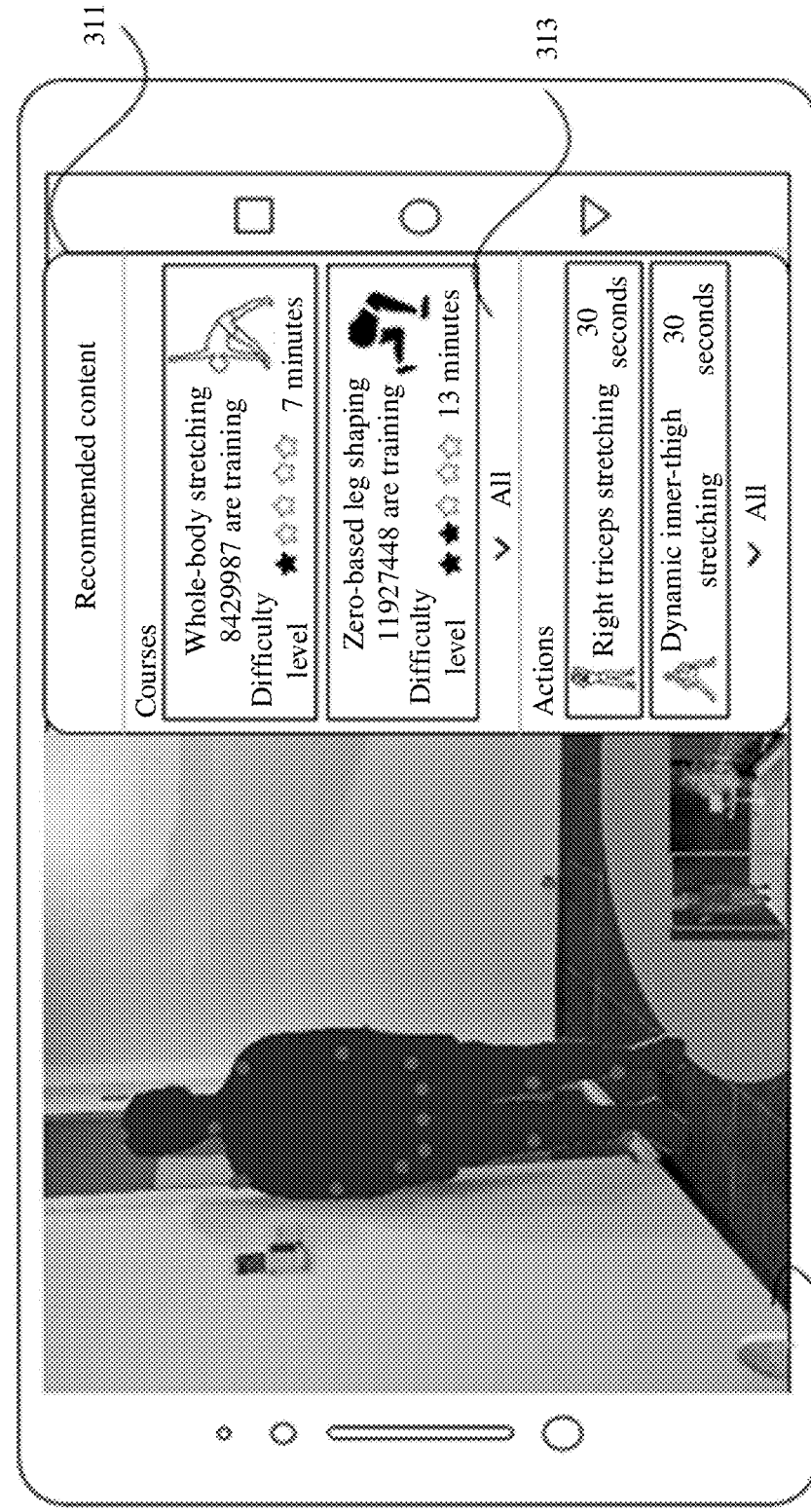
FIG. 11(a) and FIG. 11(b) are schematic diagrams of a graphical user interface in a prompt method according to an embodiment of this application.
Figure 11B:
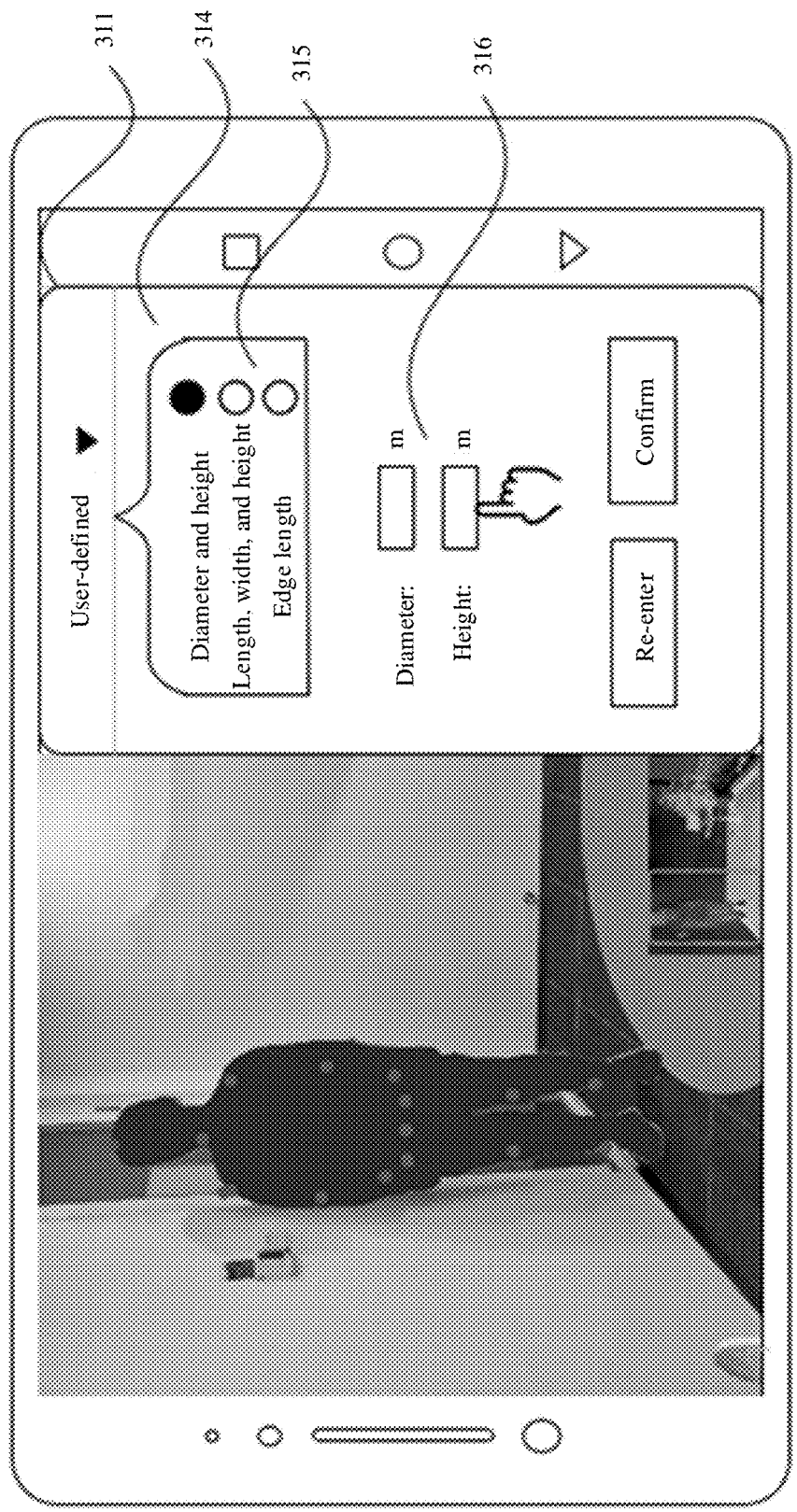

For example, the user may tap a black inverted triangle button in the user-defined window 314. In response to the tapping operation of the user, the mobile phone may display a user-defined type selection box 315 in the recommendation interface 311. In response to an operation that the user taps different types, the mobile phone displays a corresponding input prompt in an input region 316. As shown in FIG. 11(b), a user-defined type may be "a diameter and a height" by default, and the user may input data at diameter and height locations in the input region 316. After the user taps a "confirm" option, a corresponding display interface is entered, for example, the recommended content 313 shown in FIG. 11(a) is displayed. Further, the user may select, from the recommended content 313, a training course or a training action that the user expects to perform. In response to an operation of the user, the mobile phone may display a corresponding interface and perform a corresponding operation. For details, refer to the foregoing descriptions. Details are not described herein again.

In this embodiment of this application, the user may independently determine a size of a space required for exercise, and then the mobile phone recommends, to the user based on a training scenario and the space required by the user, a target training course and/or an action that are/is suitable to perform training in the scenario and that meet/meets a user requirement, so that the user requirement can be met in a more targeted manner and user experience can be improved.

Optionally, in some other embodiments, the mobile phone may recommend a combination of a target course video or a training action to the user based on a training scenario and a body shape parameter of the user such as a height, a waist circumference, and a volume, and recommend a suitable training location to the user, so that the user performs training based on the recommended combination of the target course video or the training action. Because the recommended combination of the target course video or the training action is recommended based on the body shape parameter of the user, the recommended combination of the target course video or the training action is more personalized, and the user better performs training based on the recommended combination of the target course video or the training action in the current training scenario. For example, the mobile phone obtains a video frame of a current environment and processes the current video frame. For example, the mobile phone may recognize the user, and determine a parameter of the user such as a height, a waist circumference, and a volume, to determine space for accommodating a body of the user. In addition, the mobile phone may calculate one or more recommended locations that meet a minimum activity space and/or space that may accommodate the body shape of the user. In addition, the mobile phone may further obtain in advance a maximum activity space required by all training courses and/or all training actions, and determine, based on the one or more recommended locations that meet the minimum activity space and/or the space that may accommodate the body shape of the user and the maximum activity space required by all the training courses and/or all the training actions, a training course and/or a training action that can be used to perform corresponding training at the one or more recommended locations that meet the minimum activity space and/or the space that may accommodate the body shape of the user. For example, the mobile phone may display an interface shown in FIG. 11(a), and display, in recommended content 313, the training course and/or the training action that are/is recommended based on the training scenario and the body shape of the user.

In some embodiments, in a process to determine where the user should stand, that is, in a process from starting the camera application by the mobile phone to movement of the user to the training location recommended by the mobile phone, the mobile phone may obtain a plurality of frames of images of the user, perform subject recognition on the user based on the plurality of frames of images, for example, recognize a skeleton point of the user, and perform an affine transformation on the recognized skeleton point, to ensure that action matching is not affected by an angle, and ensure that a change of the angle of the user relative to a picture does not affect accuracy of the training action evaluation.

With reference to FIG. 3(a) to FIG. 11(b), the foregoing describes a human-computer interaction embodiment of the prompt method provided in the embodiments of this application. For better understanding of the prompt method provided in this application, the following describes a specific implementation process and an algorithm from an implementation perspective.

Figure 12:
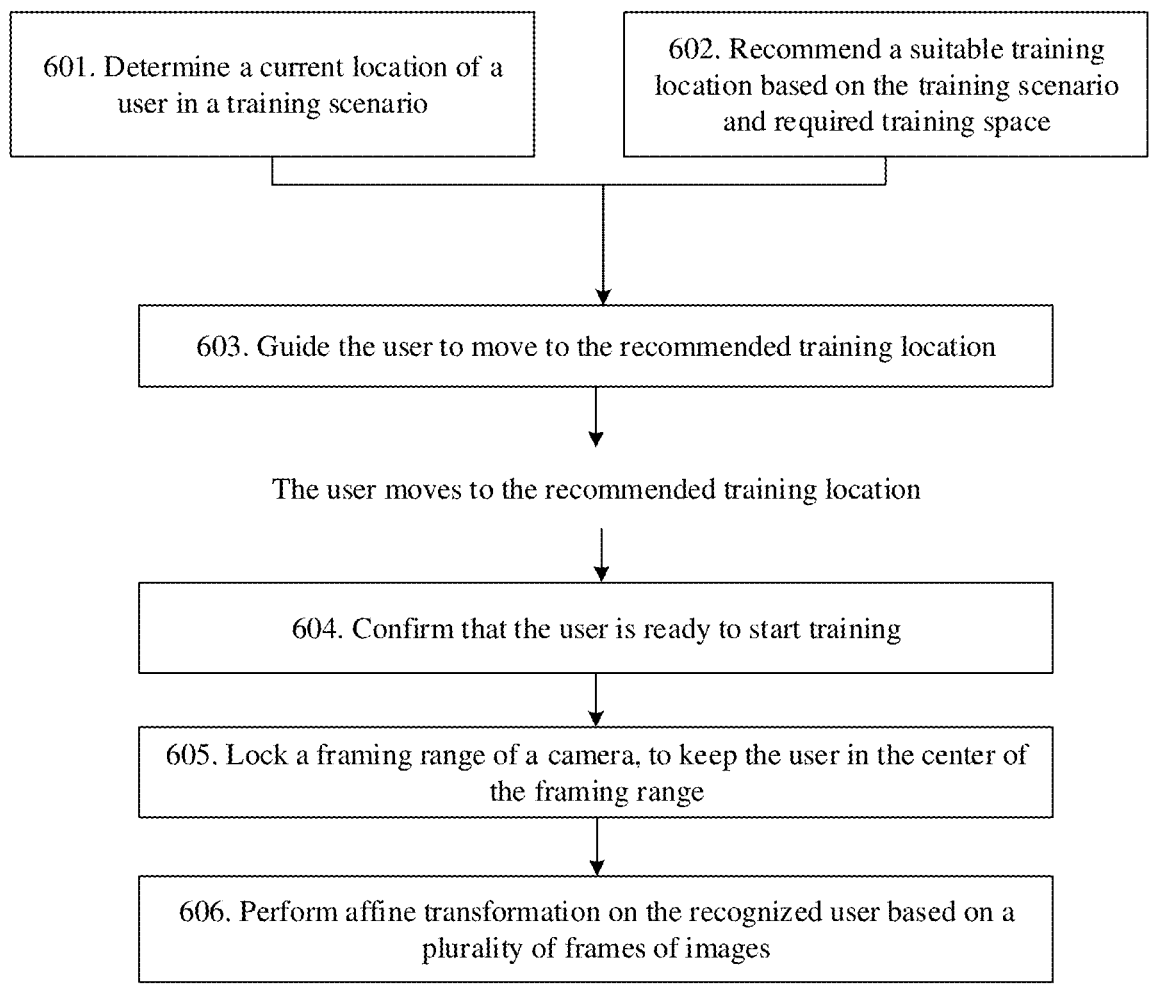
FIG. 12 is a schematic diagram of a processing process of a prompt method according to an embodiment of this application.

FIG. 12 is a schematic diagram of a processing process of a prompt method according to an embodiment of this application. In a specific implementation process, the prompt method may include the following steps.

601. Determine a current location of a user in a training scenario.

It should be understood that determining the current location of the user in the training scenario means recognizing the user in a field of view of a camera. Subject recognition means recognition of a type and a location of an object in an image. That is, a type and a coordinate box of the object are recognized in an output interface. Similarly, in this application, recognizing the user means recognizing the user in the field of view of the camera, and determining a coordinate of a location of the user in the field of view of the camera, namely, the current location of the user in the training scenario. A mobile phone may recognize the user according to a preset algorithm, and the algorithm for recognizing the user is not limited in this application. For example, the mobile phone may determine the coordinate of a location of the user by recognizing a skeleton point (or referred to as skeleton recognition) of the user according to an image algorithm, or may extract information about the user based on three-dimensional depth information, to determine the coordinate of a location of the user. As shown in FIG. 5(a) to FIG. 5(e), the mobile phone may display the recognized skeleton point in the training interface 501.

602. Recommend a suitable training location based on the training scenario and required training space.

The mobile phone may determine the required training space based on an activity space of a coach in a target course video. For example, the mobile phone may determine that a maximum activity space required by a training action in the target course video or a multiple of the maximum activity space is the required training space. For example, the target course video includes a plurality of training actions. The mobile phone uses, as the required training space, activity space corresponding to a training action that requires maximum activity space and that is in the plurality of training actions or a multiple of the activity space. The required training space may be compatible with all training actions, and the user may complete all training actions in the target course video in the required training space.

The mobile phone may determine the required training space for each training action in a plurality of training actions. For example, a target course video includes a plurality of training actions. The mobile phone may calculate space required by each training action, and use the space required by each training action or a multiple of the space as the required training space of each training action. In this way, the mobile phone may recommend a training location corresponding to each training action to the user based on the required training space of each training action.

The mobile phone may determine the required training space based on a body shape parameter of the user. For example, the mobile phone may determine the required training space based on a body shape of the user such as a height and a waist circumference. For example, the mobile phone determines, as the required training space, space occupied when the user extends both arms.

The mobile phone may determine the required training space based on an activity space of a coach in a target course video and a body shape parameter of the user. For example, after a maximum activity space required by a training action in the target course video is obtained, the maximum activity space required by the training action in the target course video is adjusted based on the body shape parameter of the user such as a height and a waist circumference, to obtain the required training space. The required training space is determined based on a body shape of the user, so that the recommended training location is more personalized.

Optionally, the mobile phone may process an activity track of the coach in the target course video, to obtain a maximum activity space required by each training action and/or maximum activity space for completing all the training actions in the target course video.

In an implementation, the required training space may be preset or defined by the user. Specifically, for a user-defined manner, refer to FIG. 11(b). Details are not described herein again. The user independently determines a size of a space required for exercise, so that a user requirement can be met in a more targeted manner and the user experience can be improved.

When the user defines the required training space, the required training space may be a two-dimensional planar graphic such as a circle, an ellipse, a square, a rectangle, or another regular or irregular graphic. A parameter of the required training space may be represented as, for example, an area, a length and a width, or a diameter. The required training space may be in a three-dimensional shape such as a cylinder, an elliptical cylinder, a cuboid, a cube, or another regular or irregular three-dimensional shape. A parameter of the required training space may be represented as, for example, a length, a width, and a height, or a diameter and a height. This is not limited in this embodiment of this application.

After obtaining the required training space, the mobile phone needs to recommend a suitable training location to the user based on the required training space and the training scenario. In other words, after obtaining the training space required for training by the user, the mobile phone needs to determine a location that can meet the required training space and that is in the training scenario in which the user is located, to facilitate training by the user. The mobile phone may scan a current environment (also referred to as a current scenario) by using a depth camera, and calculate, according to a preset algorithm, a location that meets the required training space and that is in the training scenario. The location is the training location recommended by the mobile phone. Optionally, there may be plurality of training locations that meet the required training space. The mobile phone may determine a location closest to the user as the training location recommended to the user, or select any location and determine the location as the training location recommended to the user, or the user selects one of the locations as the recommended training location. This is not limited in this embodiment of this application.

Optionally, steps of recognizing the location of the user by the mobile phone and scanning the training scenario by the mobile phone may be separate. For example, an algorithm for recognizing the location of the user by the mobile phone and an algorithm for scanning the training scenario by the mobile phone may be different. The mobile phone extracts the information about the user according to an algorithm, to recognize the location of the user in the training scenario, and scans the training scenario according to another algorithm, to obtain information about the training scenario. In some other embodiments, the mobile phone may recognize the location of the user and scan the training scenario by using one step. For example, when the mobile phone scans the training scenario, the mobile phone may recognize the location of the user. An algorithm for scanning the training scenario by the mobile phone may also be used to extract the information about the user to recognize the location of the user in the training scenario. Specific algorithms for recognizing the location of the user and scanning the training scenario by the mobile phone are not limited in this embodiment of this application.

Optionally, to expand a recommended location range for the user to stand, in this embodiment of this application, a wide-angle camera or a rotatable camera may be used as the camera. The wide-angle camera has a wide angle of view, and can accommodate a larger scene range within a limited distance. The camera with the rotatable lens may perform photography in a larger scene range by using the rotatable lens. After a larger field of view is obtained, the location to stand recommendation range can be expanded, and a suitable training location can be found more easily.

603. Guide the user to move to the recommended training location.

After determining the training location recommended to the user, the mobile phone may display, in a preview interface or a viewfinder frame, the training location recommended by the mobile phone. For example, the mobile phone may prompt the user with the recommended training location in a recommended region displayed on the ground, for example, the recommended region 505 in FIG. 5(a) to FIG. 5(f).

The user may move based on the recommended training location displayed in the preview interface. In some embodiments, the mobile phone may guide the user to move to the recommended training location in a form such as voice, a prompt box, a direction icon, or a recommended region displayed on the ground. For example, the mobile phone reminds the user that there is an obstruction in the current environment, reminds the user whether the user is in the recommended region, or prompts the user with a movement direction and/or a movement distance. For a specific manner of guiding the user and the display interface, refer to FIG. 5(a) to FIG. 7(b) and the related descriptions. Details are not described herein again.

In a specific implementation process, the mobile phone obtains the coordinate of a location of the user in the current environment and the training location recommended by the mobile phone, and may determine, based on a distance difference between a coordinate of the current location of the user and a coordinate of the recommended training location (for example, a coordinate of the center location in the recommended region), whether the user reaches the recommended training location, or may determine the direction and/or the distance in which the user needs to move. For example, when the distance difference between the coordinate of the current location of the user and the coordinate of the recommended training location (for example, the coordinate of the center location in the recommended region) is greater than a preset threshold, the mobile phone may determine that the user is not at the recommended training location, and the mobile phone guides in any one or a combination of manners such as a prompt box, a direction icon, voice, and a recommended region displayed on the ground, the user to move to the recommended training location. When the distance difference between the coordinate of the current location of the user and the coordinate of the recommended training location (for example, the coordinate of the center location in the recommended region) is less than a preset threshold, the mobile phone may determine that the user is at the recommended training location. The mobile phone may remind the user, in any one or a combination of manners such as a prompt box, a direction icon, voice, and a recommended region displayed on the ground, that the user has reached the recommended training location, or remind the user, in a manner such as a prompt box, a direction icon, voice, or hiding or disappearing of a recommended region displayed on the ground, that the user has reached the recommended training location.

In this embodiment of this application, a field of view and a framing range of the camera may be different. For example, when the wide-angle camera is used, the field of view of the camera may be 5 m, and the framing range may be only 1 m. Therefore, the field of view of the camera cannot be totally displayed on a touchscreen, and only an image in the framing range is displayed. In a process in which the user moves, the camera may perform region of interest (ROI) adaptive adjustment, so that a picture that is of the user and that is in the center of the framing range is always displayed.

604. When determining that the user moves to the recommended training location, the mobile phone confirms that the user is ready to start training.

Optionally, when the mobile phone determines that the user moves to the recommended training location, the mobile phone recognizes a specified action according to an action matching algorithm. After recognizing that the user completes the specified action, the mobile phone confirms that the user is ready to start training. For example, the mobile phone may display the specified action and/or a text prompt in the preview interface, to prompt the user to complete the specified action. For a specific action recognition display interface, refer to FIG. 8(a) and the related descriptions. Details are not described herein again.

Optionally, when the mobile phone determines that the user has moved to the recommended training location, the mobile phone recognizes a specified gesture according to a gesture recognition algorithm. After recognizing that the user completes the specified gesture, the mobile phone confirms that the user is ready to start training For example, the mobile phone may display the specified gesture and/or a text prompt in the preview interface, to prompt the user to complete the specified gesture. For a specific gesture recognition display interface, refer to FIG. 8(b) and the related descriptions. Details are not described herein again.

Optionally, when the mobile phone determines that the user has moved to the recommended training location, the mobile phone recognizes a specified command according to a voice recognition algorithm. After recognizing that the user speaks the specified command, the mobile phone confirms that the user is ready to start training For example, the mobile phone may display an instruction recognition icon and/or a text prompt in the preview interface, to prompt the user to speak the specified command For a specific voice recognition display interface, refer to FIG. 8(c) and the related descriptions. Details are not described herein again.

Optionally, when the mobile phone determines that the user has moved to the recommended training location, the mobile phone starts a timer, for example, performs countdown timing. When timing ends, the mobile phone confirms that the user is ready to start training. For example, the mobile phone may display a countdown timing icon and/or a text prompt in the preview interface, to prompt the user to start training after countdown timing ends. For a specific display interface, refer to FIG. 8(d) and the related descriptions. Details are not described herein again.

Optionally, when the mobile phone determines that the user has moved to the recommended training location, the mobile phone displays a confirmation window in an interface. When detecting a confirmation signal, the mobile phone confirms that the user is ready to start training. For example, the mobile phone may display the confirmation window in the preview interface. For a specific display interface, refer to FIG. 8(e) and the related descriptions. Details are not described herein again.

605. Lock the framing range of the camera, to keep the user in the center of the framing range.

To ensure that a picture range does not change in the user movement process, after determining that the user is ready to start training, the mobile phone locks the framing range of the camera, to keep the user in the center of the framing range. It should be understood that, in this embodiment of this application, keeping the user in the center of the framing range of the camera may be understood as keeping the user in the center of the viewfinder frame in the display interface.

606. Perform an affine transformation on the recognized user based on a plurality of frames of images.

The plurality of frames of images may be obtained in the process in which the user moves to the recommended training location. Affine transformation (affine transformation) is a linear transformation from a two-dimensional coordinate to a two-dimensional coordinate, and maintains "colinearity" (that is, a straight line is still a straight line after transformation) and "parallelism" (that is, a relative location relationship between two-dimensional graphics remains unchanged, parallel lines are still parallel lines, and an order of locations of points on a straight line remains unchanged) of a two-dimensional graphic. In a process of determining where the user should stand, that is, in a process from starting the camera application by the mobile phone to movement of the user to the training location recommended by the mobile phone, the mobile phone may obtain a plurality of frames of images of the user, perform subject recognition on the user based on the plurality of frames of images, for example, recognize a skeleton point of the user, and perform an affine transformation on the recognized skeleton point, to ensure that action matching is not affected by an angle, and ensure that a change of the angle of the user relative to a picture does not affect accuracy of training action evaluation.

In conclusion, in the prompt method provided in this application, a suitable training location is intelligently recommended to the user based on the training scenario and the required training space, and the current location of the user in the training scenario is calculated, so that the user can be guided to the recommended training location. Therefore, the user can normally perform training in a scenario in which exercise space is limited.

Figure 13:
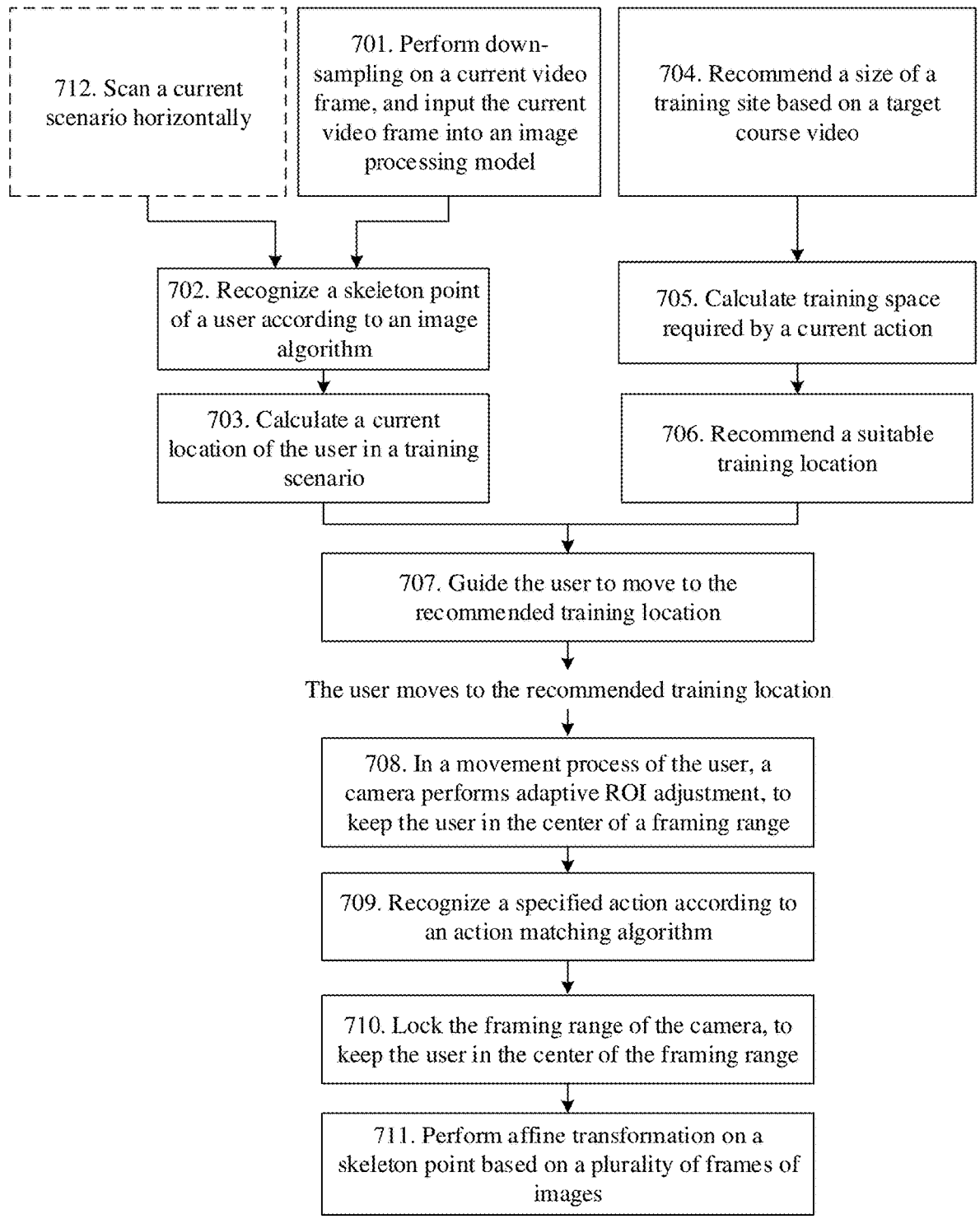
FIG. 13 is a schematic diagram of a processing process of a prompt method according to an embodiment of this application.

FIG. 13 is a schematic diagram of a specific processing process of a prompt method according to an embodiment of this application. Referring to FIG. 13, the method includes the following steps.

After a user taps a start control, in response to the tapping operation of the user, a mobile phone automatically starts a camera application, displays a viewfinder frame in a display interface, and displays preview images of the user and a training scenario in the viewfinder frame.

701. Perform down-sampling on a current video frame, and input the current video frame into a model.

After obtaining the current video frame, the mobile phone performs down-sampling on the current video frame, and inputs the current video frame into an image processing model. The image processing model is used to recognize the user in the current video frame. The image processing model for recognizing the user is not limited in this embodiment of this application.

702. Recognize a skeleton point of the user according to an image algorithm.

In this embodiment of this application, the user may be recognized by using a "skeleton point recognition technology". The "skeleton point recognition technology" is also referred to as a "body detection technology", and is a process in which a location of a joint of a human body may be estimated from an image or a video by using a computer vision technology. An image that includes a human body is given, to accurately position a location of each joint of the human body in the image, for example, an elbow joint, a wrist joint, and a knee joint. The positioned joints may finally form a skeleton diagram of the human body, so that information such as a current posture of the human body can be reflected. With the "skeleton point recognition technology", a posture of the user can be more accurately recognized, to determine an accurate location of the user. As shown in FIG. 5(a) to FIG. 5(f), the dot displayed at the location of the joint of the user in the viewfinder frame 501 is a recognized skeleton point.

703. Calculate a current location of the user in the training scenario.

The current location of the user in the training scenario is calculated based on the skeleton point recognized in step 702. Specifically, a coordinate of a location of the user in a current picture may be calculated.

704. Recommend a size of a training site based on a target course video.

The target course video may be downloaded or buffered by the user to the mobile phone in advance. The mobile phone may process the target course video, calculate maximum activity space required for completing all training actions in the target course video, and determine, based on the maximum activity space required for completing all the training actions in the target course video, the size that is of the training site and that is recommended to the user. It should be understood that the target course video may include a plurality of training actions. The mobile phone may analyze and process an activity track of a coach in the target course video, determine a maximum activity space required by each training action in the plurality of training actions, and determine a maximum value in the required maximum activity space as the maximum activity space required for completing all the training actions in the target course video.

In this step, the mobile phone may select, for the user, a site on which all the training actions in the target course video can be completed, so that the user can complete a training process on the training site without determining the training site again.

Optionally, the size of the training site may be represented by using an area. To be specific, when a ground area in the training scenario meets a value, the mobile phone may recommend the location as the training site, regardless of whether there is an obstruction in space at the location.

705. Calculate training space required by a current action.

The target course video may include a plurality of training actions, and the mobile phone may calculate training space required by each training action. Before the user completes a current training action, the mobile phone calculates the training space required by the current action.

Optionally, the training space required by the current action is a three-dimensional space.

706. Recommend a suitable training location.

The mobile phone recommends a suitable training location to the user according to an algorithm based on the training scenario and the training space required by the current action. For example, the mobile phone may calculate a coordinate of a location at which the user may perform training.

It should be understood that the operation that the mobile phone performs steps 701 to 703 and the operation that the mobile phone performs steps 704 to 706 may be performed simultaneously, or may be performed based on a sequence. This is not limited in this embodiment of this application.

707. Guide the user to move to the recommended training location.

The user may be guided, in a manner such as a notification prompt, a voice prompt, and display of a recommended region in the display interface of the mobile phone, to move to the recommended training location. For a specific manner of guiding the user and the display interface, refer to FIG. 5(a) to FIG. 7(b) and the related descriptions. Details are not described herein again.

708. In a movement process of the user, the camera performs adaptive ROI adjustment, to keep the user in the center of a framing range.

When the user moves to the recommended training location, step 709 is performed, to recognize a specified action according to an action matching algorithm.

In this embodiment of this application, an example is used in which the mobile phone determines, by recognizing that the user completes the specified action, that the user is ready to start training. The interface content shown in FIG. 8(a) may be displayed in the display interface, to prompt the user to complete the specified action. The mobile phone may obtain an image that the user completes the specified action, recognize an action of the user according to the action matching algorithm, and determine accuracy of the action of the user. When a similarity between the action of the user and the specified action meets a requirement, it may be considered that the user has completed the specified action, to continue to perform a next operation.

710. Lock the framing range of the camera, to keep the user in the center of the framing range.

To ensure that a picture range does not change in the movement process of the user, after determining that the user is ready to start training, the mobile phone locks the framing range of the camera, to keep the user in the center of the framing range. It should be understood that, in this embodiment of this application, keeping the user in the center of the framing range of the camera may be understood as keeping the user in the center of the viewfinder frame in the display interface.

711. Perform affine transformation on a skeleton point based on a plurality of frames of images.

The plurality of frames of images may be obtained in the process in which the user moves to the recommended training location. In a process of determining a location for the user to stand, that is, in a process from starting the camera application by the mobile phone to movement of the user to the training location recommended by the mobile phone, the mobile phone may obtain a plurality of frames of images of the user, recognize the skeleton point of the user based on the plurality of frames of images, and perform an affine transformation on the recognized skeleton point, to ensure that action matching is not affected by an angle, and ensure that a change of the angle of the user relative to a picture does not affect accuracy of training action evaluation.

In the following, the mobile phone may perform a play operation on the target course video, for example, play sound in the target course video by using a speaker, to guide the user to start training.

Optionally, to obtain a larger field of view, a wide-angle camera or a rotatable camera may be used as the camera. When the rotatable camera is used, step 701 may be replaced with step 702, to scan a current scenario horizontally. In this step, the camera may rotate by using a rotatable mechanism to scan the current scenario. For example, when a width of a training environment in which the user is located is insufficient to include a whole body of the user into a display range or there is a large quantity of obstructions, a field of view may be obtained by using the rotatable mechanical structure, to expand a recommendation range for locations to stand, and ensure that training is normally performed.

When the rotatable camera is used, in step 705, in the movement process of the user, the camera performs ROI adaptive adjustment, to keep the user in the center of the framing range. When the user moves to an edge of the viewfinder frame, the mechanical structure rotates, to continue to keep the user in the center of the framing range.

Figure 14:
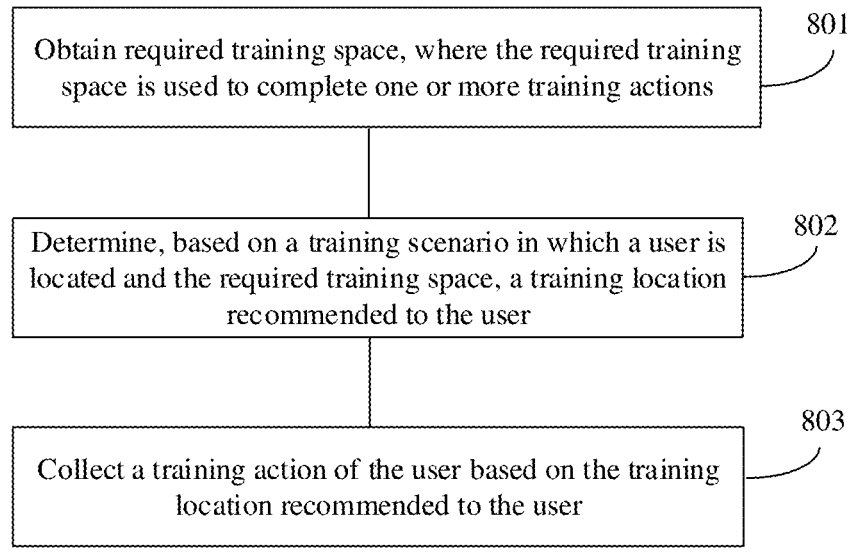
FIG. 14 is a schematic flowchart of a prompt method according to an embodiment of this application.

With reference to the foregoing embodiments and related accompanying drawings, the embodiments of this application provide a prompt method. The method may be implemented by the electronic device (for example, a mobile phone or a tablet computer) having a camera in FIG. 1 and FIG. 2. FIG. 14 is a schematic flowchart of a prompt method according to an embodiment of this application. As shown in FIG. 14, the method may include the following steps.

801. Obtain required training space, where the required training space is used to complete one or more training actions.

There are a plurality of manners of obtaining the required training space.

In a possible implementation, the required training space may be determined based on an activity space of a coach in a target course video and/or a body shape parameter of a user.

For example, the electronic device may determine the required training space based on the activity space of the coach in the target course video. Specifically, the electronic device obtains the target course video, where the target course video includes at least one training action; processes the target course video to obtain training space required by each training action in the at least one training action; and determines, as the required training space, training space corresponding to a training action that requires a maximum training space and that is in the at least one training action. In other words, after obtaining the target course video, the electronic device may process the target course video, for example, analyze an activity track of the coach in the target course video, to obtain the training space required by each training action included in the target course video; and determine, as the required training space based on a comparison result, the training space corresponding to the training action that requires a maximum training space and that is in the target course video. In this way, the determined required training space may be used to complete all training actions in the target course video.

The required training space is determined based on the activity space of the coach in the target course video, and a suitable training location is recommended to the user based on a training scenario and the required training space. The user does not need to select, based on space required by a course, a location for performing training, and the training location is recommended to the user based on the activity space of the coach. The recommended training location is more accurate, and is more suitable for the user to perform training corresponding to the target course video.

For another example, the mobile phone may determine the required training space based on the body shape parameter of the user. Optionally, the electronic device may obtain the body shape parameter of the user by scanning the user. The body shape parameter of the user includes a body size, a weight, a volume, a surface area, and the like. The body size may include a height, an eye height, a shoulder height, an elbow height, a length of an upper arm, a length of a thigh, a length of a crus, and the like. As an example instead of a limitation, the electronic device may determine, as the required training space, a space occupied when the user extends both arms; determine, as the required training space, a volume of a cylinder whose height is a height of the user and whose diameter is a distance that is between fingertips of both hands and that exists when the user extends both arms; or determine, as the required training space, a volume of a cube whose edge length is a height of the user. Specifically, the required training space may be determined according to different algorithms This is not limited in this embodiment of this application.

When the required training space is determined based on the body shape parameter of the user, a training location suitable for the user may be recommended to the user. The recommended training location is more personalized. This improves adaptation between the recommended training location and the training action of the user.

For example, the mobile phone may determine the required training space based on the activity space of the coach in the target course video and the body shape parameter of the user. The electronic device may determine a rough required training space based on the activity space of the coach in the target course video, and then adjust the rough required training space based on the body shape parameter of the user, to obtain the required training space suitable for the user.

When the required training space is determined based on the activity space of the coach in the target course video and the body shape parameter of the user, both a requirement of space required by the training action and a body shape of the user can be considered, so that a training location suitable for the user can be recommended to the user.

In a possible implementation, the required training space may be determined based on a training space parameter defined by the user. For example, the electronic device may display the interface shown in FIG. 11(*b*). In the interface, the user may input a user-defined parameter, such as a diameter and a height, a length, a width, and a height, or an edge length.

In a possible implementation, the required training space may be preset.

802. Determine, based on a training scenario in which the user is located and the required training space, a training location recommended to the user.

The electronic device may obtain information about the training scenario. For example, the electronic device may first start a camera of the electronic device, then obtain an image that is of the training scenario and that is acquired by the camera, and process the acquired image of the training scenario to obtain the information about the training scenario.

The information about the training scenario may include information such as depth information of the training scenario, length, width, and height parameters, or a location, a shape, and a size of an object in the training scenario.

The electronic device may start the camera after detecting a signal that the user taps "start training".

The camera in this embodiment of this application may be any one of an RGB camera, a depth camera, a wide-angle camera, or a camera with a rotatable mechanical structure. When the camera is a depth camera, the depth information of the training scenario by scanning the training scenario, so that the training location recommended to the user is more suitable for the user to perform training. A larger field of view can be obtained by using the wide-angle camera or the camera with the rotatable mechanical structure, so that a range of the training location recommended to the user can be expanded, and a suitable training location can be found more easily.

Optionally, the electronic device may display a processed image that is of the training scenario and that is acquired by the camera, for example, the image displayed in the field of view shown in FIG. 5(b), FIG. 5(d), and FIG. 5(f).

Optionally, the determining, based on a training scenario in which the user is located and the required training space, a training location recommended to the user includes: starting a camera of the electronic device, and scanning the training scenario; and in a scanning process, calculating a location that is in the training scenario and that meets the required training space, and determining the location as the training location recommended to the user.

Optionally, after determining the training location recommended to the user, the electronic device may further guide the user to move to the training location recommended to the user. Specifically, the following steps may be performed: determining a current location of the user in the training scenario; and outputting prompt information based on the current location of the user in the training scenario and the training location recommended to the user, to prompt the user to move to the training location recommended to the user.

It should be understood that the current location of the user in the training scenario may be a current coordinate of a location of the user in the training scenario. The coordinate of a location may be used to obtain a real-time image of the user, process the real-time image of the user according to an image algorithm, recognize the current location of the user in the training scenario, and calculate a coordinate of the location of the user in the training scenario.

Specifically, the electronic device may determine, based on a distance difference between the coordinate of a location of the user in the training scenario and a coordinate of the training location recommended to the user (for example, a coordinate of the center point of the training location recommended to the user), whether the user reaches the recommended training location, or a direction and/or a distance in which the user needs to move, to output prompt information to prompt the user to move to the recommended training location.

The user is guided by using the prompt information, so that the user can quickly reach the recommended training location, and the user does not need to determine the location. This improves user experience, and ensures that the user can also normally perform training in a scenario in which exercise space is limited.

Optionally, the prompt information includes at least one of a picture prompt, a voice prompt, and a notification prompt, for example, a pop-up box notification, a voice prompt, and a recommended region displayed on the ground. For example, the electronic device may display, the interface shown in FIG. 5(a) to FIG. 8(e).

803. Collect a training action of the user based on the training location recommended to the user.

Optionally, before recording the training action of the user based on the training location recommended to the user, the electronic device may prompt the user to confirm to start training. Specifically, the following steps may be performed: determining that the user moves to the training location recommended to the user; and outputting confirmation information, where the confirmation information is used to prompt the user to start training.

Optionally, the confirmation information may include a manner such as action recognition, gesture recognition, voice recognition, countdown timing, and Bluetooth confirmation. When the user completes specified action matching, specified gesture recognition, specified command recognition, or Bluetooth confirmation, or countdown timing ends, the mobile phone determines that the user has started training. For example, the electronic device may display the interface shown in FIG. 8(a) to FIG. 8(e).

Optionally, after the user starts training, the electronic device may evaluate the training action of the user. To ensure that action matching is not affected by an angle, and ensure that a change of the angle of the user relative to a picture does not affect accuracy of a training action evaluation, before the user starts training, the method further includes: obtaining a plurality of frames of images of the user, where each frame of image in the plurality of frames of images includes at least one recognized point; and performing an affine transformation on any two frames of images in the plurality of frames of images based on the at least one recognized point.

In this embodiment of this application, a suitable training location is recommended to the user based on the training scenario and the required training space. Therefore, the user can also normally perform training in a scenario in which exercise space is limited, for example, when there is an obstruction or the site is insufficient. Further, the user may be guided to the recommended training location by using the prompt information, so that the user can quickly reach the recommended training location, and the user does not determine the training location. This improves user experience.

It may be understood that, to implement the foregoing functions, the electronic device includes corresponding hardware and/or software modules for performing the functions. With reference to algorithm steps of each example described in the embodiments disclosed in this specification, this application can be implemented in a form of hardware or a combination of hardware and computer software. Whether a function is performed by hardware or hardware driven by computer software depends on the particular applications and design constraints of the technical solutions. A person skilled in the art may use different methods to implement the described functions for each particular application with reference to the embodiments, but it should not be considered that the implementation goes beyond the scope of this application.

In the embodiments, the electronic device may be divided into function modules based on the foregoing method examples. For example, each function module corresponding to each function may be obtained through division, or two or more functions may be integrated into one processing module. The integrated module may be implemented in a form of hardware. It should be noted that division into modules in the embodiments is an example, and is merely logical function division. In an actual implementation, another division manner may be used.

Figure 15:
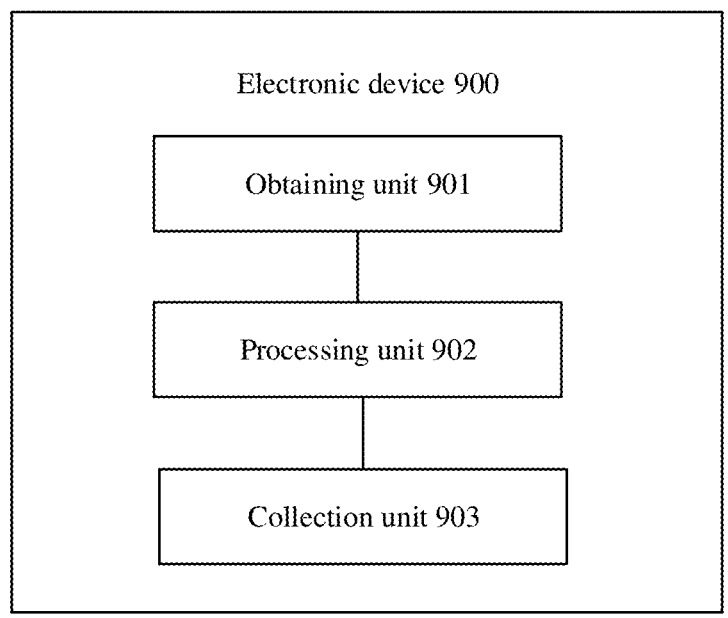
FIG. 15 is a schematic composition diagram of an electronic device according to an embodiment of this application.

When each function module is obtained through division by using each corresponding function, FIG. 15 is a schematic diagram of possible composition of an electronic device 900 in the foregoing embodiments. As shown in FIG. 15, the electronic device 900 may include an obtaining unit 901, a processing unit 902, and a collection unit 903.

The obtaining unit 901 may be configured to support the electronic device 900 in performing step 801 and/or another process used in the technology described in this specification, for example, step 704 and step 705 in FIG. 13.

The processing unit 902 may be configured to support the electronic device 900 in performing step 802 and/or another process used in the technology described in this specification, for example, step 702, step 703, and step 707 to step 711 in FIG. 13.

The collection unit 903 may be configured to support the electronic device 900 in performing step 803 and/or another process used in the technology described in this specification.

It should be noted that all related content of the steps in the foregoing method embodiments may be cited in function description of corresponding function modules. Details are not described herein again.

The electronic device provided in this embodiment is configured to perform the prompt method. Therefore, effects that are the same as those of the foregoing implementation method can be achieved.

When an integrated unit is used, the electronic device may include a processing module, a storage module, and a communications module. The processing module may be configured to control and manage an action of the electronic device, for example, may be configured to support the electronic device in performing the steps performed by the obtaining unit 901, the processing unit 902, and the collection unit 903. The storage module may be configured to support the electronic device to store program code, data, and the like. The communications module may be configured to support communication between the electronic device and another device.

The processing module may be a processor or a controller. The processing module may implement or execute various example logical blocks, modules, and circuits described with reference to content disclosed in this application. Alternatively, the processor may be a combination of processors implementing a computing function, for example, a combination of one or more microprocessors, or a combination of a digital signal processor (DSP) and a microprocessor. The storage module may be a memory. The communications module may be specifically a device that interacts with another electronic device, such as a radio frequency circuit, a Bluetooth chip, or a Wi-Fi chip.

In an embodiment, when the processing module is a processor and the storage module is a memory, the electronic device in this embodiment may be a device having the structure shown in FIG. 1.

An embodiment further provides a computer storage medium. The computer storage medium stores computer instructions; and when the computer instructions are run on an electronic device, the electronic device is enabled to perform the foregoing related method steps, to implement the prompt method in the foregoing embodiments.

An embodiment further provides a computer program product. When the computer program product runs on a computer, the computer is enabled to perform the foregoing related steps, to implement the prompt method in the foregoing embodiments.

In addition, an embodiment of this application further provides an apparatus. The apparatus may be specifically a chip, a component, or a module. The apparatus may include a processor and a memory that are connected to each other. The memory is configured to store computer-executable instructions. When the apparatus runs, the processor may execute the computer-executable instructions stored in the memory, to enable the chip to perform the prompt method in the foregoing method embodiments.

The electronic device, the computer storage medium, the computer program product, or the chip provided in the embodiments is configured to perform a corresponding method provided above. Therefore, for beneficial effects that can be achieved by the electronic device, the computer storage medium, the computer program product, or the chip, refer to beneficial effects of the corresponding method provided above. Details are not described herein again.

The foregoing descriptions about implementations allow a person skilled in the art to understand that, for convenient and brief description, division into the foregoing function modules is taken as an example for illustration. In actual application, the foregoing functions can be allocated to different function modules for implementation according to a requirement, in other words, an inner structure of an apparatus is divided into different function modules to implement all or some of the functions described above.

In the several embodiments provided in this application, it should be understood that the disclosed apparatus and method may be implemented in another manner. For example, the described apparatus embodiment is merely an example. For example, division into the modules or units is merely logical function division and may be other division in actual implementation. For example, a plurality of units or components may be combined or integrated into another apparatus, or some features may be ignored or not performed. In addition, the displayed or discussed mutual coupling or direct coupling or communication connections may be implemented by using some interfaces. The indirect coupling or communication connections between the apparatuses or units may be implemented in electronic, mechanical, or other forms.

The units described as separate parts may or may not be physically separate, and parts displayed as units may be one or more physical units, may be located in one place, or may be distributed on different places. Some or all of the units may be selected based on actual requirements to achieve the objectives of the solutions of the embodiments.

In addition, function units in the embodiments of this application may be integrated into one processing unit, or each of the units may exist alone physically, or two or more units may be integrated into one unit. The integrated unit may be implemented in a form of hardware, or may be implemented in a form of a software function unit.

When the integrated unit is implemented in a form of a software function unit and sold or used as an independent product, the integrated unit may be stored in a readable storage medium. Based on such an understanding, the technical solutions of the embodiments of this application essentially, or the part contributing to the current technology, or all or some of the technical solutions may be implemented in a form of a software product. The software product is stored in a storage medium and includes several instructions for instructing a device (which may be a single-chip microcomputer, a chip, or the like) or a processor to perform all or some of the steps of the methods described in the embodiments of this application. The foregoing storage medium includes any medium that can store program code, such as a USB flash drive, a removable hard disk, a read-only memory (ROM), a random access memory (RAM), a magnetic disk, or an optical disc.

The foregoing content is merely specific implementations of this application, but is not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A method for fitness training, applied to an electronic device, the method comprising:
    determining, by the electronic device, a minimum volume required for a user to complete one or more physical exercise actions;
    determining, by the electronic device, based on a training region in which the user is located and the minimum volume, a training location to recommend to the user to perform the one or more actions; and
    recording, by the electronic device, at least one of the one or more actions of the user based on the training location recommended to the user.

2. The method according to claim 1, wherein obtaining the minimum volume comprises:
    determining the minimum volume based on an activity space of a coach in a target course video;
    determining the minimum volume space based on a body shape parameter of the user;
    determining the minimum volume based on the activity space of the coach in the target course video and the body shape parameter of the user; or
    determining the minimum volume based on a training space parameter defined by the user.

3. The method according to claim 1, wherein determining the training location recommended to the user comprises:
    starting a camera of the electronic device, and scanning the training region; and
    while scanning, calculating a location that is in the training region and that meets the minimum volume, wherein the location is the training location recommended to the user.

4. The method according to claim 3, wherein the camera is any one of an RGB camera, a depth camera, a wide-angle camera, or a camera mounted to a rotatable mechanical structure.

5. The method according to claim 1, further comprising:
    determining a current location of the user in the training region; and
    outputting prompt information based on the current location and the training location, to prompt the user to move to the training location.

6. The method according to claim 5, wherein the prompt information comprises at least one of a picture prompt, a voice prompt, and a notification prompt.

7. The method according to claim 1, wherein before recording the training action of the user the method further comprises:
    determining that the user has moved to the training location; and
    outputting confirmation information used to prompt the user to start training.

8. The method according to claim 1, further comprising:
    obtaining a plurality of frames of images of the user, wherein each frame in the plurality of frames comprises at least one recognized point; and
    performing an affine transformation on any two frames in the plurality of frames of images based on the at least one recognized point.

9. A non-transitory computer storage medium, comprising computer instructions, wherein when the computer instructions are run on an electronic device, the electronic device is enabled to perform the prompt method according to claim 1.

10. An electronic device, comprising:
    one or more processors;
    one or more memories;
    a plurality of applications; and
    one or more programs, wherein the one or more programs are stored in the memory, and when the one or more programs are executed by the processor, the electronic device is enabled to perform the following steps:
    obtaining a minimum volume used to complete one or more physical exercise actions;
    determining, based on a training region in which a user is located and the minimum volume, a training location recommended to the user to perform the one or more actions; and
    recording at least one of the one or more actions of the user based on the training location.

11. The electronic device according to claim 10, wherein when the one or more programs are executed by the processor, the electronic device is enabled to obtain the minimum volume by:
    determining the minimum volume based on an activity space of a coach in a target course video;
    determining the minimum volume based on a body shape parameter of the user;
    determining the minimum volume based on the activity space of the coach in the target course video and the body shape parameter of the user; or
    determining the minimum volume based on a training space parameter defined by the user.

12. The electronic device according to claim 10, wherein when the one or more programs are executed by the processor, the electronic device is enabled to determine the training location by:
    starting a camera of the electronic device, and scanning the training region; and
    while scanning, calculating a location that is in the training region and that meets the minimum volume, wherein the location is the training location recommended to the user.

13. The electronic device according to claim 12, wherein the camera is any one of an RGB camera, a depth camera, a wide-angle camera, or a camera mounted to a rotatable mechanical structure.

14. The electronic device according to claim 10, wherein when the one or more programs are executed by the processor, the electronic device is enabled, before recording the training action of the user to:
   determine a current location of the user in the training region; and
   output prompt information based on the current location of the user in the training region and the training location recommended to the user, to prompt the user to move to the training location recommended to the user.

15. The electronic device according to claim 14, wherein the prompt information comprises at least one of a picture prompt, a voice prompt, and a notification prompt.

16. The electronic device according to claim 10, wherein when the one or more programs are executed by the processor, the electronic device is enabled, before recording the training action of the user to:
   determine that the user has moved to the training location recommended to the user; and
   output confirmation information is used to prompt the user to start training.

17. The electronic device according to claim 10, wherein when the one or more programs are executed by the processor, the electronic device is further enabled to:
   obtain a plurality of frames of images of the user, wherein each frame in the plurality of frames comprises at least one recognized point; and
   perform an affine transformation on any two frames in the plurality of frames of images based on the at least one recognized point.

* * * * *